US012226579B2

(12) United States Patent
Ronayne et al.

(10) Patent No.: US 12,226,579 B2
(45) Date of Patent: Feb. 18, 2025

(54) NASAL CANNULA AND SECUREMENT SYSTEM

(71) Applicant: Fisher & Paykel Healthcare Limited, Auckland (NZ)

(72) Inventors: Michael Paul Ronayne, Auckland (NZ); Anna Rose Northey, Auckland (NZ); Brad Michael Howarth, Auckland (NZ); Leon Tyler Stanley, Auckland (NZ); Samuel Rollo Ross Davis, Auckland (NZ); Julio Derek Meech, Auckland (NZ); James William Stanton, Auckland (NZ); Larissa Grace Michelsen, Auckland (NZ); Oscar Elliot James McGerty, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 709 days.

(21) Appl. No.: 17/253,052

(22) PCT Filed: Jun. 19, 2019

(86) PCT No.: PCT/NZ2019/050073
§ 371 (c)(1),
(2) Date: Dec. 16, 2020

(87) PCT Pub. No.: WO2019/245391
PCT Pub. Date: Dec. 26, 2019

(65) Prior Publication Data
US 2021/0370003 A1    Dec. 2, 2021

Related U.S. Application Data

(60) Provisional application No. 62/769,531, filed on Nov. 19, 2018, provisional application No. 62/687,230, filed on Jun. 19, 2018.

(51) Int. Cl.
*A61M 16/06* (2006.01)

(52) U.S. Cl.
CPC .... *A61M 16/0666* (2013.01); *A61M 16/0683* (2013.01); *A61M 16/0688* (2014.02); *A61M 16/0694* (2014.02); *A61M 2240/00* (2013.01)

(58) Field of Classification Search
CPC .......... A61M 16/0666; A61M 16/0688; A61M 16/0694; A61M 16/16; A61M 2205/6081;
(Continued)

(56) References Cited

U.S. PATENT DOCUMENTS 5,682,881 A    11/1997  Winthrop et al.
9,795,770 B1   10/2017  Zolli
(Continued)

FOREIGN PATENT DOCUMENTS

EP    2130563 A1       12/2009
WO    WO 2009/020840    2/2009
(Continued)

OTHER PUBLICATIONS

Patent Cooperation Treaty, International Search Report and Written Opinion, Application No. PCT/NZ2019/050073, dated Oct. 28, 2019, in 26 pages.

*Primary Examiner* — Joseph D. Boecker
(74) *Attorney, Agent, or Firm* — Knobbe Martens Olson & Bear LLP

(57) ABSTRACT

A patient interface assembly has a patient interface and a securement system for the patient interface and/or patient interface tubing. The patient interface has a body and at least one nasal prong extending from the body. The at least one nasal prong has a gas inlet for fluid communication with a supply of breathable gas, and a gas outlet configured to direct a flow of gas towards a nare of the user's nose. The at least one nasal prong further includes an exterior surface,
(Continued)

at least a portion of the exterior surface is a sealing surface configured to seal the nare of the user's nose. The securement system has a two-part releasable attachment or connection arrangement, the arrangement comprising a first patch and a second patch.

22 Claims, 51 Drawing Sheets

(58) Field of Classification Search
CPC ........ A61M 2209/082; A61M 2240/00; A61M 16/0875; A61M 16/00; A61M 2025/0206; A61M 2025/0226; A61M 2025/024; A61M 2025/0253; A61M 2025/026; A61M 2025/0266; A61M 16/0672; A61M 16/0683
See application file for complete search history.

(56) References Cited

U.S. PATENT DOCUMENTS

| | | | |
|---|---|---|---|
| 2003/0172936 A1 | 9/2003 | Wilkie et al. | |
| 2004/0025884 A1* | 2/2004 | McKown | A61M 16/0666 128/207.18 |
| 2004/0230108 A1* | 11/2004 | Melker | A61B 5/14551 128/204.23 |
| 2009/0032018 A1* | 2/2009 | Eaton | A61M 39/1055 128/205.24 |
| 2011/0126841 A1 | 6/2011 | Matula, Jr. et al. | |
| 2011/0214676 A1 | 9/2011 | Allum et al. | |
| 2011/0315146 A1* | 12/2011 | Beevers | A61M 16/0666 128/207.13 |
| 2013/0306081 A1* | 11/2013 | Devapatla | A61M 16/0683 128/876 |
| 2014/0000626 A1 | 1/2014 | O'Connor et al. | |
| 2015/0075534 A1* | 3/2015 | Gulliver | A61M 16/0683 128/207.13 |
| 2015/0090255 A1 | 4/2015 | Gulliver et al. | |
| 2015/0136139 A1 | 5/2015 | Franzen | |
| 2016/0158476 A1 | 6/2016 | Tatkov | |
| 2016/0235937 A1 | 8/2016 | Ronayne et al. | |
| 2016/0296720 A1 | 10/2016 | Henry et al. | |
| 2017/0340849 A1 | 1/2017 | Anderson | |
| 2017/0021121 A1 | 11/2017 | Anderson | |
| 2017/0348500 A1 | 12/2017 | Johnson et al. | |
| 2018/0036503 A1* | 2/2018 | Mohamed | A61M 16/0666 |
| 2018/0078726 A1 | 3/2018 | Barraclough et al. | |

FOREIGN PATENT DOCUMENTS

| | | |
|---|---|---|
| WO | WO 2009/052560 | 4/2009 |
| WO | WO 2016/048172 | 3/2016 |
| WO | WO 2016/159783 | 10/2016 |
| WO | WO 2016/159783 A1 | 10/2016 |
| WO | WO 2018/042355 | 3/2018 |

* cited by examiner

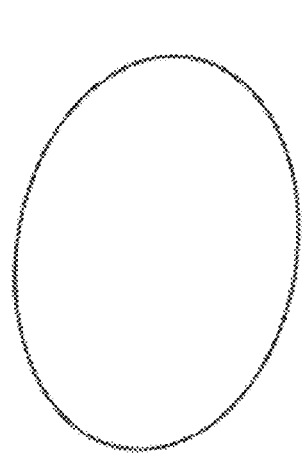
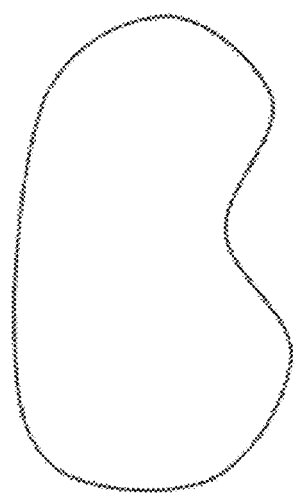
FIG. 13A          FIG. 13B
FIG. 14
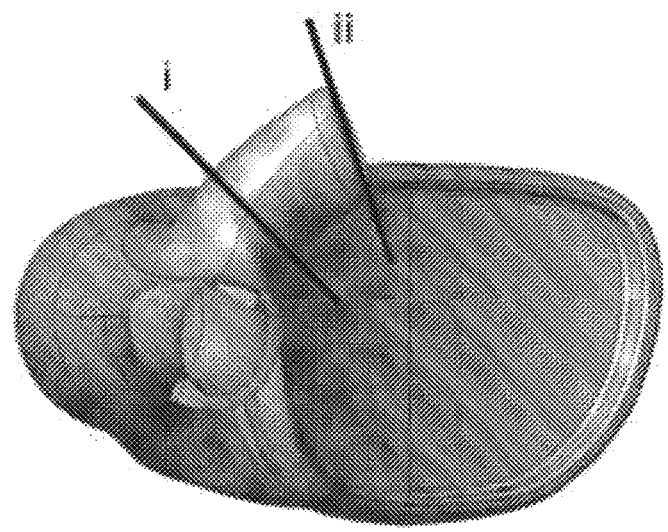
FIG. 15

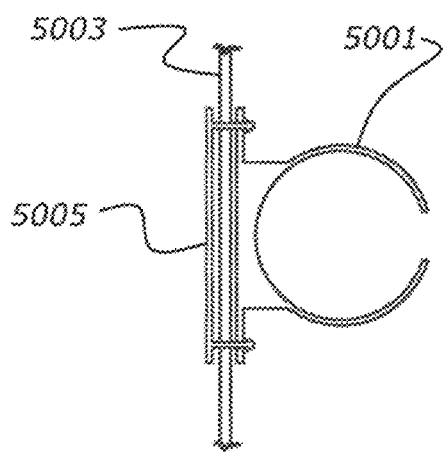
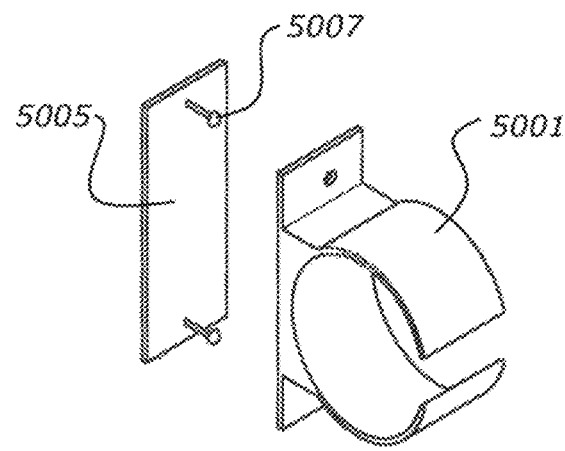
*FIG. 50A*  *FIG. 50B*
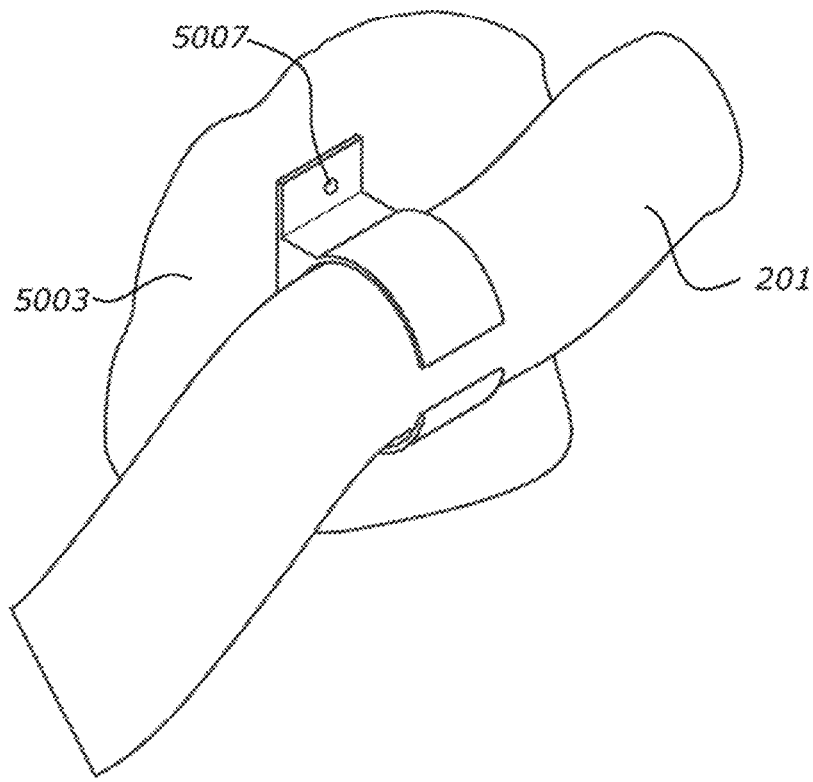
*FIG. 50C*

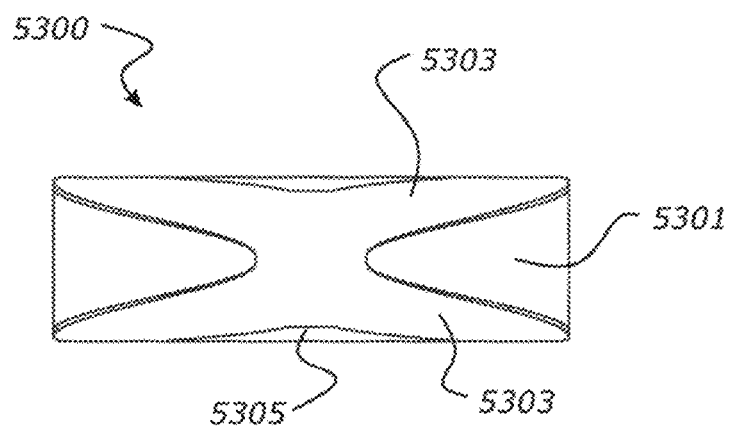
FIG. 53A
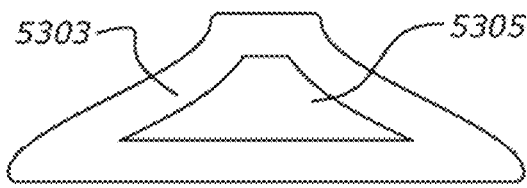
FIG. 53B
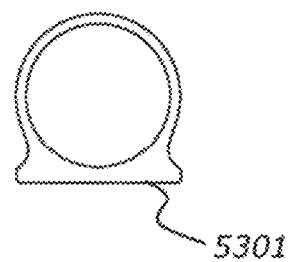
FIG. 53C
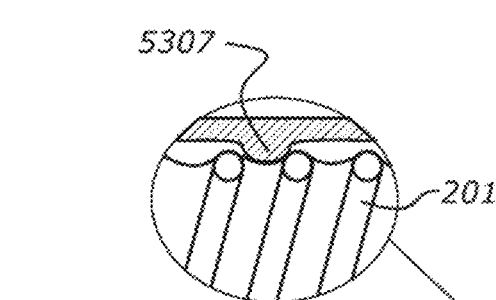
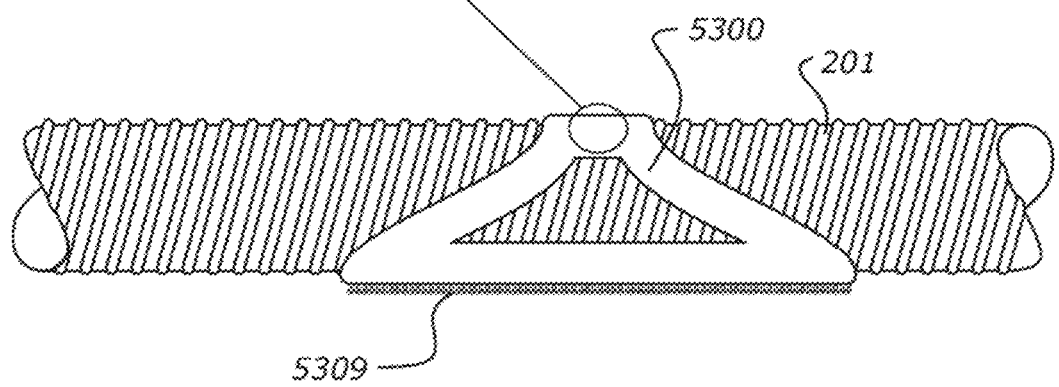
FIG. 53D

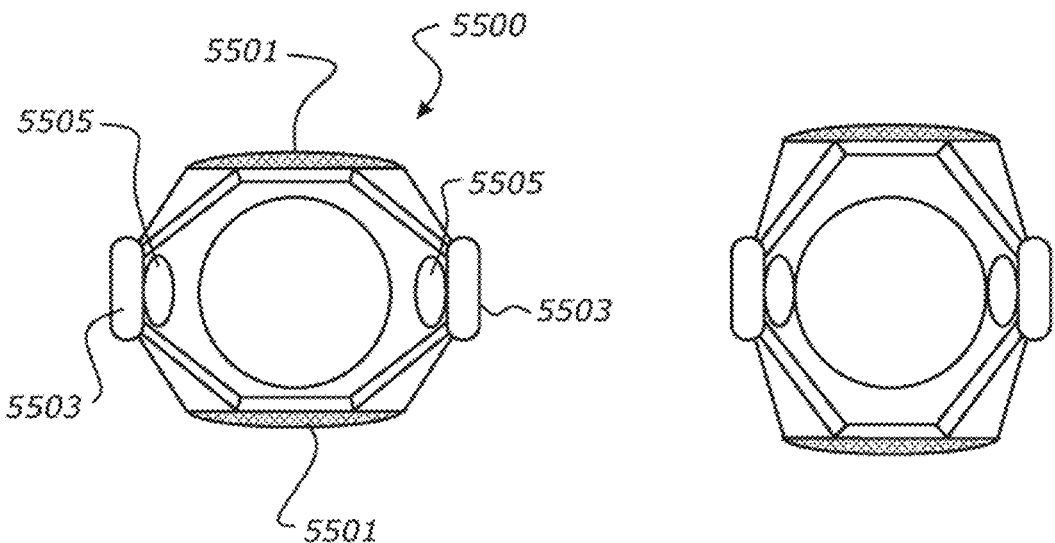
*FIG. 55A*  *FIG. 55B*
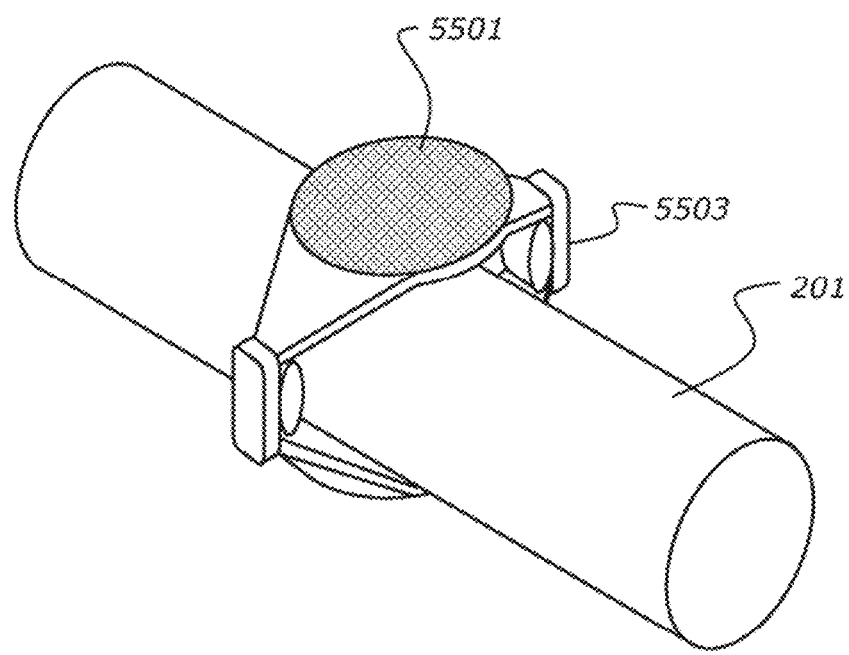
*FIG. 55C*

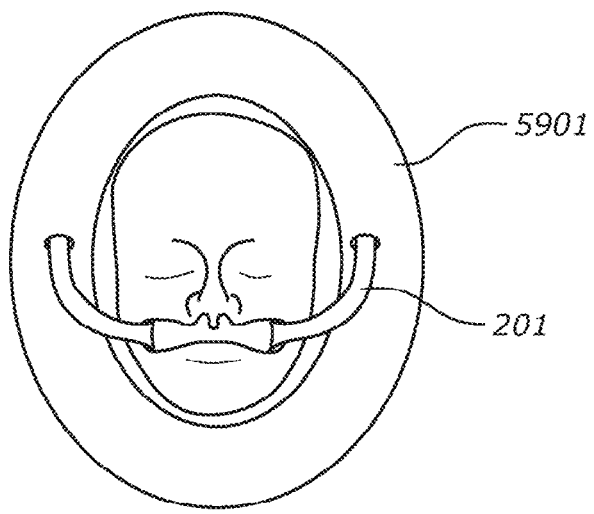
FIG. 59
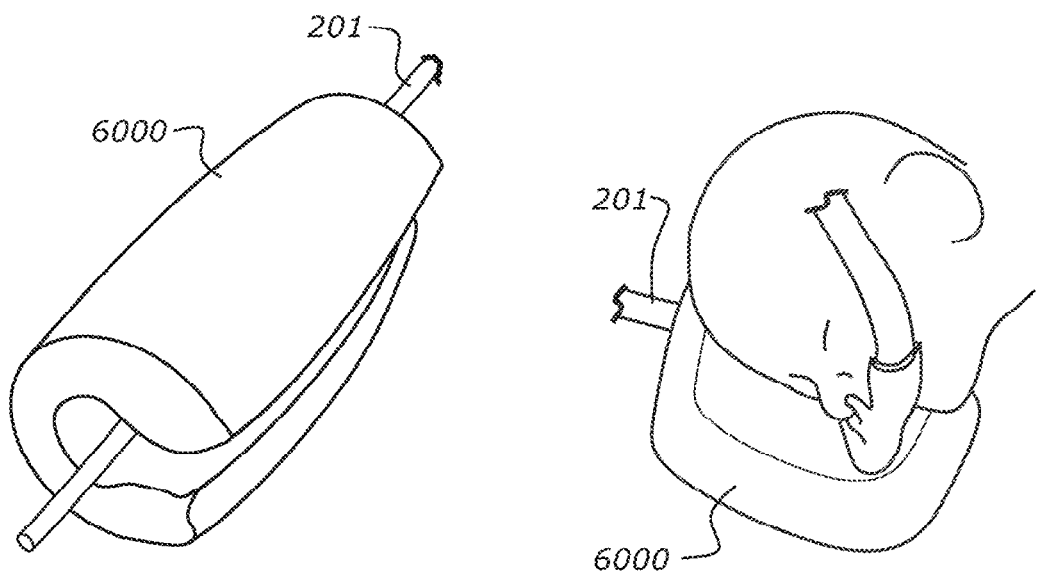
FIG. 60A  FIG. 60B

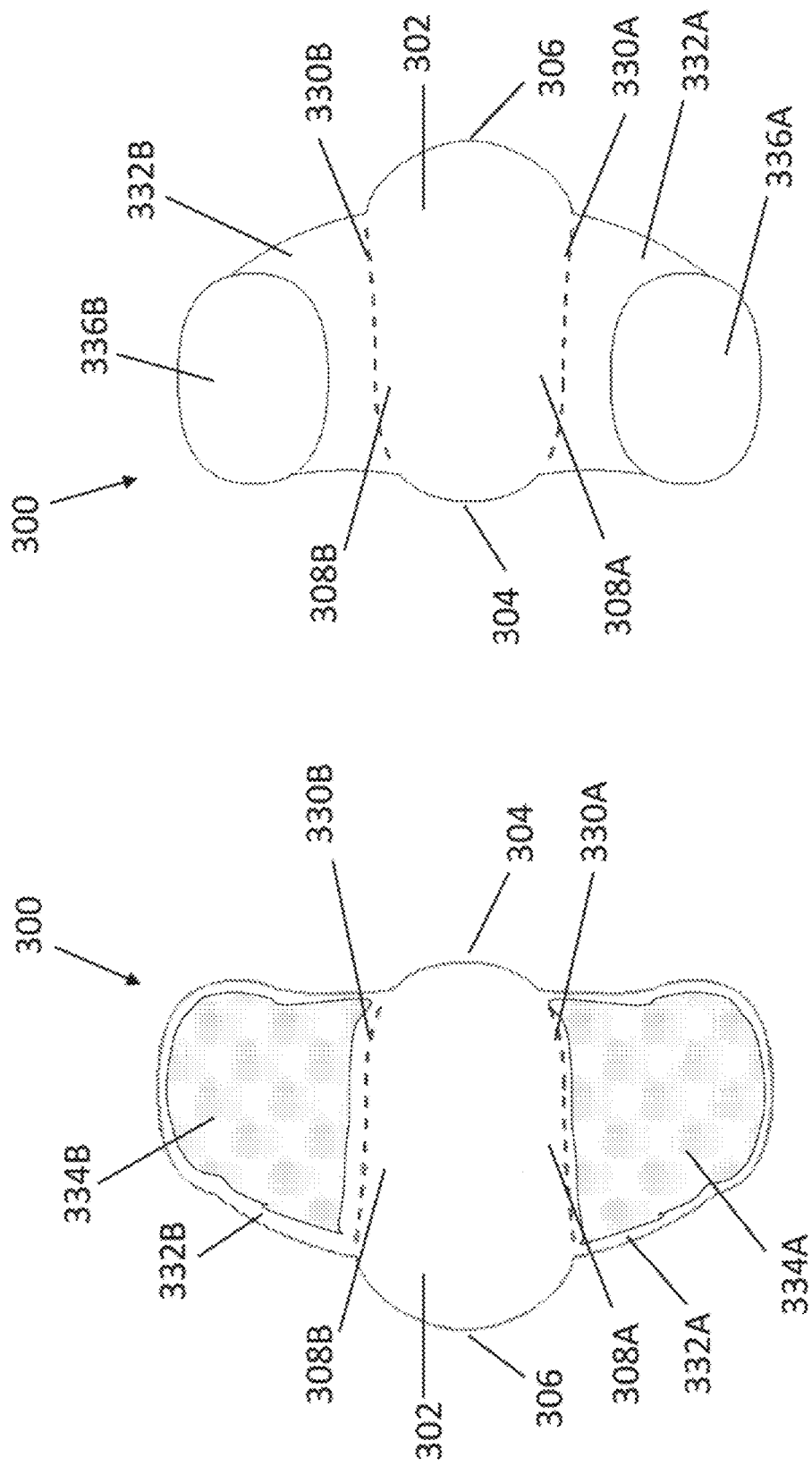

NASAL CANNULA AND SECUREMENT SYSTEM

FIELD OF THE INVENTION

The present disclosure generally relates to components for medical systems for conveying gases to and/or from a patient. In one particular aspect, the disclosure relates to patient interfaces that form a part of a breathing system.

BACKGROUND OF THE INVENTION

In assisted breathing, respiratory gases are supplied to a patient through a patient interface via flexible breathing tube. The patient interface can be a nasal cannula, nasal mask, full face or oro-nasal mask, endotracheal tube, or other known types of interfaces. The gases expired by the patient may be channelled through a similar breathing tube to other equipment (valves, ventilators, pressure devices, or the like) or expelled to the patient's surroundings.

In medical applications, such as assisted breathing, the gases inhaled by a patient are preferably delivered close to body temperature (usually between 33° C. and 37° C.) and with a high relative humidity (commonly near saturation). In other medical applications, such as continuous positive airway pressure (CPAP) systems or positive pressure ventilations systems that provide patient's suffering obstructive sleep apnea (OSA) with positive pressure breathing gases, the breathing gases may be heated and/or humidified to varying levels to improve user comfort or supplied without heating or humidification.

It would be advantageous to provide a system for an alternative or improved interface location or operational positioning of the interface, such as a nasal cannula. Such an alternative or improved system may further assist with improved compliance of gas delivery treatment.

In the specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

Further aspects and advantages of the present disclosure will become apparent from the ensuing description which is given by way of example only.

SUMMARY OF THE INVENTION

In one aspect, the disclosure broadly consists in a patient interface assembly comprising: a patient interface comprising: a body and at least one nasal prong extending from the body, the at least one nasal prong having a gas inlet for fluid communication with a supply of breathable gas, and a gas outlet configured to direct a flow of gas towards a nare of the user's nose, the at least one nasal prong further including an exterior surface, at least a portion of the exterior surface is a sealing surface configured to seal the nare of the user's nose; and a securement system for the patient interface and/or patient interface tubing comprising a two-part releasable attachment or connection arrangement, the arrangement comprising a first patch and a second patch.

In one embodiment, each prong is an inspiratory and expiratory prong.

In one embodiment, each of the prongs is in fluid communication with the other of the prongs via a manifold.

In one embodiment, the manifold is fully and always open between the prongs.

In one embodiment:
the first patch has a patient side and an interface side, the patient side of the first patch being attachable to the skin of a user, (such as for example by an adhesive, generally being of a dermatologically sensitive adhesive such as a hydrocolloid) or being attachable to an item being worn by the user, the interface side of the first patch being provided with the first part of a two-part releasable attachment or connection system,
the second patch having an interface side and patient side, the patient side of the second patch being provided with the complimentary second part of the two-part releasable attachment or connection system, and
the interface side of the second patch being attachable or connected to the patient interface and/or associated patient interface tubing, for example by adhesive or may be formed as a part of the patient interface or may be provided as a back surface of the patient interface upon which is provided the second part of the two-part system.

In one embodiment, the interface side of the first patch has one of a hook or a loop, and the second part of the second patch has the other of the hook or loop, such that the first and second parts (and patches) are releasably attachable or connectable to each other.

In one embodiment, the first patch is locatable and/or attachable to the skin of a user's face.

In one embodiment, the second patch is locatable, or attached or attachable, or is connected to, or with, a patient interface.

In one embodiment, the second patch is formed integrally with, or forms a part of, a patient interface.

In one embodiment, the first part of the two-part releasable attachment or connection system on the first patch occupies less than about 90%, or about 85%, or about 75%, or about 60% or about 50% or about 40% or about 30% or about 20% or about 10% of the interface side of the first patch.

In one embodiment, the first part of the two-part releasable attachment or connection system is adhered or adherable to the patient interface side of the first patch with a suitable adhesive.

In one embodiment, the user side of the first patch has a dermatologically sensitive adhesive (such as a hydrocolloid for example) that attaches or adheres the first patch to a user's skin.

In one embodiment, the first patch has a surface of sufficient area such that, the surface distributes pressure the attachment or adhering forces across the user's skin.

In one embodiment, the first patch is configured to attach or adhere to a user's face.

In one embodiment, the first patch is configured to attach or adhere to a user's face adjacent the user's upper lip and/or cheek.

In one embodiment, the securement system is configured to receive and/or secure a nasal cannula and associated tubing, the tubing extending from one or both sides of a user's face.

In one embodiment, the securement system is configured for use with an infant or neonatal infant.

In one embodiment, the patient interface comprises a securement patch configured to be applied or applicable over the patient interface and affixed or affixable to the first patch to provide additional securement.

In one embodiment, the first part of the two-part releasable attachment or connection system includes a substrate portion secured to, or for securing to, the first patch.

In one embodiment, the substrate portion includes at least one slit or at least one slot with areas of the substrate portion separated by the slit or slot.

In one embodiment, the substrate portion includes a plurality of slits or slots or both which together divide the substrate portion into a serpentine body.

In one embodiment, the slits and/or slots are arranged in the substrate such that a first set of at least one set of slits or slots extends into the substrate from one edge of the substrate and a second set of slits or slots extends into the substrate from the other edge of the substrate, the slits or slots of a set being interleaved with the slits or slots of the other set such that a path along the substrate portion from one end to another end without crossing the slits or slots must follow a zigzag or serpentine path much longer than a direct line between the ends.

In one embodiment, a slit or slot of the plurality of slits or slots is curved.

In one embodiment, a plurality of the slits or slots is curved and the curved slits or slots are arranged substantially parallel.

In one embodiment, the slits or slots are arranged in a herring bone pattern extending in from the edges of the substrate portion.

In one embodiment, the substrate is divided into separated portions by a serpentine slit or slot.

In one embodiment, the substrate portion is divided into portions by a spiral slit or slot.

In one embodiment, the substrate portion is divided into sub-portions by slits or slots arranged on substantially concentric circles.

In one embodiment, the concentric circles are centred at approximately the centre of the substrate portion.

In one embodiment, the slit or slots divide the substrate portion into a plurality of islands, each joined to an adjacent island or islands by a narrow bridge.

In one embodiment, the substrate portion is divided into portions by an S-shaped slit.

In one embodiment, the substrate portion is divided into portions by a T-shaped slit.

In one embodiment, the substrate portion covers at least 70% of the area of the first patch.

In one embodiment, for a boundary defining the shortest path around the perimeter of the substrate, the substrate portion covers at least 80% of the area within the boundary.

In one embodiment, there is provided a part of a releasable fastener that includes a substrate portion supporting a distributed mechanical fastener across its surface, the substrate portion being flexible but substantially non-stretchable, the substrate portion being divided into multiple areas by at least one slit or at least one slot, such that the substrate may substantially conform to an underlying compound curved surface by independent bending of different divided portions of the substrate.

In one embodiment, the substrate portion includes a plurality of slits or slots or both which together divide the substrate portion into a serpentine body.

In one embodiment, the patient interface comprises one or more hinges that are predisposed to bend in predefined directions; wherein the one or more hinges are configured to stabilise a position of the one or more prongs on a patient's face when forces are exerted on the nasal interface.

In one embodiment, at least one of the one or more hinges is located adjacent to the one or more prongs at a location that is spaced laterally and outwardly in relation to the one or more prongs.

In one embodiment, at least one of the one or more hinges is predisposed to bend in a pre-defined direction.

In one embodiment, at least one of the one or more hinges is configured to bend in, either or both of, the following directions: inward towards the patient's face, downwards from the patient's nose.

In one embodiment, the one or more hinges comprise a variable cross-sectional area or a variable thickness.

In one embodiment, the one or more hinges comprises an elastic hinge that is configured to be pre-stressed before application to a patient.

In one embodiment, the patient interface further comprises one or more hinging regions forming a bend in the body, wherein each of the one or more hinging regions is configured to bend when a force is applied to the nasal interface and to stabilize a position of the at least one nasal prong on a portion of the face of the patient in order to reduce the displacement distance of the at least one nasal prong out of a nare of the patient.

In one embodiment, the one or more hinging regions is located adjacent to the one or more prongs at a location that is spaced laterally and outwardly in relation to the one or more prongs.

In one embodiment, the one or more hinging regions comprises two hinging regions.

In one embodiment, the patient interface comprises two prongs and wherein a first hinging region is located adjacent to a first prong at a location that is spaced laterally and outwardly in relation to a first prong and a second hinging region is located adjacent to the second prong at a location that is spaced laterally and outwardly in relation to the second prong.

In one embodiment, the securement system comprises a fixation structure for securing a patient interface tube on a patient's face, the fixation structure comprising: a fixation structure body comprising at least one separable extension and opposed first and second regions, the first region comprising an adhesive to adhere to the patient's face, wherein the at least one separable extension is adapted to secure a tube.

In one embodiment, the at least one separable extension comprises a weakened section.

In one embodiment, the at least one separable extension is attached to the fixation structure body via a perforated section.

In one embodiment, the at least one separable extension comprises a first portion adapted to secure the tube and a second portion adapted to secure the patient interface.

In one embodiment, the first portion of the at least one separable extension comprises an adhesive layer to adhere to the tube.

In one embodiment, the second portion of the at least one separable extension comprises a first fastener to attach to a complementary second fastener of the patient interface.

In one embodiment, the at least one separable extension comprises a pair of separable extensions.

In one embodiment, the fixation structure body comprises a first edge facing towards the patient's nose or mouth in use, a second edge facing away from the patient's nose or mouth in use, and opposed third and fourth edges extending between the first and second edges, wherein the pair of separable extensions are attached to the third and fourth edges of the fixation structure body via perforated sections.

In one embodiment, the fixation structure body comprises a first edge facing towards the patient's nose or mouth in use and a second edge facing towards the patient's nose or mouth in use, wherein the pair of separable extensions are attached to the first and second edges of the fixation structure body via perforated sections.

In one embodiment, the securement system comprises a fixation structure configured to fix a patient interface upon a patient, the fixation structure comprising: a fixation structure body, the fixation structure body comprising: first and second regions, the first region configured to contact a portion of a patient's face and the second region configured to face outward from the patient's face; and first and second extensions, the first and second extensions being pivotably attached to the fixation structure body, the first extension being separable from the fixation structure body, wherein the second extension is configured to pivot relative to the fixation structure body and to secure a tube to the fixation structure body.

In one embodiment, the first extension is configured to be separated from the fixation structure body and positioned on another portion of the patient's face.

In one embodiment, the second extension comprises a first region adapted to secure the tube and a second region adapted to secure the patient interface.

In one embodiment, the first region of the first extension comprises an adhesive layer.

In one embodiment, the adhesive layer is adapted to adhere to the tube and/or the fixation structure body.

In one embodiment, the second region of the second extension comprises a first fastener adapted to attach to a complementary second fastener of the patient interface.

In one embodiment, the first and second extensions comprises a pair of substantially opposed separable extensions.

In one embodiment, the fixation structure body comprises a first edge adapted to face towards the patient's nose or mouth, a second edge adapted to face away from the patient's nose or mouth, and opposed third and fourth edges extending between the first and second edges, wherein the pair of separable extensions are attached to the third and fourth edges of the fixation structure body via perforated sections.

In one embodiment, the fixation structure body comprises a first edge adapted to face towards the patient's nose or mouth and a second edge adapted to face away from the patient's nose or mouth, wherein the pair of separable extensions are attached to the first and second edges of the fixation structure body via perforated sections.

In one embodiment, the first patch is a dermal patch configured to attach or adhere to a user's face.

In one embodiment, the dermal patch is configured to attach or adhere to a user's face adjacent the user's upper lip and/or cheek.

In one embodiment, the first patch is attached to, or attachable to, an item being worn by the user.

In one embodiment, the item is part of a securement system.

In one embodiment, the item is a bonnet, or a headgear strap, including a strap that extends down the side of the patient's cheek like side burns, or chin strap.

In one embodiment, the sealing surface is configured to seal with the nasal valve of the user's nose.

In one embodiment, the sealing surface is configured to seal between the user's nare entry and the nasal valve.

In one embodiment, the sealing surface comprises a tapered surface with a cross-section of the sealing surface near the gas inlet being larger than a cross-section of the sealing surface of the prong near the gas outlet.

In one embodiment, the at least one nasal prong terminates at or proximate the nasal valve.

In one embodiment, the exterior surface of the at least one nasal prong has an elbow portion.

In one embodiment, the at least one nasal prong has an external cross-section that varies along the length of the at least one nasal prong.

In one embodiment, the at least one nasal prong is tapered with a cross-section of the exterior surface of the prong near the gas inlet being larger than a cross-section of the exterior surface of the prong near the gas outlet.

In one embodiment, the lumen of the at least one nasal prong has an internal cross-section that varies along the length of the at least one nasal prong.

In one embodiment, the nasal prong is shaped to avoid contact with the septum of a user at the base of a user's nose.

In one embodiment, the nasal prong is shaped to substantially align the flow of breathing gas through the gas outlet with a user's upper airways.

In one embodiment, the nasal prong is shaped to extend generally upwardly and rearwardly into a user's nares, the nasal prong having a curvature that includes at least two inflection points.

In one embodiment, the nasal prong defines a lumen that extends between the gas inlet and the gas outlet, the shape of the lumen changing from generally oval at the gas inlet to generally elliptical at the gas outlet.

In one embodiment, the nasal prong defines a lumen that extends between the gas inlet and the gas outlet, the shape of the lumen changing from generally kidney-bean shaped at the gas inlet to generally elliptical at the gas outlet.

In one embodiment, the prong is shaped to maximize the cross-sectional area of the lumen.

In one embodiment, the patient interface comprises two nasal prongs spaced symmetrically about a user's sagittal plane, the prongs extending inwardly towards the user's sagittal plane below the user's nose from a base on a common support disposed along a user's upper lip.

In one embodiment, the prongs extend from the body toward the user's septum and curve around the corners of a user's nostrils upwardly and rearwardly into the user's nares, each prong extending along a generally inclined posterior trajectory and passing through two mediolateral points of inflection that orientate the gas outlet with respect to the user's upper airway passages.

In one embodiment, the at least one prong has a shaped trajectory fitting the anatomical shape of the user's nostril.

In one embodiment, in a first portion (or phase) of the at least one prong, the trajectory moves horizontally towards the midline of the face, in a second portion (or phase) of the prong, the trajectory curves upwards directly into the nostril towards the crown of the head, in a third portion (or phase) of the prong, the trajectory rolls backwards into the head following the anatomical curvature of the nostril, and in a fourth portion (or phase), the trajectory tilts horizontally towards the centre of the patient interface to align the flow outlet with the user's upper airway.

In one embodiment, the at least one prong has a cross-section that varies along the central trajectory.

In one embodiment, the cross-sectional diameter generally decreases along the trajectory from the first portion (or phase) to the end of the fourth portion (or phase).

In one embodiment, the securement system further comprises a bonnet.

In one embodiment, the securement system further comprises at least one headgear strap that extend down the side of the patient's cheek.

In one embodiment, the securement system further comprises a chin strap.

In one embodiment, the chin strap attachable to the bonnet.

In one embodiment, the chin strap comprises hook and/or loop material.

In one embodiment, the at least one headgear strap that extends down the side of the patient's cheek is attachable to the bonnet.

In one embodiment, the at least one headgear strap that extends down the side of the patient's cheek comprises hook and/or loop material.

In one embodiment, the securement system further comprises at least one fastener.

In one embodiment, the at least one fastener is a tube clip.

In one embodiment, the at least one fastener is a sleeve.

In one embodiment, patient interface assembly further comprises a tube management and retention system including a device configured to be removably attached to the tube and removably attached to any item in proximity to, or attached to, the patient.

In one embodiment, the item is headgear, a chin strap, a bonnet, clothing, or bedsheets.

In one embodiment, the headgear comprises at least one headgear strap that extends down the side of the patient's face and cheek.

In one embodiment, the chin strap is attachable to a bonnet.

In one embodiment, the chin strap comprises hook and/or loop material.

In one embodiment, the at least one headgear strap that extends down the side of the patient's cheek is attachable to a bonnet.

In one embodiment, the at least one headgear strap that extends down the side of the patient's cheek comprises hook and/or loop material.

In one embodiment, the device comprises at least one fastener.

In one embodiment, the fastener is a sleeve.

In one embodiment, patient interface assembly further comprises a tube management and retention system including one or more pillows.

In one embodiment, the patient interface assembly further comprises a tube management system including a device configured to be removably attached to the tube and primarily and/or permanently attached to any item in proximity to, or attached to, the patient.

In one embodiment, the item is headgear, chin strap, bonnet, clothing, or bedsheets.

In one embodiment, the headgear comprises at least one headgear strap that extend down the side of the patient's cheek (like side burns).

In one embodiment, the chin strap is attachable to a bonnet.

In one embodiment, the chin strap comprises hook and/or loop material.

In one embodiment, the at least one headgear strap that extends down the side of the patient's cheek is attachable to a bonnet.

In one embodiment, the at least one headgear strap that extends down the side of the patient's cheek comprises hook and/or loop material.

In one embodiment, the patient interface is configured to receive an inspiratory flow of gases via an inspiratory conduit.

In one embodiment, the patient interface is configured to direct a flow of the expiratory gases to an expiratory conduit.

In one embodiment, the inspiratory conduit and/or the expiratory conduit is a medical tube to transport gases.

In one embodiment, the medical tube comprises: an elongate film spirally wrapped with an elongate reinforcing member to form a lumen, the elongate film bonding with the elongate reinforcing member, wherein the elongate film comprises a profile that keeps the elongate film from protruding into the lumen of the medical tube when the medical tube is bent.

In one embodiment, the elongate film is made of a breathable material.

In one embodiment, the elongate film is wrapped around a radially-outward surface of the elongate reinforcing member, facing away from the lumen, such that the elongate reinforcing member interacts with the lumen of the medical tube and the elongate film forms the outer surface of the medical tube.

In one embodiment, the longitudinal distance between corresponding points on adjacent windings of the elongate reinforcing member, measured when the medical tube is not subject to deformational strain, is selected such that the elongate film drapes a maximal amount between successive windings of the elongate reinforcing member while not extending inwardly beyond the elongate reinforcing member base into the lumen when the medical tube is bent.

In one embodiment, the average radial distance from the lowest point of the elongate film in the lumen to the bottom of the elongate reinforcing member, measured when the medical tube is not subject to deformational strain, is less than 0.2 mm.

In one embodiment, the profile is an inwardly biased profile.

In one embodiment, the elongate reinforcing member comprises a circular cross-section.

In one embodiment, windings of the elongate reinforcing member roll or lean sideways in response to an applied force.

In one embodiment, the medical tube maintains a gases flow while the force is applied.

In one embodiment, a maximal amount of the elongate film extends between adjacent windings of the elongate reinforcing member without protruding into the lumen.

In one embodiment, the elongate reinforcing member is hollow.

In one embodiment, the elongate reinforcing member comprises a cavity configured to hold or transport a fluid.

In one embodiment, the elongate film is made of a breathable material.

In one embodiment, the elongate film is wrapped around a radially-outward surface of the elongate reinforcing member, facing away from the lumen, such that the elongate reinforcing member interacts with the lumen of the medical tube and the elongate film forms the outer surface of the medical tube.

In one embodiment, the average radial distance from the lowest point of the elongate film in the lumen to the bottom of the elongate reinforcing member, measured when the medical tube is not subject to deformational strain, is less than 0.2 mm.

In one embodiment, the profile is an inwardly biased profile.

In one embodiment, windings of the elongate reinforcing member roll or lean sideways in response to an applied force.

In one embodiment, the medical tube maintains a gases flow while the force is applied.

In one embodiment, the elongate reinforcing member is hollow.

In one embodiment, the elongate reinforcing member comprises a cavity configured to hold or transport a fluid.

In another aspect, the disclosure broadly consists in a patient interface assembly comprising: a patient interface comprising: a body and at least one nasal prong extending from the body, the at least one nasal prong having a gas inlet for fluid communication with a supply of breathable gas, and a gas outlet configured to direct a flow of gas towards a nare of the user's nose, the at least one nasal prong further including an exterior surface, at least a portion of the exterior surface is a sealing surface configured to seal the nare of the user's nose; and one or more hinges that are predisposed to bend in predefined directions; wherein the one or more hinges are configured to stabilise a position of the one or more prongs on a patient's face when forces are exerted on the nasal interface.

In one embodiment, each prong is an inspiratory and expiratory prong.

In one embodiment, each of the prongs is in fluid communication with the other of the prongs via a manifold.

In one embodiment, the manifold is fully and always open between the prongs.

In one embodiment, at least one of the one or more hinges is located adjacent to the one or more prongs at a location that is spaced laterally and outwardly in relation to the one or more prongs.

In one embodiment, at least one of the one or more hinges is predisposed to bend in a pre-defined direction.

In one embodiment, at least one of the one or more hinges is configured to bend in, either or both of, the following directions: inward towards the patient's face, downwards from the patient's nose.

In one embodiment, the one or more hinges comprise a variable cross-sectional area or a variable thickness.

In one embodiment, the one or more hinges comprises an elastic hinge that is configured to be pre-stressed before application to a patient.

In one embodiment, the patient interface assembly further comprises a securement system for the patient interface and/or patient interface tubing, the securement system comprising a two-part releasable attachment or connection arrangement, the arrangement comprising a first patch and a second patch.

In one embodiment:
the first patch has a patient side and an interface side, the patient side of the first patch being attachable to the skin of a user, (such as for example by an adhesive, generally being of a dermatologically sensitive adhesive such as a hydrocolloid) or being attachable to an item being worn by the user, the interface side of the first patch being provided with the first part of a two-part releasable attachment or connection system,
the second patch having an interface side and patient side, the patient side of the second patch being provided with the complimentary second part of the two-part releasable attachment or connection system, and
the interface side of the second patch being attachable or connected to the patient interface and/or associated patient interface tubing, for example by adhesive or may be formed as a part of the patient interface or may be provided as a back surface of the patient interface upon which is provided the second part of the two-part system.

In one embodiment, the interface side of the first patch has one of a hook or a loop, and the second part of the second patch has the other of the hook or loop, such that the first and second parts (and patches) are releasably attachable or connectable to each other.

In one embodiment, the first patch is locatable and/or attachable to the skin of a user's face.

In one embodiment, the second patch is locatable, or attached or attachable, or is connected to, or with, a patient interface.

In one embodiment, the second patch is formed integrally with, or forms a part of, a patient interface.

In one embodiment, the first part of the two-part releasable attachment or connection system on the first patch occupies less than about 90%, or about 85%, or about 75%, or about 60% or about 50% or about 40% or about 30% or about 20% or about 10% of the interface side of the first patch.

In one embodiment, the first part of the two-part releasable attachment or connection system is adhered or adherable to the patient interface side of the first patch with a suitable adhesive.

In one embodiment, the user side of the first patch has a dermatologically sensitive adhesive (such as a hydrocolloid for example) that attaches or adheres the first patch to a user's skin.

In one embodiment, the first patch has a surface of sufficient area such that, the surface distributes pressure the attachment or adhering forces across the user's skin.

In one embodiment, the first patch is configured to attach or adhere to a user's face.

In one embodiment, the first patch is configured to attach or adhere to a user's face adjacent the user's upper lip and/or cheek.

In one embodiment, the securement system is configured to receive and/or secure a nasal cannula and associated tubing, the tubing extending from one or both sides of a user's face.

In one embodiment, the securement system is configured for use with an infant or neonatal infant.

In one embodiment, the patient interface assembly further comprises a securement patch configured to be applied or applicable over the patient interface and affixed or affixable to the first patch to provide additional securement.

In one embodiment, the first part of the two-part releasable attachment or connection system includes a substrate portion secured to, or for securing to, the first patch.

In one embodiment, the substrate portion includes at least one slit or at least one slot with areas of the substrate portion separated by the slit or slot.

In one embodiment, the substrate portion includes a plurality of slits or slots or both which together divide the substrate portion into a serpentine body.

In one embodiment, the slits and/or slots are arranged in the substrate such that a first set of at least one set of slits or slots extends into the substrate from one edge of the substrate and a second set of slits or slots extends into the substrate from the other edge of the substrate, the slits or slots of a set being interleaved with the slits or slots of the other set such that a path along the substrate portion from one end to another end without crossing the slits or slots must follow a zigzag or serpentine path much longer than a direct line between the ends.

In one embodiment, a slit or slot of the plurality of slits or slots is curved.

In one embodiment, a plurality of the slits or slots is curved and the curved slits or slots are arranged substantially parallel.

In one embodiment, the slits or slots are arranged in a herring bone pattern extending in from the edges of the substrate portion.

In one embodiment, the substrate is divided into separated portions by a serpentine slit or slot.

In one embodiment, the substrate portion is divided into portions by a spiral slit or slot.

In one embodiment, the substrate portion is divided into sub-portions by slits or slots arranged on substantially concentric circles.

In one embodiment, the concentric circles are centred at approximately the centre of the substrate portion.

In one embodiment, the slit or slots divide the substrate portion into a plurality of islands, each joined to an adjacent island or islands by a narrow bridge.

In one embodiment, the substrate portion is divided into portions by an S-shaped slit.

In one embodiment, the substrate portion is divided into portions by a T-shaped slit.

In one embodiment, the substrate portion covers at least 70% of the area of the first patch.

In one embodiment, for a boundary defining the shortest path around the perimeter of the substrate, the substrate portion covers at least 80% of the area within the boundary.

In one embodiment, there is provided a part of a releasable fastener that includes a substrate portion supporting a distributed mechanical fastener across its surface, the substrate portion being flexible but substantially non-stretchable, the substrate portion being divided into multiple areas by at least one slit or at least one slot, such that the substrate may substantially conform to an underlying compound curved surface by independent bending of different divided portions of the substrate.

In one embodiment, the substrate portion includes a plurality of slits or slots or both which together divide the substrate portion into a serpentine body.

In one embodiment, the securement system comprises a fixation structure for securing a patient interface tube on a patient's face, the fixation structure comprising:

a fixation structure body comprising at least one separable extension and opposed first and second regions, the first region comprising an adhesive to adhere to the patient's face, wherein the at least one separable extension is adapted to secure a tube.

In one embodiment, the at least one separable extension comprises a weakened section.

In one embodiment, the at least one separable extension is attached to the fixation structure body via a perforated section.

In one embodiment, the at least one separable extension comprises a first portion adapted to secure the tube and a second portion adapted to secure the patient interface.

In one embodiment, the first portion of the at least one separable extension comprises an adhesive layer to adhere to the tube.

In one embodiment, the second portion of the at least one separable extension comprises a first fastener to attach to a complementary second fastener of the patient interface.

In one embodiment, the at least one separable extension comprises a pair of separable extensions.

In one embodiment, the fixation structure body comprises a first edge facing towards the patient's nose or mouth in use, a second edge facing away from the patient's nose or mouth in use, and opposed third and fourth edges extending between the first and second edges, wherein the pair of separable extensions are attached to the third and fourth edges of the fixation structure body via perforated sections.

In one embodiment, the fixation structure body comprises a first edge facing towards the patient's nose or mouth in use and a second edge facing towards the patient's nose or mouth in use, wherein the pair of separable extensions are attached to the first and second edges of the fixation structure body via perforated sections.

In one embodiment, the securement system comprises a fixation structure configured to fix a patient interface upon a patient, the fixation structure comprising: a fixation structure body, the fixation structure body comprising: first and second regions, the first region configured to contact a portion of a patient's face and the second region configured to face outward from the patient's face; and first and second extensions, the first and second extensions being pivotably attached to the fixation structure body, the first extension being separable from the fixation structure body, wherein the second extension is configured to pivot relative to the fixation structure body and to secure a tube to the fixation structure body.

In one embodiment, the first extension is configured to be separated from the fixation structure body and positioned on another portion of the patient's face.

In one embodiment, the second extension comprises a first region adapted to secure the tube and a second region adapted to secure the patient interface.

In one embodiment, the first region of the first extension comprises an adhesive layer.

In one embodiment, the adhesive layer is adapted to adhere to the tube and/or the fixation structure body.

In one embodiment, the second region of the second extension comprises a first fastener adapted to attach to a complementary second fastener of the patient interface.

In one embodiment, the first and second extensions comprises a pair of substantially opposed separable extensions.

In one embodiment, the fixation structure body comprises a first edge adapted to face towards the patient's nose or mouth, a second edge adapted to face away from the patient's nose or mouth, and opposed third and fourth edges extending between the first and second edges, wherein the pair of separable extensions are attached to the third and fourth edges of the fixation structure body via perforated sections.

In one embodiment, the fixation structure body comprises a first edge adapted to face towards the patient's nose or mouth and a second edge adapted to face away from the patient's nose or mouth, wherein the pair of separable extensions are attached to the first and second edges of the fixation structure body via perforated sections.

In one embodiment, the first patch is a dermal patch configured to attach or adhere to a user's face.

In one embodiment, the dermal patch is configured to attach or adhere to a user's face adjacent the user's upper lip and/or cheek.

In one embodiment, the first patch is attached to, or attachable to, an item being worn by the user.

In one embodiment, the item is part of a securement system.

In one embodiment, the item is a bonnet, or a headgear strap, including a strap that extends down the side of the patient's cheek like side burns, or chin strap.

In one embodiment, the sealing surface is configured to seal with the nasal valve of the user's nose.

In one embodiment, the sealing surface is configured to seal between the user's nare entry and the nasal valve.

In one embodiment, the sealing surface comprises a tapered surface with a cross-section of the sealing surface near the gas inlet being larger than a cross-section of the sealing surface of the prong near the gas outlet.

In one embodiment, the at least one nasal prong terminates at or proximate the nasal valve.

In one embodiment, the exterior surface of the at least one nasal prong has an elbow portion.

In one embodiment, the at least one nasal prong has an external cross-section that varies along the length of the at least one nasal prong.

In one embodiment, the at least one nasal prong is tapered with a cross-section of the exterior surface of the prong near the gas inlet being larger than a cross-section of the exterior surface of the prong near the gas outlet.

In one embodiment, the lumen of the at least one nasal prong has an internal cross-section that varies along the length of the at least one nasal prong.

In one embodiment, the nasal prong is shaped to avoid contact with the septum of a user at the base of a user's nose.

In one embodiment, the nasal prong is shaped to substantially align the flow of breathing gas through the gas outlet with a user's upper airways.

In one embodiment, the nasal prong is shaped to extend generally upwardly and rearwardly into a user's nares, the nasal prong having a curvature that includes at least two inflection points.

In one embodiment, the nasal prong defines a lumen that extends between the gas inlet and the gas outlet, the shape of the lumen changing from generally oval at the gas inlet to generally elliptical at the gas outlet.

In one embodiment, the nasal prong defines a lumen that extends between the gas inlet and the gas outlet, the shape of the lumen changing from generally kidney-bean shaped at the gas inlet to generally elliptical at the gas outlet.

In one embodiment, the prong is shaped to maximize the cross-sectional area of the lumen.

In one embodiment, the patient interface comprises two nasal prongs spaced symmetrically about a user's sagittal plane, the prongs extending inwardly towards the user's sagittal plane below the user's nose from a base on a common support disposed along a user's upper lip.

In one embodiment, the prongs extend from the body toward the user's septum and curve around the corners of a user's nostrils upwardly and rearwardly into the user's nares, each prong extending along a generally inclined posterior trajectory and passing through two mediolateral points of inflection that orientate the gas outlet with respect to the user's upper airway passages.

In one embodiment, the at least one prong has a shaped trajectory fitting the anatomical shape of the user's nostril.

In one embodiment, in a first portion (or phase) of the at least one prong, the trajectory moves horizontally towards the midline of the face, in a second portion (or phase) of the prong, the trajectory curves upwards directly into the nostril towards the crown of the head, in a third portion (or phase) of the prong, the trajectory rolls backwards into the head following the anatomical curvature of the nostril, and in a fourth portion (or phase), the trajectory tilts horizontally towards the centre of the patient interface to align the flow outlet with the user's upper airway.

In one embodiment, the at least one prong has a cross-section that varies along the central trajectory.

In one embodiment, the cross-sectional diameter generally decreases along the trajectory from the first portion (or phase) to the end of the fourth portion (or phase).

In one embodiment, the securement system further comprises a bonnet.

In one embodiment, the securement system further comprises at least one headgear strap that extend down the side of the patient's cheek.

In one embodiment, the securement system further comprises a chin strap.

In one embodiment, the chin strap attachable to the bonnet.

In one embodiment, the chin strap comprises hook and/or loop material.

In one embodiment, the at least one headgear strap that extends down the side of the patient's cheek is attachable to the bonnet.

In one embodiment, the at least one headgear strap that extends down the side of the patient's cheek comprises hook and/or loop material.

In one embodiment, the securement system further comprises at least one fastener.

In one embodiment, the at least one fastener is a tube clip.

In one embodiment, the at least one fastener is a sleeve.

In one embodiment, patient interface assembly further comprises a tube management and retention system including a device configured to be removably attached to the tube and removably attached to any item in proximity to, or attached to, the patient.

In one embodiment, the item is headgear, a chin strap, a bonnet, clothing, or bedsheets.

In one embodiment, the headgear comprises at least one headgear strap that extends down the side of the patient's face and cheek.

In one embodiment, the chin strap is attachable to a bonnet.

In one embodiment, the chin strap comprises hook and/or loop material.

In one embodiment, the at least one headgear strap that extends down the side of the patient's cheek is attachable to a bonnet.

In one embodiment, the at least one headgear strap that extends down the side of the patient's cheek comprises hook and/or loop material.

In one embodiment, the device comprises at least one fastener.

In one embodiment, the fastener is a sleeve.

In one embodiment, patient interface assembly further comprises a tube management and retention system including one or more pillows.

In one embodiment, the patient interface assembly further comprises a tube management system including a device configured to be removably attached to the tube and primarily and/or permanently attached to any item in proximity to, or attached to, the patient.

In one embodiment, the item is headgear, chin strap, bonnet, clothing, or bedsheets.

In one embodiment, the headgear comprises at least one headgear strap that extend down the side of the patient's cheek (like side burns).

In one embodiment, the chin strap is attachable to a bonnet.

In one embodiment, the chin strap comprises hook and/or loop material.

In one embodiment, the at least one headgear strap that extends down the side of the patient's cheek is attachable to a bonnet.

In one embodiment, the at least one headgear strap that extends down the side of the patient's cheek comprises hook and/or loop material.

In one embodiment, the patient interface is configured to receive an inspiratory flow of gases via an inspiratory conduit.

In one embodiment, the patient interface is configured to direct a flow of the expiratory gases to an expiratory conduit.

In one embodiment, the inspiratory conduit and/or the expiratory conduit is a medical tube to transport gases.

In one embodiment, the medical tube comprises:
an elongate film spirally wrapped with an elongate reinforcing member to form a lumen, the elongate film bonding with the elongate reinforcing member,
wherein the elongate film comprises a profile that keeps the elongate film from protruding into the lumen of the medical tube when the medical tube is bent.

In one embodiment, the elongate film is made of a breathable material.

In one embodiment, the elongate film is wrapped around a radially-outward surface of the elongate reinforcing member, facing away from the lumen, such that the elongate reinforcing member interacts with the lumen of the medical tube and the elongate film forms the outer surface of the medical tube.

In one embodiment, the longitudinal distance between corresponding points on adjacent windings of the elongate reinforcing member, measured when the medical tube is not subject to deformational strain, is selected such that the elongate film drapes a maximal amount between successive windings of the elongate reinforcing member while not extending inwardly beyond the elongate reinforcing member base into the lumen when the medical tube is bent.

In one embodiment, the average radial distance from the lowest point of the elongate film in the lumen to the bottom of the elongate reinforcing member, measured when the medical tube is not subject to deformational strain, is less than 0.2 mm.

In one embodiment, the profile is an inwardly biased profile.

In one embodiment, the elongate reinforcing member comprises a circular cross-section.

In one embodiment, windings of the elongate reinforcing member roll or lean sideways in response to an applied force.

In one embodiment, the medical tube maintains a gases flow while the force is applied.

In one embodiment, a maximal amount of the elongate film extends between adjacent windings of the elongate reinforcing member without protruding into the lumen.

In one embodiment, the elongate reinforcing member is hollow.

In one embodiment, the elongate reinforcing member comprises a cavity configured to hold or transport a fluid.

In one embodiment, the elongate film is made of a breathable material.

In one embodiment, the elongate film is wrapped around a radially-outward surface of the elongate reinforcing member, facing away from the lumen, such that the elongate reinforcing member interacts with the lumen of the medical tube and the elongate film forms the outer surface of the medical tube.

In one embodiment, the average radial distance from the lowest point of the elongate film in the lumen to the bottom of the elongate reinforcing member, measured when the medical tube is not subject to deformational strain, is less than 0.2 mm.

In one embodiment, the profile is an inwardly biased profile.

In one embodiment, windings of the elongate reinforcing member roll or lean sideways in response to an applied force.

In one embodiment, the medical tube maintains a gases flow while the force is applied.

In one embodiment, the elongate reinforcing member is hollow.

In one embodiment, the elongate reinforcing member comprises a cavity configured to hold or transport a fluid.

In another aspect, the disclosure broadly consists in a patient interface comprising: a body and at least one nasal prong extending from the body, the at least one nasal prong having a gas inlet for fluid communication with a supply of breathable gas, and a gas outlet configured to direct a flow of gas towards a nare of the user's nose, the at least one nasal prong further including an exterior surface, at least a portion of the exterior surface is a sealing surface configured to seal with the nasal valve of the user's nose or between the user's nare entry and the nasal valve.

In one embodiment, the sealing surface comprises a tapered surface with a cross-section of the sealing surface near the gas inlet being larger than the cross-section of the sealing surface of the prong near the gas outlet.

In one embodiment, the at least one nasal prong terminates at or proximate the nasal valve.

In one embodiment, the exterior surface of the at least one nasal prong has an elbow portion.

In one embodiment, the at least one nasal prong has an external cross-section that varies along the length of the at least one nasal prong.

In one embodiment, the at least one nasal prong is tapered with the cross-section of the exterior surface of the prong near the gas inlet being larger than the cross-section of the exterior surface of the prong near the gas outlet.

In one embodiment, the lumen of the at least one nasal prong has an internal cross-section that varies along the length of the at least one nasal prong.

In one embodiment, the nasal prong is shaped to avoid contact with the septum of a user at the base of a user's nose.

In one embodiment, the nasal prong is shaped to substantially align the flow of breathing gas through the gas outlet with a user's upper airways.

In one embodiment, the nasal prong is shaped to extend generally upwardly and rearwardly into a user's nares, the nasal prong having a curvature that includes at least two inflection points.

In one embodiment, the nasal prong defines a lumen that extends between the gas inlet and the gas outlet, the shape of the lumen changing from generally oval at the gas inlet to generally elliptical at the gas outlet.

In one embodiment, the nasal prong defines a lumen that extends between the gas inlet and the gas outlet, the shape of the lumen changing from generally kidney-bean shaped at the gas inlet to generally elliptical at the gas outlet.

In one embodiment, the prong is shaped to maximize the cross-sectional area of the lumen.

In one embodiment, the patient interface comprises two nasal prongs spaced symmetrically about a user's sagittal plane, the prongs extending inwardly towards the user's sagittal plane below the user's nose from a base on a common support disposed along a user's upper lip.

In one embodiment, the prongs extend from the body toward the user's septum and curve around the corners of a user's nostrils upwardly and rearwardly into the user's nares, each prong extending along a generally inclined posterior trajectory and passing through two mediolateral points of inflection that orientate the gas outlet with respect to the user's upper airway passages.

In one embodiment, the at least one prong has a shaped trajectory fitting the anatomical shape of the user's nostril.

In one embodiment, in a first portion (or phase) of the at least one prong, the trajectory moves horizontally towards the midline of the face, in a second portion (or phase) of the prong, the trajectory curves upwards directly into the nostril towards the crown of the head, in a third portion (or phase) of the prong, the trajectory rolls backwards into the head following the anatomical curvature of the nostril, and in a fourth portion (or phase), the trajectory tilts horizontally towards the centre of the patient interface to align the flow outlet with the user's upper airway.

In one embodiment, the at least one prong has a cross-section that varies along the central trajectory.

In one embodiment, the cross-sectional diameter generally decreases along the trajectory from the first portion (or phase) to the end of the fourth portion (or phase).

In one embodiment, the patient interface further comprises a contoured backing or facial pad configured to rest on a user's face.

In one embodiment, the backing or facial pad is preformed to be of a contour that is substantially curved to fit a user's face or upper lip region.

In one embodiment, the patient interface is a nasal cannula.

In one embodiment, the sealing surface is configured to seal with the nasal valve of the user's nose.

In one embodiment, the sealing surface is configured to seal between the user's nare entry and the nasal valve.

In one embodiment, the sealing surface comprises a tapered surface with a cross-section of the sealing surface near the gas inlet being larger than a cross-section of the sealing surface of the prong near the gas outlet.

In one embodiment, the at least one nasal prong terminates at or proximate the nasal valve.

In one embodiment, the exterior surface of the at least one nasal prong has an elbow portion.

In one embodiment, the at least one nasal prong has an external cross-section that varies along the length of the at least one nasal prong.

In one embodiment, the at least one nasal prong is tapered with a cross-section of the exterior surface of the prong near the gas inlet being larger than a cross-section of the exterior surface of the prong near the gas outlet.

In one embodiment, the lumen of the at least one nasal prong has an internal cross-section that varies along the length of the at least one nasal prong.

In one embodiment, the nasal prong is shaped to avoid contact with the septum of a user at the base of a user's nose.

In one embodiment, the nasal prong is shaped to substantially align the flow of breathing gas through the gas outlet with a user's upper airways.

In one embodiment, the nasal prong is shaped to extend generally upwardly and rearwardly into a user's nares, the nasal prong having a curvature that includes at least two inflection points.

In one embodiment, the nasal prong defines a lumen that extends between the gas inlet and the gas outlet, the shape of the lumen changing from generally oval at the gas inlet to generally elliptical at the gas outlet.

In one embodiment, the nasal prong defines a lumen that extends between the gas inlet and the gas outlet, the shape of the lumen changing from generally kidney-bean shaped at the gas inlet to generally elliptical at the gas outlet.

In one embodiment, the prong is shaped to maximize the cross-sectional area of the lumen.

In one embodiment, the patient interface comprises two nasal prongs spaced symmetrically about a user's sagittal plane, the prongs extending inwardly towards the user's sagittal plane below the user's nose from a base on a common support disposed along a user's upper lip.

In one embodiment, the prongs extend from the body toward the user's septum and curve around the corners of a user's nostrils upwardly and rearwardly into the user's nares, each prong extending along a generally inclined posterior trajectory and passing through two mediolateral points of inflection that orientate the gas outlet with respect to the user's upper airway passages.

In one embodiment, the at least one prong has a shaped trajectory fitting the anatomical shape of the user's nostril.

In one embodiment, in a first portion (or phase) of the at least one prong, the trajectory moves horizontally towards the midline of the face, in a second portion (or phase) of the prong, the trajectory curves upwards directly into the nostril towards the crown of the head, in a third portion (or phase) of the prong, the trajectory rolls backwards into the head following the anatomical curvature of the nostril, and in a fourth portion (or phase), the trajectory tilts horizontally towards the centre of the patient interface to align the flow outlet with the user's upper airway.

In one embodiment, the at least one prong has a cross-section that varies along the central trajectory.

In one embodiment, the cross-sectional diameter generally decreases along the trajectory from the first portion (or phase) to the end of the fourth portion (or phase).

In one embodiment, the securement system further comprises a bonnet.

In one embodiment, the securement system further comprises at least one headgear strap that extend down the side of the patient's cheek.

In one embodiment, the securement system further comprises a chin strap.

In one embodiment, the chin strap attachable to the bonnet.

In one embodiment, the chin strap comprises hook and/or loop material.

In one embodiment, the at least one headgear strap that extends down the side of the patient's cheek is attachable to the bonnet.

In one embodiment, the at least one headgear strap that extends down the side of the patient's cheek comprises hook and/or loop material.

In one embodiment, the securement system further comprises at least one fastener.

In one embodiment, the at least one fastener is a tube clip.

In one embodiment, the at least one fastener is a sleeve.

In one embodiment, patient interface assembly further comprises a tube management and retention system including a device configured to be removably attached to the tube and removably attached to any item in proximity to, or attached to, the patient.

In one embodiment, the item is headgear, a chin strap, a bonnet, clothing, or bedsheets.

In one embodiment, the headgear comprises at least one headgear strap that extends down the side of the patient's face and cheek.

In one embodiment, the chin strap is attachable to a bonnet.

In one embodiment, the chin strap comprises hook and/or loop material.

In one embodiment, the at least one headgear strap that extends down the side of the patient's cheek is attachable to a bonnet.

In one embodiment, the at least one headgear strap that extends down the side of the patient's cheek comprises hook and/or loop material.

In one embodiment, the device comprises at least one fastener.

In one embodiment, the fastener is a sleeve.

In one embodiment, patient interface assembly further comprises a tube management and retention system including one or more pillows.

In one embodiment, the patient interface assembly further comprises a tube management system including a device configured to be removably attached to the tube and primarily and/or permanently attached to any item in proximity to, or attached to, the patient.

In one embodiment, the item is headgear, chin strap, bonnet, clothing, or bedsheets.

In one embodiment, the headgear comprises at least one headgear strap that extend down the side of the patient's cheek (like side burns).

In one embodiment, the chin strap is attachable to a bonnet.

In one embodiment, the chin strap comprises hook and/or loop material.

In one embodiment, the at least one headgear strap that extends down the side of the patient's cheek is attachable to a bonnet.

In one embodiment, the at least one headgear strap that extends down the side of the patient's cheek comprises hook and/or loop material.

In one embodiment, the patient interface is configured to receive an inspiratory flow of gases via an inspiratory conduit.

In one embodiment, the patient interface is configured to direct a flow of the expiratory gases to an expiratory conduit.

In one embodiment, the inspiratory conduit and/or the expiratory conduit is a medical tube to transport gases.

In one embodiment, the medical tube comprises: an elongate film spirally wrapped with an elongate reinforcing member to form a lumen, the elongate film bonding with the elongate reinforcing member, wherein the elongate film comprises a profile that keeps the elongate film from protruding into the lumen of the medical tube when the medical tube is bent.

In one embodiment, the elongate film is made of a breathable material.

In one embodiment, the elongate film is wrapped around a radially-outward surface of the elongate reinforcing member, facing away from the lumen, such that the elongate reinforcing member interacts with the lumen of the medical tube and the elongate film forms the outer surface of the medical tube.

In one embodiment, the longitudinal distance between corresponding points on adjacent windings of the elongate reinforcing member, measured when the medical tube is not subject to deformational strain, is selected such that the elongate film drapes a maximal amount between successive windings of the elongate reinforcing member while not extending inwardly beyond the elongate reinforcing member base into the lumen when the medical tube is bent.

In one embodiment, the average radial distance from the lowest point of the elongate film in the lumen to the bottom of the elongate reinforcing member, measured when the medical tube is not subject to deformational strain, is less than 0.2 mm.

In one embodiment, the profile is an inwardly biased profile.

In one embodiment, the elongate reinforcing member comprises a circular cross-section.

In one embodiment, windings of the elongate reinforcing member roll or lean sideways in response to an applied force.

In one embodiment, the medical tube maintains a gases flow while the force is applied.

In one embodiment, a maximal amount of the elongate film extends between adjacent windings of the elongate reinforcing member without protruding into the lumen.

In one embodiment, the elongate reinforcing member is hollow.

In one embodiment, the elongate reinforcing member comprises a cavity configured to hold or transport a fluid.

In one embodiment, the elongate film is made of a breathable material.

In one embodiment, the elongate film is wrapped around a radially-outward surface of the elongate reinforcing member, facing away from the lumen, such that the elongate reinforcing member interacts with the lumen of the medical tube and the elongate film forms the outer surface of the medical tube.

In one embodiment, the average radial distance from the lowest point of the elongate film in the lumen to the bottom of the elongate reinforcing member, measured when the medical tube is not subject to deformational strain, is less than 0.2 mm.

In one embodiment, the profile is an inwardly biased profile.

In one embodiment, windings of the elongate reinforcing member roll or lean sideways in response to an applied force.

In one embodiment, the medical tube maintains a gases flow while the force is applied.

In one embodiment, the elongate reinforcing member is hollow.

In one embodiment, the elongate reinforcing member comprises a cavity configured to hold or transport a fluid.

In another aspect, the disclosure broadly consists in a patient interface comprising: a body and at least one nasal prong extending from the body, the at least one nasal prong having a gas inlet for fluid communication with a supply of breathable gas, and a gas outlet configured to direct a flow of gas towards a nare of the user's nose, the at least one nasal prong further including an exterior surface, at least a portion of the exterior surface is a sealing surface configured to seal the nare of the user's nose.

In one embodiment, the sealing surface is configured to seal with the nasal valve of the user's nose.

In one embodiment, the sealing surface is configured to seal between the user's nare entry and the nasal valve.

In one embodiment, the at least one nasal prong terminates at or proximate the nasal valve.

In one embodiment, the sealing surface comprises a tapered surface with a cross-section of the sealing surface near the gas inlet being larger than the cross-section of the sealing surface of the prong near the gas outlet.

In one embodiment, the exterior surface of the at least one nasal prong has an elbow portion.

In one embodiment, the at least one nasal prong has an external cross-section that varies along the length of the at least one nasal prong.

In one embodiment, the at least one nasal prong is tapered with the cross-section of the exterior surface of the prong near the gas inlet being larger than the cross-section of the exterior surface of the prong near the gas outlet.

In one embodiment, the lumen of the at least one nasal prong has an internal cross-section that varies along the length of the at least one nasal prong.

In one embodiment, the nasal prong is shaped to avoid contact with the septum of a user at the base of a user's nose.

In one embodiment, the nasal prong is shaped to substantially align the flow of breathing gas through the gas outlet with a user's upper airways.

In one embodiment, the nasal prong is shaped to extend generally upwardly and rearwardly into a user's nares, the nasal prong having a curvature that includes at least two inflection points.

In one embodiment, the nasal prong defines a lumen that extends between the gas inlet and the gas outlet, the shape of the lumen changing from generally oval at the gas inlet to generally elliptical at the gas outlet.

In one embodiment, the nasal prong defines a lumen that extends between the gas inlet and the gas outlet, the shape of the lumen changing from generally kidney-bean shaped at the gas inlet to generally elliptical at the gas outlet.

In one embodiment, the nasal prong is shaped to maximize the cross-sectional area of the lumen.

In one embodiment, the patient interface comprises two nasal prongs spaced symmetrically about a user's sagittal plane, the prongs extending inwardly towards the user's sagittal plane below the user's nose from a base on a common support disposed along a user's upper lip.

In one embodiment, the prongs extend from the body toward the user's septum and curve around the corners of a user's nostrils upwardly and rearwardly into the user's nares, each prong extending along a generally inclined posterior trajectory and passing through two mediolateral points of inflection that orientate the gas outlet with respect to the user's upper airway passages.

In one embodiment, the at least one prong has a shaped trajectory fitting the anatomical shape of the user's nostril.

In one embodiment, in a first portion (or phase) of the at least one prong, the trajectory moves horizontally towards the midline of the face, in a second portion (or phase) of the prong, the trajectory curves upwards directly into the nostril towards the crown of the head, in a third portion (or phase) of the prong, the trajectory rolls backwards into the head following the anatomical curvature of the nostril, and in a fourth portion (or phase), the trajectory tilts horizontally towards the centre of the patient interface to align the flow outlet with the user's upper airway.

In one embodiment, the at least one prong has a cross-section that varies along the central trajectory.

In one embodiment, the cross-sectional diameter generally decreases along the trajectory from the first portion (or phase) to the end of the fourth portion (or phase).

In one embodiment, the patient interface further comprises a contoured backing or facial pad configured to rest on a user's face.

In one embodiment, the backing or facial pad is preformed to be of a contour that is substantially curved to fit a user's face or upper lip region.

In one embodiment, the patient interface is a nasal cannula.

In another aspect, the disclosure broadly consists in a patient interface comprising: a body defining a manifold, the manifold including a gas inlet for fluid communication with a supply of breathable gas, and a gas outlet for fluid communication with expired gas, two nasal prongs extending from the body, each nasal prong having a gas inlet for fluid communication with the manifold to receive the supply of breathable gas, and a gas outlet configured to direct a flow of gas towards a nare of the user's nose, the nasal prongs being in fluid communication with each other via the manifold, each nasal prong further including an exterior surface, at least a portion of the exterior surface is a sealing surface configured to seal the nare of the user's nose.

In one embodiment, the patient interface has a first opening and a second opening, and wherein: in a first configuration, the first opening is the gas inlet of the manifold and the second opening is the gas outlet of the manifold; and in a second configuration, the second opening is the gas inlet of the manifold and the first opening is the gas outlet of the manifold.

In one embodiment, the first opening and the second opening are in fluid communication with each other via the manifold.

In one embodiment, the manifold does not include a plurality of vent holes for patient exhalation.

In another aspect, the disclosure broadly consists in a patient interface comprising: a body and at least one nasal prong extending from the body, the at least one nasal prong having a gas inlet for fluid communication with a supply of breathable gas, and a gas outlet configured to direct a flow of gas towards a nare of the user's nose, wherein the at least one nasal prong has an inner wall and an outer wall, the inner wall being nearer the patient's septum in use and the outer wall being further away from the patient's septum in use, the inner wall having a thickness that is thinner than a thickness of the outer wall.

In one embodiment, the at least one nasal prong has a front wall extending between the inner wall and the outer wall, the inner wall having a thickness that is thinner than a thickness of the front wall.

In one embodiment, the at least one nasal prong has a rear wall extending between the inner wall and the outer wall, the inner wall having a thickness that is thinner than a thickness of the rear wall.

In one embodiment, the nasal prong defines a lumen that extends between the gas inlet and the gas) outlet, the shape of the lumen changing from generally oval at the gas inlet to generally elliptical at the gas outlet.

In one embodiment, the nasal prong defines a lumen that extends between the gas inlet and the gas) outlet, the shape of the lumen changing from generally kidney-bean shaped at the gas inlet to generally elliptical at the gas outlet.

In one embodiment, the at least one nasal prong further includes an exterior surface, at least a portion of the exterior surface is a sealing surface configured to seal the nare of the user's nose.

In one embodiment, the sealing surface is configured to seal with the nasal valve of the user's nose.

In one embodiment, the sealing surface is configured to seal between the user's nare entry and the nasal valve.

In one embodiment, the at least one nasal prong terminates at or proximate the nasal valve.

In one embodiment, the sealing surface comprises a tapered surface with a cross-section of the sealing surface near the gas inlet being larger than the cross-section of the sealing surface of the prong near the gas outlet.

In one embodiment, the exterior surface of the at least one nasal prong has an elbow portion.

In one embodiment, the at least one nasal prong has an external cross-section that varies along the length of the at least one nasal prong.

In one embodiment, the at least one nasal prong is tapered with the cross-section of the exterior surface of the prong near the gas inlet being larger than the cross-section of the exterior surface of the prong near the gas outlet.

In one embodiment, the lumen of the at least one nasal prong has an internal cross-section that varies along the length of the at least one nasal prong.

In one embodiment, the nasal prong is shaped to avoid contact with the septum of a user at the base of a user's nose.

In one embodiment, the nasal prong is shaped to substantially align the flow of breathing gas through the gas outlet with a user's upper airways.

In one embodiment, the nasal prong is shaped to extend generally upwardly and rearwardly into a user's nares, the nasal prong having a curvature that includes at least two inflection points.

In one embodiment, the nasal prong defines a lumen that extends between the gas inlet and the gas outlet, the shape of the lumen changing from generally oval at the gas inlet to generally elliptical at the gas outlet.

In one embodiment, the nasal prong defines a lumen that extends between the gas inlet and the gas outlet, the shape of the lumen changing from generally kidney-bean shaped at the gas inlet to generally elliptical at the gas outlet.

In one embodiment, the prong is shaped to maximize the cross-sectional area of the lumen.

In one embodiment, the patient interface comprises two nasal prongs spaced symmetrically about a user's sagittal plane, the prongs extending inwardly towards the user's sagittal plane below the user's nose from a base on a common support disposed along a user's upper lip.

In one embodiment, the prongs extend from the body toward the user's septum and curve around the corners of a user's nostrils upwardly and rearwardly into the user's nares, each prong extending along a generally inclined posterior trajectory and passing through two mediolateral points of inflection that orientate the gas outlet with respect to the user's upper airway passages.

In one embodiment, the at least one prong has a shaped trajectory fitting the anatomical shape of the user's nostril.

In one embodiment, wherein in a first portion (or phase) of the at least one prong, the trajectory moves horizontally towards the midline of the face, in a second portion (or phase) of the prong, the trajectory curves upwards directly into the nostril towards the crown of the head, in a third portion (or phase) of the prong, the trajectory rolls backwards into the head following the anatomical curvature of the nostril, and in a fourth portion (or phase), the trajectory tilts horizontally towards the centre of the patient interface to align the flow outlet with the user's upper airway.

In one embodiment, the at least one prong has a cross-section that varies along the central trajectory.

In one embodiment, the cross-sectional diameter generally decreases along the trajectory from the first portion (or phase) to the end of the fourth portion (or phase).

In one embodiment, the patient interface further comprises a contoured backing or facial pad configured to rest on a user's face.

In one embodiment, the backing or facial pad is preformed to be of a contour that is substantially curved to fit a user's face or upper lip region.

In one embodiment, the patient interface is a nasal cannula.

In another aspect, the disclosure broadly consists in a patient interface comprising: a body and at least one nasal prong extending from the body, the at least one nasal prong having a gas inlet for fluid communication with a supply of breathable gas, and a gas outlet configured to direct a flow of gas towards a nare of the user's nose, wherein the nasal prong is shaped to avoid contact with the septum of a user at the base of a user's nose.

In one embodiment, the patient interface has two nasal prongs, where the two prongs have a recess between the prongs to avoid contact with the septum.

In one embodiment, the recess is a scalloped recess.

In one embodiment, the at least one nasal prong further includes an exterior surface, at least a portion of the exterior surface is a sealing surface configured to seal the nare of the user's nose.

In one embodiment, the sealing surface is configured to seal with the nasal valve of the user's nose.

In one embodiment, the sealing surface is configured to seal between the user's nare entry and the nasal valve.

In one embodiment, the at least one nasal prong terminates at or proximate the nasal valve.

In one embodiment, the sealing surface comprises a tapered surface with a cross-section of the sealing surface near the gas inlet being larger than the cross-section of the sealing surface of the prong near the gas outlet.

In one embodiment, the exterior surface of the at least one nasal prong has an elbow portion.

In one embodiment, the at least one nasal prong has an external cross-section that varies along the length of the at least one nasal prong.

In one embodiment, the at least one nasal prong is tapered with the cross-section of the exterior surface of the prong near the gas inlet being larger than the cross-section of the exterior surface of the prong near the gas outlet.

In one embodiment, the lumen of the at least one nasal prong has an internal cross-section that varies along the length of the at least one nasal prong.

In one embodiment, the nasal prong is shaped to avoid contact with the septum of a user at the base of a user's nose.

In one embodiment, the nasal prong is shaped to substantially align the flow of breathing gas through the gas outlet with a user's upper airways.

In one embodiment, the nasal prong is shaped to extend generally upwardly and rearwardly into a user's nares, the nasal prong having a curvature that includes at least two inflection points.

In one embodiment, the nasal prong defines a lumen that extends between the gas inlet and the gas outlet, the shape of the lumen changing from generally oval at the gas inlet to generally elliptical at the gas outlet.

In one embodiment, the nasal prong defines a lumen that extends between the gas inlet and the gas outlet, the shape of the lumen changing from generally kidney-bean shaped at the gas inlet to generally elliptical at the gas outlet.

In one embodiment, the prong is shaped to maximize the cross-sectional area of the lumen.

In one embodiment, the patient interface comprises two nasal prongs spaced symmetrically about a user's sagittal plane, the prongs extending inwardly towards the user's sagittal plane below the user's nose from a base on a common support disposed along a user's upper lip.

In one embodiment, the prongs extend from the body toward the user's septum and curve around the corners of a user's nostrils upwardly and rearwardly into the user's nares, each prong extending along a generally inclined posterior trajectory and passing through two mediolateral points of inflection that orientate the gas outlet with respect to the user's upper airway passages.

In one embodiment, the at least one prong has a shaped trajectory fitting the anatomical shape of the user's nostril.

In one embodiment, wherein in a first portion (or phase) of the at least one prong, the trajectory moves horizontally towards the midline of the face, in a second portion (or phase) of the prong, the trajectory curves upwards directly into the nostril towards the crown of the head, in a third portion (or phase) of the prong, the trajectory rolls backwards into the head following the anatomical curvature of the nostril, and in a fourth portion (or phase), the trajectory tilts horizontally towards the centre of the patient interface to align the flow outlet with the user's upper airway.

In one embodiment, the at least one prong has a cross-section that varies along the central trajectory.

In one embodiment, the cross-sectional diameter generally decreases along the trajectory from the first portion (or phase) to the end of the fourth portion (or phase).

In one embodiment, the patient interface further comprises a contoured backing or facial pad configured to rest on a user's face.

In one embodiment, the backing or facial pad is preformed to be of a contour that is substantially curved to fit a user's face or upper lip region.

In one embodiment, the patient interface is a nasal cannula.

In another aspect, the disclosure broadly consists in a nasal prong for a patient interface comprising: a generally annular wall defining a lumen, the lumen having a gas inlet for fluid communication with a supply of breathable gas, and a gas outlet configured to direct a flow of gas towards a nare of the user's nose, the wall having an inlet end, an outlet end, and a substantially flexible portion, wherein the substantially flexible portion is configured to roll over itself when the outlet end is moved towards the inlet end.

In one embodiment, the outlet end of the wall has a larger diameter than a diameter of the inlet end of the wall.

In one embodiment, a portion of the wall at or near the inlet end of the wall is stiffer than the substantially flexible portion.

In one embodiment, the substantially flexible portion is configured to roll over the exterior surface of the wall.

In one embodiment, the wall includes a rounded ledge between the flexible portion and the inlet end.

In one embodiment, wherein a portion of the wall between the rounded ledge and the inlet end has a substantially constant diameter along its length.

In one embodiment, wherein a portion of the wall between the rounded ledge and the outlet end has a substantially constant diameter along its length.

In one embodiment, wherein, when the flexible portion is rolled over, the flexible portion provides a sealing surface configured to seal the nare of the user's nose.

In one embodiment, when unrolled, prong is wine-glass shaped.

In one embodiment, there is provided a securement system for a patient interface and/or patient interface tubing comprising: a first patch defining a securement footprint, the first patch having a user side and an interface side, the user side of the first patch being configured to attach or adhere to a user's skin, and a securing patch, at least a part of the securing patch being configured to extend over a patient interface and/or associated patient interface tubing and affixes to the patient interface side of the first patch to secure the patient interface to the user, the securing patch and the first patch being configured so that the securing patch can be contained within or bounded by the securement footprint of the first patch when the securement system is applied to a patient with a suitable or compatible patient interface.

In one embodiment, the first patch has the same or a greater surface area than the securing patch.

In one embodiment, the securement patch is shaped or otherwise configured to accommodate geometric or other features of the patient interface and/or associated patient interface tubing.

In one embodiment, the securement patch has at least one wing.

In one embodiment, the securement patch has a pair of wings arranged at one end of the patch, the wings are configured to secure to the first patch on either side of a patient interface and/or associated patient interface tubing.

In one embodiment, the securement patch has a tube end wing, the tube end wing being configured to extend, or for extending, under the patient interface tubing and affix to the first patch.

In one embodiment, the user side of the first patch has a dermatologically sensitive adhesive (such as a hydrocolloid for example) that attaches or adheres the first patch to a user's skin.

In one embodiment, the first patch has a surface of sufficient area such that, the surface distributes pressure the attachment or adhering forces across the user's skin.

In one embodiment, the first patch is a dermal patch configured to attach or adhere to a user's face.

In one embodiment, the dermal patch is configured to attach or adhere to a user's face adjacent the user's upper lip and/or cheek.

In one embodiment, the securement system is configured to receive and/or secure a nasal cannula and/or associated tubing, the tubing extending from one or both sides of a user's face.

In one embodiment, the securement system is configured for use with an infant or neonatal infant.

In one embodiment, the securement system is configured for use with a nasal cannula as described herein.

In one embodiment, the securement system is configured for use with a tube as described herein.

In one embodiment, there is provided a securement system for a patient interface and/or patient interface tubing comprising a two-part releasable attachment or connection arrangement, the arrangement comprising a first patch and a second patch: the first patch having a patient side and an interface side, the patient side of the first patch being attachable to the skin of a user, (such as for example by an adhesive, generally being of a dermatologically sensitive adhesive such as a hydrocolloid), the interface side of the first patch being provided with the first part of a two-part releasable attachment or connection system, and the second patch having an interface side and patient side, the patient side of the second patch being provided with the complimentary second part of the two-part releasable attachment or connection system, the interface side of the second patch being attachable or connected to the patient interface and/or associated patient interface tubing, for example by adhesive or may be formed as a part of the patient interface or may be provided as a back surface of the patient interface upon which is provided the second part of the two-part system.

In one embodiment, the interface side of the first patch has one of a hook or a loop, and the second part of the second patch has the other of the hook or loop, such that the first and second parts (and patches) are releasably attachable or connectable to each other.

In one embodiment, the first patch is locatable and/or attachable to the skin of a user's face.

In one embodiment, the second patch is locatable, or attached or attachable, or is connected to, or with, a patient interface.

In one embodiment, the second patch is formed integrally with, or forms a part of, a patient interface.

In one embodiment, the first part of the two-part releasable attachment or connection system on the first patch occupies less than about 90%, or about 85%, or about 75%, or about 60% or about 50% or about 40% or about 30% or about 20% or about 10% of the interface side of the first patch.

In one embodiment, the first part of the two-part releasable attachment or connection system is adhered or adherable to the patient interface side of the first patch with a suitable adhesive.

In one embodiment, the user side of the first patch has a dermatologically sensitive adhesive (such as a hydrocolloid for example) that attaches or adheres the first patch to a user's skin.

In one embodiment, the first patch has a surface of sufficient area such that, the surface distributes pressure the attachment or adhering forces across the user's skin.

In one embodiment, the first patch is configured to attach or adhere to a user's face.

In one embodiment, the first patch is configured to attach or adhere to a user's face adjacent the user's upper lip and/or cheek.

In one embodiment, the securement system is configured to receive and/or secure a nasal cannula and associated tubing, the tubing extending from one or both sides of a user's face.

In one embodiment, the securement system is configured for use with an infant or neonatal infant.

In one embodiment, the securement system is configured for use with a nasal cannula as described herein.

In one embodiment, the securement system is configured for use with a tube as described herein.

In one embodiment, a securement patch is applied or applicable over the patient interface and affixed or affixable to the first patch to provide additional securement.

In one embodiment, the first part of the two-part releasable attachment or connection system includes a substrate secured to, or for securing to, the first patch.

In one embodiment, the substrate portion includes at least one slit or at least one slot with areas of the substrate portion separated by the slit or slot.

In one embodiment, the substrate portion includes a plurality of slits or slots or both which together divide the substrate portion into a serpentine body.

In one embodiment, the slits and/or slots are arranged in the substrate such that a first set of at least one set of slits or slots extends into the substrate from one edge of the substrate and a second set of slits or slots extends into the substrate from the other edge of the substrate, the slits or slots of a set being interleaved with the slits or slots of the other set such that a path along the substrate portion from one end to another end without crossing the slits or slots must follow a zigzag or serpentine path much longer than a direct line between the ends.

In one embodiment, a slit or slot of the plurality of slits or slots is curved.

In one embodiment, a plurality of the slits or slots is curved and the curved slits or slots are arranged substantially parallel.

In one embodiment, the slits or slots are arranged in a herring bone pattern extending in from the edges of the substrate portion.

In one embodiment, the substrate is divided into separated portions by a serpentine slit or slot.

In one embodiment, the substrate portion is divided into portions by a spiral slit or slot.

In one embodiment, the substrate portion is divided into sub-portions by slits or slots arranged on substantially concentric circles.

In one embodiment, the concentric circles are centred at approximately the centre of the substrate portion.

In one embodiment, the slit or slots divide the substrate portion into a plurality of islands, each joined to an adjacent island or islands by a narrow bridge.

In one embodiment, the substrate portion is divided into portions by an S-shaped slit.

In one embodiment, the substrate portion is divided into portions by a T-shaped slit.

In one embodiment, the substrate portion covers at least 70% of the area of the first patch.

In one embodiment, for a boundary defining the shortest path around the perimeter of the substrate, the substrate portion covers at least 80% of the area within the boundary.

In one embodiment, there is provided a part of a releasable fastener that includes a substrate portion supporting a distributed mechanical fastener across its surface, the substrate portion being flexible but substantially non-stretchable, the substrate portion being divided into multiple areas by at least one slit or at least one slot, such that the substrate may substantially conform to an underlying compound curved surface by independent bending of different divided portions of the substrate.

In one embodiment, the substrate portion includes a plurality of slits or slots or both which together divide the substrate portion into a serpentine body.

In one embodiment, there is provided a patient interface assembly comprising:
 a securement system for the patient interface and/or a component associated with the patient interface (e.g. such as a tube or tubing), and
 a tube connected to the patient interface providing at least a part of a breathing circuit for a user of the interface,
 wherein the securement system comprises a two-part releasable attachment (or connection) arrangement, the arrangement comprising:
 a first patch and a second patch,
 the first patch having a patient side and an interface side,
 the patient side of the first patch being attachable to the skin of a user, (e.g. by an adhesive, generally being of a dermatologically sensitive adhesive such as a hydrocolloid),
 the interface side of the first patch being provided with the first part of a two-part releasable attachment or connection system, and
 the second patch having an interface side and patient side,
 the patient side of the second patch being provided with the complimentary second part of the two-part releasable attachment or connection system,
 the interface side of the second patch being attachable (or connectable) to the patient interface and/or the component associated with the patient interface (e.g. a tube or tubing).

In one embodiment, the interface is a nasal cannula.

In one embodiment, the interface includes one or a pair of nasal prongs.

In one embodiment, the interface comprises a securement system.

In one embodiment, the tube is a medical breathing tube.

In one embodiment, the tube has a patient interface end that may be soft, or less rigid, compared to an adjacent section of the tube.

In one embodiment, the interface is a nasal cannula arrangement comprising: at least one nasal prong, the prong having a gas outlet adapted to be inserted into a user's nare and a gas inlet fluidly connected to the gas outlet, the at least one nasal prong comprising a backing, the backing configured to rest on a user's face, wherein a lip extends about at least a part of the perimeter of a rear surface of the backing, the rear surface configured for receiving or retaining the second patch, such that in use, the second patch may be releasably attachable or connectable to, or with, the first patch affixed to a user's face.

In one embodiment, the lip is a barrier.

In one embodiment, the lip is deformable.

In one embodiment, the lip extends at least about the perimeter of a region substantially adjacent to a prong associated with the backing.

In one embodiment, the lip is an endless lip extending about the perimeter of the rear surface of the backing.

In one embodiment, the lip is a series of one or more separate lips.

In one embodiment, the one or more separate lips are adjacent or adjoining or overlapping lip portions.

Preferably, in use, the lip substantially forms a fluid (e.g. liquid) seal, or barrier to fluid, between the rear surface of the backing and a cannula facing surface of the second patch.

In one embodiment, the backing is substantially planar or flat or contoured (such as a pre-formed curve) backing configured to rest on a user's face.

In one embodiment, the backing assists as a stabilizer of the prong(s) in the nare(s) of a user.

In one embodiment, the at least one backing extends laterally outward from the at least one nasal prong, away from the septum of a user.

In one embodiment, the securement system may further comprise a chinstrap.

In one example embodiment, the chinstrap is a continuous loop that extends around the back and/or top of the patient's head.

In one embodiment, the chinstrap comprises a slit or bifurcation to allow it to conform to the patient's curved chin region.

In one embodiment, the securement system may further comprise a bonnet.

In one embodiment, the securement system may further comprise at least one headgear strap that extend down the side of the patient's cheek (like side burns).

In one embodiment, the chin strap attachable to the bonnet.

In one embodiment, the chin strap comprises hook and/or loop material. The hook and/or loop material may be in one or more regions. Alternatively, the hook and/or loop material may extend continuously on at least one side of the chin strap. The hook material may be in at least one region, and the loop material may be in at least another region.

In one embodiment, the at least one headgear strap that extends down the side of the patient's cheek is attachable to the bonnet.

In one embodiment, the at least one headgear strap that extends down the side of the patient's cheek comprises hook and/or loop material. The hook and/or loop material may be in one or more regions. Alternatively, the hook and/or loop material may extend continuously on at least one side of the at least one headgear strap. The hook material may be in at least one region, and the loop material may be in at least another region.

Reference to a 'substrate' refers to the medium which carries or supports one part of a two-part releasable attachment or connection system. For example, the 'substrate' may be a fastener substrate which carries a fastener, where the fastener forms one part of a two part releasable attachment or connection system.

The at least one slit or at least one slot is provided a slit or a slot or other cut or removal of material from the substrate (and to ensure the substrate and the at least one part of the two-part releasable attachment or connection system) is provided so as to be of separated or divided areas. Such separation or division or slits or slots allow for a conformability of a or the patch when applied to a patient's face.

In one embodiment, the securement system may further comprise at least one fastener. The at least one fastener may be tube clip. The at least one clip may have a pair of resilient arms that grasp the tube. The clip may be attachable to the bonnet, the chin strap, and/or the strap that extends down the side of the patient's cheek. The clip may attach to the bedsheets. The clip may have one or more portions of hook and/or loop material, or other attachments means, for attaching to the bonnet, the chin strap, the strap that extends down the side of the patient's cheek, and/or the bedsheets.

The at least one fastener may be a sleeve. The sleeve may be a short strip of material. The material may include a portion of hook material, or a portion of loop material or portions of both hook material and loop material. This may allow the sleeve to be fastened in position somewhere on the headgear. The sleeve may be formed by at least one slit, slot, or cut in the material that provide a central portion. When assembled with the tube, a central section of the fastener may be spaced away from the adjacent sections.

In one embodiment, the patient interface is configured to receive an inspiratory flow of gases via an inspiratory conduit.

In one embodiment, the patient interface is configured to direct a flow of the expiratory gases to an expiratory conduit.

In one embodiment, the inspiratory conduit and/or the expiratory conduit is a medical tube to transport gases.

In one embodiment, there is provided a patient interface assembly comprising: a tube management and retention system including a device configured to be removably attached to the tube and removably attached to any item in proximity to, or attached to, the patient.

In one embodiment, the item may be headgear, chin strap, bonnet, clothing, or bedsheets.

In one embodiment, the headgear comprises at least one headgear strap that extends down the side of the patient's face and cheek.

In one embodiment, the chin strap is attachable to a bonnet.

In one embodiment, the chin strap comprises hook and/or loop material. The hook and/or loop material may be in one or more regions. Alternatively, the hook and/or loop material may extend continuously on at least one side of the chin strap. The hook material may be in at least one region, and the loop material may be in at least another region.

In one embodiment, the at least one headgear strap that extends down the side of the patient's cheek is attachable to a bonnet.

In one embodiment, the at least one headgear strap that extends down the side of the patient's cheek comprises hook and/or loop material. The hook and/or loop material may be in one or more regions. Alternatively, the hook and/or loop material may extend continuously on at least one side of the at least one headgear strap. The hook material may be in at least one region, and the loop material may be in at least another region.

In one embodiment, the device comprises at least one fastener. The fastener may be a sleeve. The sleeve may be a short strip of material. The material may include a portion of hook material, or a portion of loop material or portions of both hook material and loop material. This may allow the sleeve to be fastened in position somewhere on the headgear. The sleeve may be formed by at least one slit, slot, or cut in the material that provide a central portion. When assembled with the tube, a central section of the fastener may be spaced away from the adjacent sections.

In one embodiment, there is provided a patient interface assembly comprising: a tube management and retention system including one or more pillows.

In one embodiment, there is provided a patient interface assembly comprising: a tube management system including a device configured to be removably attached to the tube and primarily and/or permanently attached to any item in proximity to, or attached to, the patient.

In one embodiment, the item may be headgear, chin strap, bonnet, clothing, or bedsheets.

In one embodiment, the headgear comprises at least one headgear strap that extend down the side of the patient's cheek (like side burns).

In one embodiment, the chin strap is attachable to a bonnet.

In one embodiment, the chin strap comprises hook and/or loop material. The hook and/or loop material may be in one or more regions. Alternatively, the hook and/or loop material may extend continuously on at least one side of the chin strap. The hook material may be in at least one region, and the loop material may be in at least another region.

In one embodiment, the at least one headgear strap that extends down the side of the patient's cheek is attachable to a bonnet.

In one embodiment, the at least one headgear strap that extends down the side of the patient's cheek comprises hook and/or loop material. The hook and/or loop material may be in one or more regions. Alternatively, the hook and/or loop material may extend continuously on at least one side of the at least one headgear strap. The hook material may be in at least one region, and the loop material may be in at least another region.

Although medical tubes exist in the prior art, it is recognised that there are problems with current medical tubes that extend between a respiratory component and a patient interface. Large diameter tubes are often used because decreasing the diameter of a medical tube can result in an increase in resistance to flow. However, some of these larger diameter tubes can also have high resistance to flow. Large medical tubes can also be heavy, bulky, and inflexible in use. They also may not be aesthetically pleasing to a patient, which can result in the treatment not being readily accepted by the patient. Because medical tubes stretch between a respiratory component and a patient interface, they can drag on the patient interface, causing discomfort to the patient and/or disrupting the treatment. Tubes can be noisy when moved or pushed against surfaces, causing the treatment to be obtrusive to the patient and/or a bed partner.

Some medical tubes may not provide good crush resistance. As a result, resistance to flow can be impaired following a crushing event in which the shape and/or lumen of the tube is disrupted. Similarly, the medical tube may not recover from the event but may continue to provide impaired treatment until intervention from the user or may be rendered useless.

A breathable tube can comprise a breathable film reinforced with a more rigid reinforcing member. Current breathable tubes may not be sufficiently robust and, as a result, can be easily damaged in use. When bent, the film may collapse and protrude into the lumen of the tube such that resistance to flow is increased. The breathable film may also be noisy such that it can be disruptive to the patient and/or bed partner.

A medical tube has been developed that at least partially ameliorates or overcomes at least one disadvantage of prior art tubes.

The medical tube can be a smaller diameter tube that provides better flexibility and crush resistance as well as a decreased resistance to flow when compared to existing tubes. The medical tube can extend between a respiratory component and a patient interface. The medical tube can comprise an extruded reinforcing member spirally wound with an extruded film.

A profile of the film can be controlled so that when the medical tube is bent, the film does not collapse into the lumen of the tube. The profile can comprise an inwardly biased profile between adjacent windings of the reinforcing member. The term "inwardly biased," as herein described, generally refers to a configuration in which the film extending between adjacent windings of the reinforcing member drapes toward the center of the lumen when the medical tube is not subject to deformational strain (that is, the medical tube is in a neutral position). The dimensions of the profile can allow the film to drape to a maximal level between adjacent windings of the reinforcing member without protruding into the lumen of the medical tube, thus minimising the effect bending the medical tube may have on resistance to flow.

Flexibility can be improved due to the extent that the film drapes between adjacent windings of the reinforcing member. This can improve the extensibility and bend radius of the medical tube. The pitch of the reinforcing member can also be controlled to improve flexibility. A relationship between the pitch, height, and width of the cross-section of the reinforcing member can provide improved tube characteristics.

The shape of the cross-section of the reinforcing member can be selected to reduce resistance to flow and to reduce the size of the cavities that exist between adjacent windings of the reinforcing member. The shape can also be important to provide a sufficient bonding surface between the film and the reinforcing member.

The reinforcing member can help to reduce vulnerability of the medical tube to crushing, and the medical tube can recover well following a crushing event or other application of force. In some embodiments the reinforcing member can roll or lean sideways and prevent the medical tube from being crushed, which can improve the recovery of the medical tube from the applied force.

The medical tube can be made to be much smaller in diameter than other medical tubes. In general, the diameter of the medical tube can be in the range of 1 and 20 mm (or thereabout), such as in the range of 7 and 16 mm (or thereabout). For example, small medical tubes, in the range of 14 and 16 mm (or thereabout) in diameter, can be provided to obstructive sleep apnea (OSA) patients, and even smaller medical tubes, in the range of 10 and 12 mm (or thereabout) or in the range of 7 and 9 mm (or thereabout) in diameter, can be provided to high flow therapy (HFT)

patients. Smaller medical tubes can improve patient perception of the treatment and can increase patient comfort by providing lighter weight tubes to connect between the respiratory component and the patient interface. Lighter weight and more flexible tubes can also reduce tube drag on the patient interface.

The materials used in the medical tube can also allow quieter and less obtrusive treatment to be provided to patients. As a result, patients may be more accepting of the treatment. Improving patient perception may also improve patient compliance.

In certain embodiments, some or all of the walls surrounding the lumen of the medical tube can comprise a breathable film made of a breathable material. A "breathable film" as herein described refers to a film that is highly permeable to water vapor and substantially impermeable to bulk flow of any liquid water and the bulk flow of gases from inside of the medical tube through to ambient air (i.e. the film lacks physical through-holes to allow bulk liquid water or bulk gases to be transmitted from inside of the medical tube to ambient air). Similarly, a "breathable material" generally refers to a material that is highly permeable to moisture vapor and substantially impermeable to bulk flow of any liquid moisture and the bulk flow of gases from inside of the medical tube through to ambient air. In certain embodiments, a breathable material has a moisture (water) vapor transmission rate greater than or equal to 650 g/m2/day (or thereabout) when measured according to Procedure B of ASTM E96 (using the upright cup method at a temperature of 23° C. and a relative humidity of 50%). The thickness of the breathable film can provide sufficient breathability and flexibility as well as strength and robustness to the medical tube.

In some embodiments, the film can be made from a breathable thermoplastic material, such as a thermoplastic elastomer (or TPE as defined by ISO 18064:2003 (E)), a thermoplastic polyurethane (or TPU as defined by ISO 18064:2003 (E)), a thermoplastic polyester, or other material with elastomeric properties. The elongate reinforcing member can be made from, for example, a TPU. The materials disclosed are not meant to be limiting but rather are examples of possible materials that can be used. The materials can be chosen such that a bond is formed between the elongate film and the elongate reinforcing member. The materials can be chosen such that when the medical tube moves and/or contacts other surfaces, it remains quiet and unobtrusive. Different materials and/or material combinations can fall within the scope of this disclosure.

A breathable film can advantageously help to expel condensate formed within the medical tube. At least one additional characteristic(s) of a medical tube disclosed herein is or are applicable to a medical tube comprising a film made of a breathable material. It should be understood, however, that at least one characteristic of a medical tube disclosed herein is applicable to a medical tube comprising a film made of a material that is not breathable.

In one aspect, the disclosure broadly consists in a first medical tube to transport gases comprises an elongate film spirally wrapped with an elongate reinforcing member to form a lumen. The elongate film bonds with the elongate reinforcing member. The elongate film comprises a profile that keeps the elongate film from protruding into the lumen of the first medical tube when the first medical tube is bent.

The elongate film can be made of a breathable material. The elongate film can be wrapped around a radially-outward surface of the elongate reinforcing member, facing away from the lumen, such that the elongate reinforcing member interacts with the lumen of the first medical tube and the elongate film forms the outer surface of the first medical tube. The longitudinal distance between corresponding points on adjacent windings of the elongate reinforcing member, measured when the first medical tube is not subject to deformational strain, can be selected such that the elongate film drapes a maximal amount between successive windings of the elongate reinforcing member while not extending inwardly beyond the elongate reinforcing member base into the lumen when the first medical tube is bent. The average radial distance from the lowest point of the elongate film in the lumen to the bottom of the elongate reinforcing member, measured when the first medical tube is not subject to deformational strain, can be less than 0.2 mm.

The profile of the first medical tube can be an inwardly biased profile. The elongate reinforcing member can comprise a D-shaped cross-section. The flat part of the D-shaped cross-section can be longitudinally aligned with the lumen. The semi-circular part of the D-shaped cross-section can be facing away from the lumen. The elongate film can bond to the semi-circular part of the D-shaped cross-section. Alternatively, the elongate reinforcing member can comprise a circular cross-section. Windings of the elongate reinforcing member can roll or lean sideways and prevent the first medical tube from being crushed in response to an applied force. The first medical tube can maintain a gases flow while such a force is applied. A maximal amount of the elongate film can extend between adjacent windings of the elongate reinforcing member without protruding into the lumen. The elongate reinforcing member can be hollow. The elongate reinforcing member can comprise a cavity configured to hold or transport a fluid.

In one aspect, the disclosure broadly consists in a second medical tube to transport gases comprises an elongate film spirally wrapped with an elongate reinforcing member to form a lumen. The elongate reinforcing member comprises a D-shaped cross-section. The elongate film bonds to a semi-circular part of the D-shaped cross-section of the elongate reinforcing member. A maximal amount of the elongate film extends between adjacent windings of the elongate reinforcing member without protruding into the lumen.

The elongate film can be made of a breathable material. The elongate film can be wrapped around a radially-outward surface of the elongate reinforcing member, facing away from the lumen, such that the elongate reinforcing member interacts with the lumen of the second medical tube and the elongate film forms the outer surface of the second medical tube. The average radial distance from the lowest point of the elongate film in the lumen to the bottom of the elongate reinforcing member, measured when the second medical tube is not subject to deformational strain, can be less than 0.2 mm. The profile can be an inwardly biased profile. The flat part of the D-shaped cross-section can be longitudinally aligned with the lumen. The semi-circular part of the D-shaped cross-section can be facing away from the lumen. Windings of the elongate reinforcing member can roll or lean sideways in response to an applied force. The medical second tube can maintain a gases flow while the force is applied. The elongate reinforcing member can be hollow. The elongate reinforcing member can comprise a cavity configured to hold or transport a fluid.

The term 'comprising' as used in this specification and claims means 'consisting at least in part of'. When interpreting statements in this specification and claims which include the term 'comprising', other features besides the features prefaced by this term in each statement can also be present. Related terms such as 'comprise' and 'comprised' are to be interpreted in a similar manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

As used herein the term '(s)' following a noun means the plural and/or singular form of that noun.

As used herein the term 'and/or' means 'and' or 'or', or where the context allows both.

The invention consists in the foregoing and also envisages constructions of which the following gives examples only.

BRIEF DESCRIPTION OF THE DRAWINGS

These and other features, aspects and advantages of the present disclosure will now be described with reference to the drawings of preferred embodiments, which embodiments are intended to illustrate and not to limit the disclosure, and in which figures:

FIG. 13A is a schematic oval shape, which one embodiment of the cross-section of the nasal prong is based on.

FIG. 13B is a schematic kidney-bean/lung shape, which one embodiment of the cross-section of the nasal prong is based on.

FIG. 14 is a schematic elliptical shape.

FIG. 15 is a cross-section of the patient interface of FIG. 3, showing details of the nasal prong, 'i' is the cross-section near the prong gases inlet and 'ii' is the cross-section near the gases outlet.

FIGS. 18A and 18B are schematic cross-sections of example nasal prongs generally showing the thick and thin wall regions. 'A' shows a flow passage that is similar to the cross-section of the prong whereas 'B' shows a flow passage that is elliptical.

FIGS. 50A to 50C are a schematic of an alternative embodiment fastener.

FIGS. 53A to 53D are a schematic of an alternative embodiment fastener.

FIGS. 55A to 55C are a schematic of an alternative embodiment fastener.

FIG. 59 is a schematic of an alternative embodiment tube management arrangement.

FIGS. 60A and 60B are schematics of an alternative embodiment tube management arrangement.

FIGS. 72A and 72B illustrate example embodiments of a fixation structure.

DETAILED DESCRIPTION

Figure 1A:
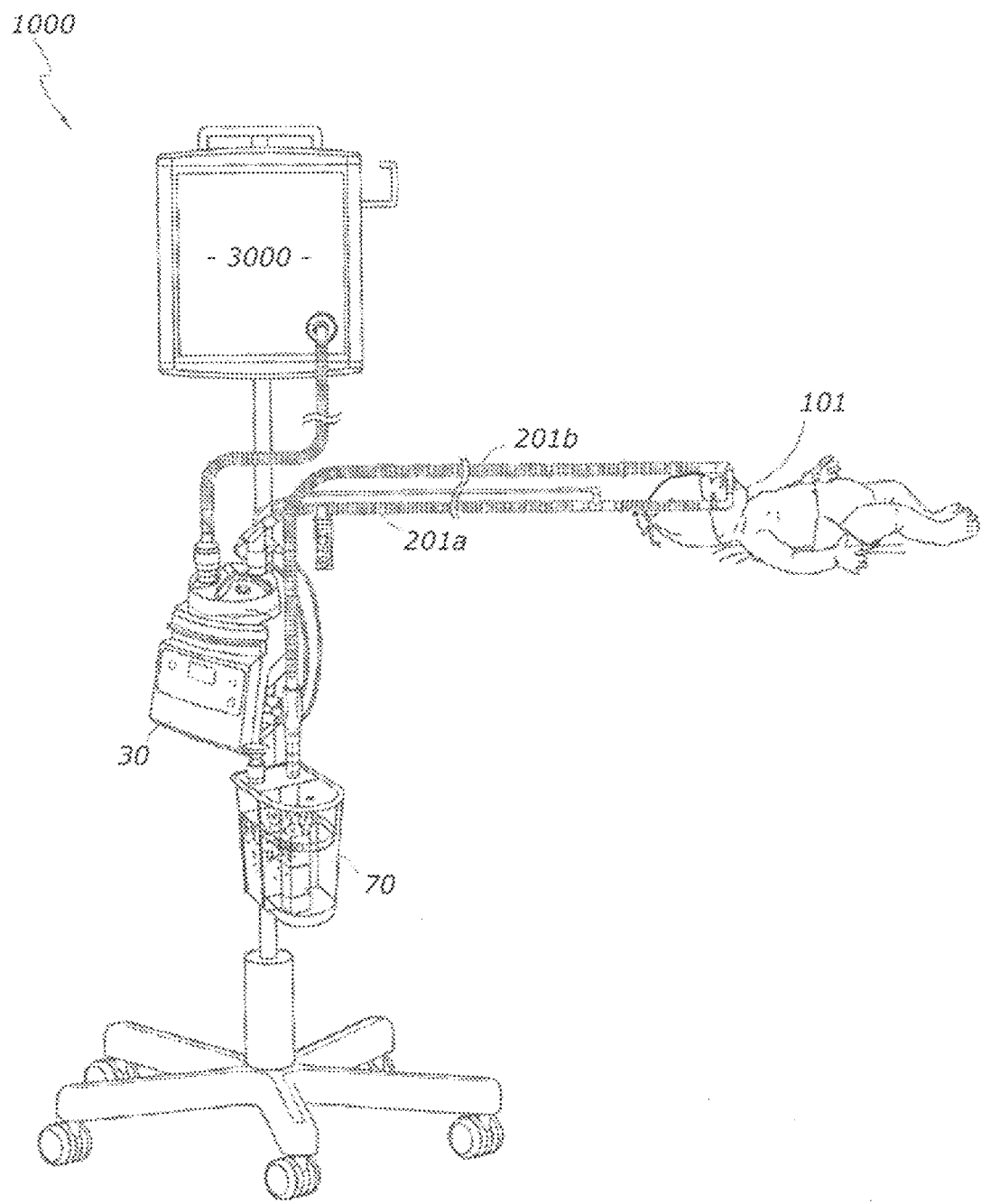
FIG. 1A shows a system in which embodiments of the patient interface are used.

FIG. 1A shows a system 1000 in which embodiments of the patient interface 101 are used. The patient interface 101 receives an inspiratory flow of gases via an inspiratory tube 201a, and a flow of the expiratory gases is directed from the interface via an expiratory tube 201b to a bubbler device 70. A humidifier system 30 is provided, which provides for a chamber sitting atop a heater base, the chamber of which is fed with a source of gases flow from, for example, a hospital or other supply source 3000. One of skill in the art would understand that such a system may include additional and/or replacement components as are known in the art.

Figure 1B:
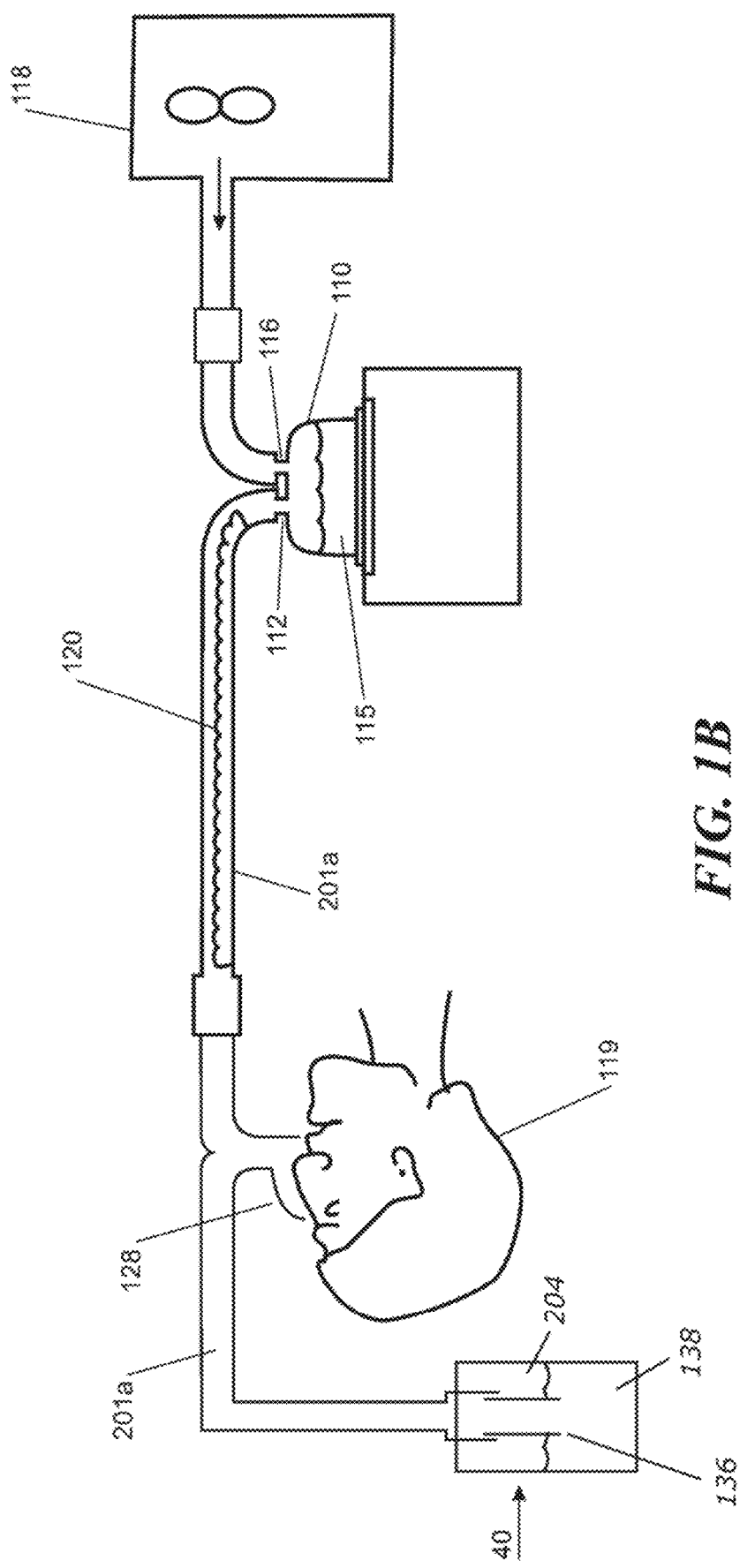
FIG. 1B is a block diagram showing a typical configuration for supplying breathing assistance to a patient.

Referring now to FIG. 1B another example of a system including a bubbler device and humidifier is depicted. A humidified Positive End Expiratory Pressure (PEEP) system is shown in which a patient 119 is receiving humidified and pressurised gases through a patient interface in the form of a nasal mask 128 connected to an inspiratory or inhalatory conduit 201a. It should be understood that the present invention, however, is not limited to the delivery of PEEP gases but is also applicable to other types of gases delivery systems and may not necessarily involve humidification. Inspiratory conduit 201a is connected to the outlet 112 of a humidification chamber 110, which contains a volume of water 115. Inspiratory conduit 201a may contain heating means or heater wires 120 that heat the walls of the conduit to ensure a constant humidity profile along the conduit and therefore reduce condensation of humidified gases within the conduit. As the volume of water 115 within humidification chamber 110 is heated, water vapour begins to fill the volume of the chamber above the water's surface and is passed out of the humidification chamber 110 outlet 112 with the flow of gases (for example air) provided from a gases supply means or blower 118 which enters the chamber 110 through inlet 116.

The humidified gases pass through the inspiratory conduit 201a to the nasal mask 128 being worn by the patient 119. The excess gases then flow through an expiratory or exhalatory conduit 201b to a pressure regulator 40.

In the preferred embodiment of the present invention the pressure regulator 40, takes the form of discharging the flow of exhalatory gases into a chamber 204 containing a column of water 138. The gases flowing through the expiratory conduit 201b are discharged into the body of water 138 from a short conduit 136 which extends from the expiratory conduit 201b into the chamber 204. This results in a bubbling effect, whereby the gases eventually exit the chamber 204 via the outlet port, which can also be used to initially fill the chamber 204 with water. The outlet port includes shielding to prevents liquid aerosols created by the vigorous bubbling on the surface of the water from being expelled. It will be appreciated that the short conduit 136, could equally be integrated into the end of the expiratory conduit 201b.

Figure 2:
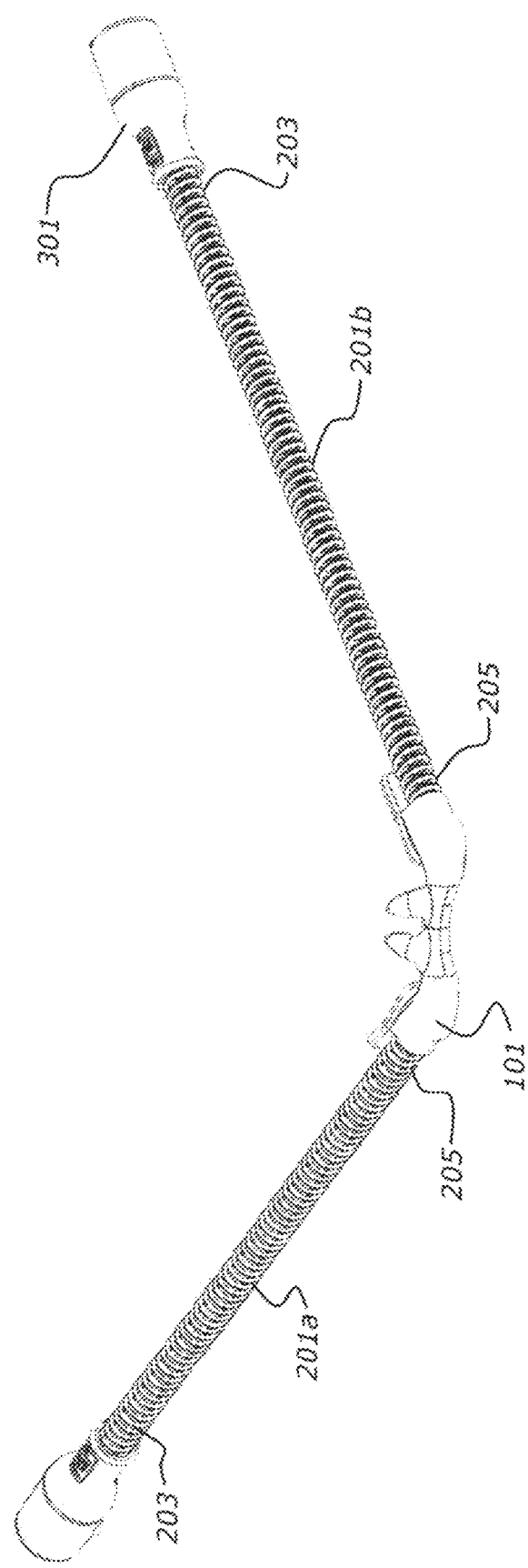
FIG. 2 is a perspective view of a patient interface with associated inspiratory and expiratory conduits.
Figure 3:
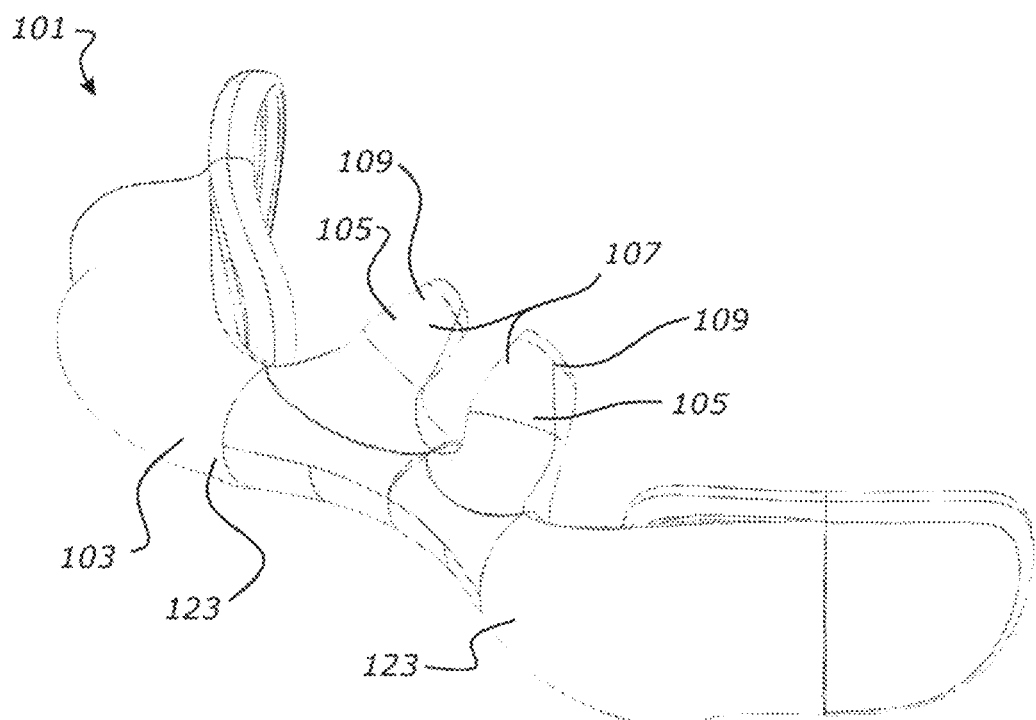
FIG. 3 is a perspective view from the front of one embodiment of a patient interface.
Figure 4:
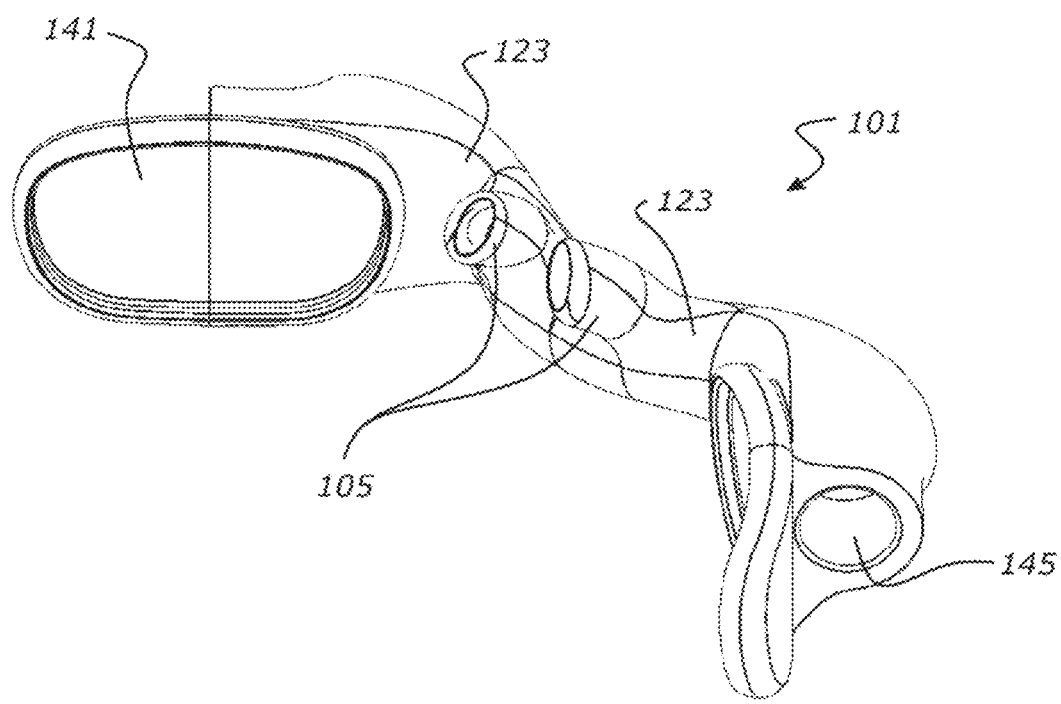
FIG. 4 is a perspective view from the rear of the patient interface of FIG. 3.

With reference to FIG. 2, in one embodiment, the patient interface 101 is a nasal cannula. The patient interface has a body 103 and at least one nasal prong 105 extending from the body 103. In some embodiments the patient interface 101 has a single nasal prong 105. In the embodiment shown in FIGS. 1 to 31, the patient interface 101 has two nasal prongs 105. While the following description refers to two nasal prongs 105, it will be appreciated that the description may also relate to a patient interface 101 having a single nasal prong 105.

The nasal prongs 105 of the patient interface shown and described herein are shaped for sealing in a patient's nares. In particular, the nasal prongs are shaped for sealing in an infant's nares. However, it should be appreciated that the prongs may be suitable for any patient population with similar nare geometry, and that the prongs may be provided in different absolute sizes for various patient populations. The prongs 105 are shaped and formed to minimise tissue compression and kinking during insertion into a patient's nares.

The nasal prong 105 has a gas inlet 106 for fluid communication with a supply of breathable gas. The nasal prong 105 has a gas outlet 108 configured to direct a flow of gas towards a nare of the user's nose. The nasal prong 105 further includes an exterior surface 107. At least a portion of the exterior surface is a sealing surface 109. The sealing surface 109 is configured to seal the nare of the user's nose.

In one embodiment, the sealing surface 109 is configured to seal with the nasal valve of the user's nose. In another embodiment, the sealing surface is configured to seal between the nare entry and the nasal valve.

In one embodiment, the nasal prong 105 terminates at or proximate the nasal valve.

The nasal prong 105 has an external cross-section that varies along the length of the nasal prong 105. The nasal prong 105 is tapered with the cross-section of the exterior surface of the prong near the gas inlet 106 being larger than the cross-section of the exterior surface of the prong near the gas outlet 108. The cross-section of the exterior surface of the prong near the gas inlet 106 is indicated by 'i' in FIG. 15. The cross-section of the exterior surface of the prong near the gas outlet 108 is indicated by 'ii' in FIG. 15. In one embodiment, the exterior shape of the nasal prong changes from a generally kidney-bean shape at the gas inlet to generally oval (having one axis of symmetry) or elliptical (having two axes of symmetry) at the gas outlet. In another embodiment, the exterior shape of the nasal prong changes from a generally oval shape at the gas inlet to generally elliptical at the gas outlet. In addition to changing cross-section, the exterior surface of the nasal prong has a sweep-type shape and 105 may have an elbow portion 111, which is described in more detail below.

The nasal prong 105 defines a lumen that extends between the gas inlet 106 and the gas outlet 108. In one embodiment, the shape of the lumen changes from generally oval at the gas inlet to generally elliptical at the gas outlet. In another embodiment, the shape of the lumen changes from generally kidney-bean shaped at the gas inlet to generally oval or elliptical at the gas outlet. The lumen shape may correspond to the exterior shape of the nasal prong 105. For example, both the exterior shape and the lumen may be kidney-bean shaped. Alternatively, the lumen shape may differ to the exterior shape of the nasal prong. For example, the exterior shape may be kidney-bean shaped and the lumen may be oval or elliptical.

FIG. 15 shows a side view section of the proposed nasal cannula and shows where the described cross-sections of the prong are taken. The gases inlet, shown by plane 'i', is taken at a place slightly away from the body 103 to show approximately where the desired oval and/or lung-shaped cross-section begins. It is taken here, slightly above the prong body, as the cross-section distorts where the prong 105 connects to the body 103, and because the region at and/or adjacent or nearby to plane "i" is expected to mate with the opening of the patient's nare.

The gases flow passage in the prong relates to the wall thickness. Different ways of forming this flow passage are shown in FIGS. 18A and 18B in relation to a cross-section of the prong near the gases inlet. The kidney bean shaped prong perimeter cross-section is used to highlight what may occur in uncommon shaped prong regions. FIG. 18A shows a flow passage perimeter being shaped similarly to the perimeter of the outside shape of the prong. FIG. 18B shows the flow passage as elliptical, which is different to the shape of the outer surface of the prong. It should be noted that any suitable flow path cross-sectional shape may be employed, so long as the preferred wall thicknesses described herein are maintained in desired regions. For example, the flow passage may not change shape. The flow passage may be circular along its entire length, oval along its entire length, or may be elliptical along its entire length.

Figure 19:
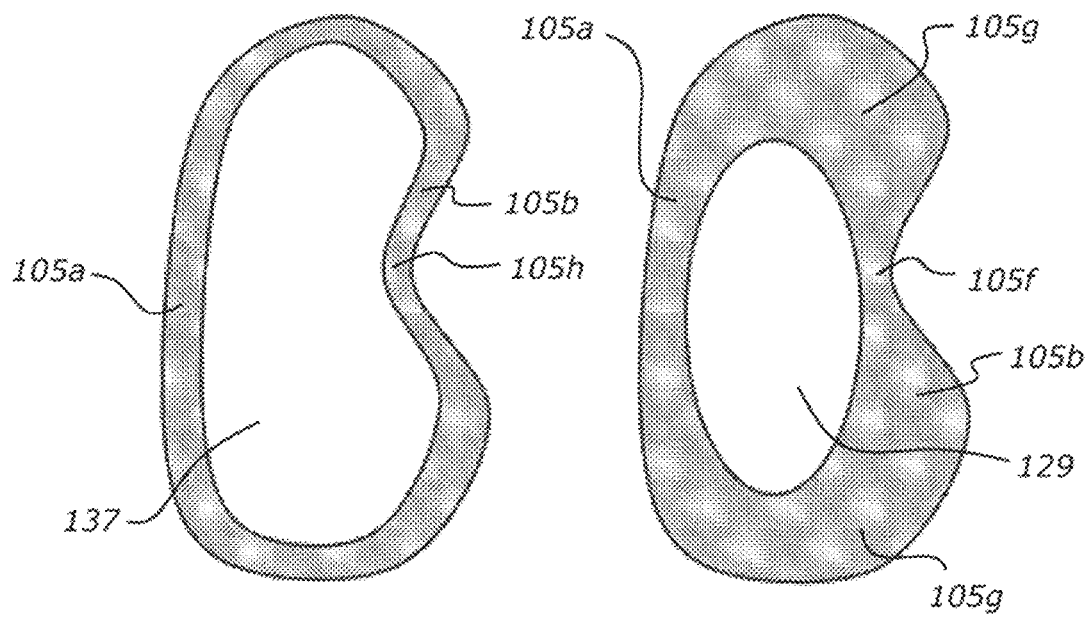
FIG. 19 is schematic cross-sections of an example nasal prong generally showing the thick and thin wall regions. This embodiment has an elliptical exterior and an elliptical lumen.

For instance, FIG. 19 shows an example schematic embodiment of a cross-section of the flow passage near the outlet of a preferred embodiment with thin and thick regions of the nasal prong wall. It should be appreciated by one of skill in the art that the thin wall may or may not be a constant thickness, such that different sections of the thinner wall 105a may be thicker or thinner than other sections of that wall. However, generally, the thinner wall 105a is relatively thinner than the thicker wall(s) 105b. Similarly, thicker wall(s) 105b may be of varying thickness at various sections of the wall.

The prongs 105 may also be tapered from the gases inlet 106 to the gases outlet 108. The cross-sectional area of the gases inlet 106 may be larger than the cross-sectional area of the gases outlet 108. The prong cross-sectional area gradually diminishes from the inlet to the outlet. This prong tapering aids in the sealing function of the prongs 105. When the prongs 105 are pushed up the patient's nares, they will seal somewhere along the length of the prong due to tapering in which the prongs 105 widen during insertion, towards the inlet. The tapering will aid in insertion of the prongs 105, as opposed to prongs which are of a constant cross-sectional area, or prongs which widen towards their distal ends.

In one embodiment the lumen of the nasal prong 105 has an internal cross-section that varies along the length of the nasal prong 105.

In one embodiment the nasal prong 105 is shaped to substantially align the flow of breathing gas through the gas outlet with a user's upper airways.

In one embodiment the nasal prong 105 is shaped to extend generally upwardly and rearwardly into a user's nares, the nasal prong 105 having a curvature that includes at least two inflection points.

In one embodiment, the nasal prong 105 defines a lumen 129 that extends between the gas inlet 106 and the gas outlet 108, the shape of the lumen changing from generally oval at the gas inlet to generally elliptical at the gas outlet.

In another embodiment, the nasal prong 105 defines a lumen 137 that extends between the gas inlet 106 and the gas outlet 109, the shape of the lumen changing from generally kidney-bean shaped at the gas inlet 106 to generally oval or elliptical at the gas outlet 108.

The nasal prong 105 is shaped to maximize the cross-sectional area of the lumen 129/137 while maintaining necessary wall thickness/thinness (as described elsewhere herein), sufficient structural integrity for insertion into a patient's nares without kinking, and being relatively simple to manufacture. FIG. 18A shows cross-section of the nasal prong and the cross-section of the lumen both being kidney bean shaped. That is, each is shaped generally as an oval, with a curved recess 105*h* on one side only. FIG. 18B shows the cross-section of the nasal prong being kidney bean shaped and the cross-section of the lumen 129 being elliptical. This forms a nasal prong with thicker sections 105*g*, and a thinner section 105*f*. The cross-sections of FIG. 18A also has thicker and thinner sections.

As discussed previously, the patient interface 101 may comprise two nasal prongs 105 spaced symmetrically about a user's sagittal plane, the prongs extending inwardly below the user's nose from a base 103 on a common support disposed along a user's upper lip.

The prongs 105 extend from the body toward the user's septum and curve around the corners of a user's nostrils upwardly and rearwardly into the user's nares, each prong extending along a generally inclined posterior trajectory and passing through two mediolateral points of inflection that orientate the gas outlet with respect to the user's upper airway passages.

The at least one prong has a shaped trajectory fitting the anatomical shape of the user's nostril.

In a first portion (or phase) of the prong 105, the trajectory moves horizontally towards the midline of the face, in a second portion (or phase) of the prong, the trajectory curves upwards directly into the nostril towards the crown of the head, in a third portion (or phase) of the prong, the trajectory rolls backwards into the head following the anatomical curvature of the nostril, and in a fourth portion (or phase), the trajectory tilts horizontally towards the centre of the patient interface 101 to align the flow outlet with the user's upper airway.

The prong 105 has a cross-section that varies along the central trajectory, as described above. For example, the cross-sections may be generally circular at the base of the trajectory and become generally oval or elliptical towards the end of the trajectory or prong.

The cross-sectional diameter generally decreases along the trajectory from the first portion (or phase) to the end of the fourth portion (or phase).

Figure 11A:
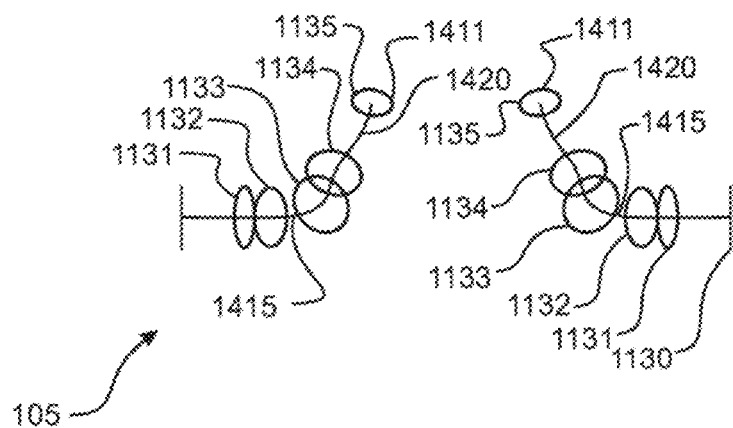
FIGS. 11A and 11B show the geometry of the prongs of the interface of FIG. 3 illustrated with swept lines that represent the prong trajectory.
Figure 11B:
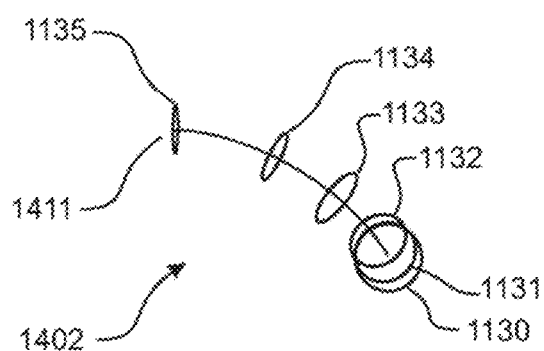

The geometry of the prongs in FIGS. 2-19 may be formed as illustrated in FIGS. 11A and 11B, with swept lines that represent the prong trajectory, and ellipses to 1135, that primarily represent the orientation of the lumen within each prong at a particular trajectory (but also show one potential cross-sectional lumen shape). Each prong may follow a swept path that is shaped to follow the anatomical geometry/curvature/contours of a user's nare. The prongs 105 are moulded or formed to follow the anatomical shape and curvature of a user's nare.

In one preferred form the prongs 105 are premoulded or preformed according to the anatomical shape of a nare, in contrast to prongs which are of a material that is conformable to the anatomical shape of a nare. In another preferred form, the prongs 105 are premoulded or preformed according to the anatomical shape of a nare, and further include at least one thinned wall section which is conformable so as to limit pressure on the patient's septum.

From the base 1415 each prong 105 sweeps upwardly or superiorly toward the crown of the user's head (away from the transverse plane) and rearwardly or posteriorly (toward the user's coronal plane) with respect to the user's upper lip. Between the ellipses 1131 and 1133 (the second phase) the lumen of the prongs 105 smoothly transitions from a generally mediolateral orientation along the user's upper lip to a predominantly inclined posterior orientation directing gas flow toward an upper portion of the back of a user's head. The lumen of the prong reduces slightly during this phase, becoming more elliptical to take advantage of the space available within the nostril.

In the third phase (between the ellipses 1133 and 1134) the prongs 105 continue along an inclined posterior trajectory toward the upper back of a user's head (away from the transverse plane and toward the coronal plane), with a smooth reduction in the rate of incline (the superior component of the prongs trajectory 1420 causing the lumen to move away from the transverse plane). During this phase the prongs have negligible convergence (or mediolateral component) toward the sagittal plane. The prong lumen reduces further during this phase, becoming increasingly elliptical.

In the final phase (between the ellipses 1134 and 1135) the prongs 105 continue along an inclined posterior trajectory with some mediolateral convergence toward the sagittal plane. The mediolateral convergence of the prongs 105 begins at the illustrated trajectory inflection point at the start of the fourth phase (or slightly prior) adjacent the ellipse 1134. There is a second inflection point adjacent the final ellipse 1135 that reduces convergence of the prongs 105 and orientates the prong outlet 1411 posteriorly (toward the coronal plane) with a slight mediolateral component toward the sagittal plane (represented by the orientation of the final ellipse 1135 in FIG. 11A).

The incline rate of the prong trajectories 1420 continues to decrease during the fourth phase, until the respective trajectories 1420 are substantially parallel with the transverse plane at the prong outlet 1411 (represented by ellipse 1135). The mediolateral and superior-inferior adjustments of the prong trajectories 1420 adjacent the final ellipse 1135 position the prong outlet 1411 generally in alignment with the passage of the upper airway to reduce soft tissue irritation caused by the exiting breathing gases. The prong lumen is elliptical at the outlet 1411, with the major elliptical axis arranged in a generally transverse plan. The outlet 1411 directs breathing gases upwardly or superiorly toward the crown of the user's head (away from the transverse plane) and rearwardly or posteriorly (toward the user's coronal plane).

In alternative embodiments the cross-section of the lumens may be triangular or quadrilateral.

Figure 11C:
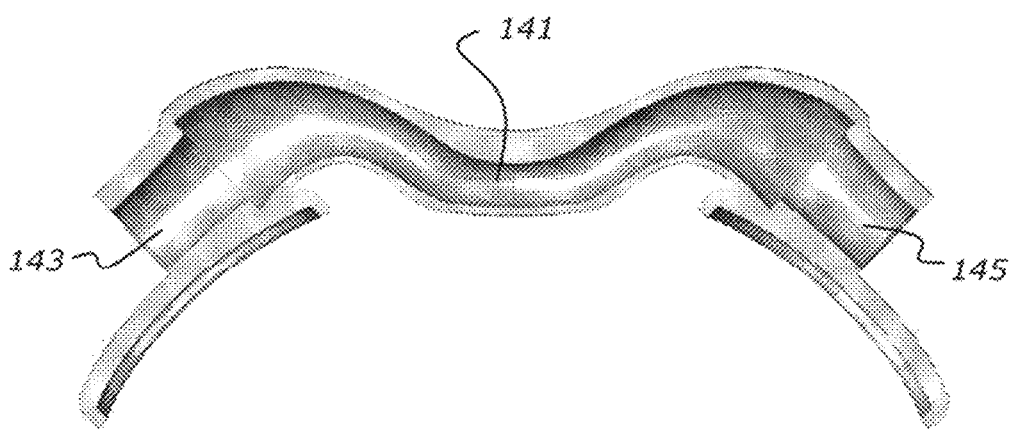
FIG. 11C is a cross-section of the patient interface of FIG. 3.
Figure 12A:
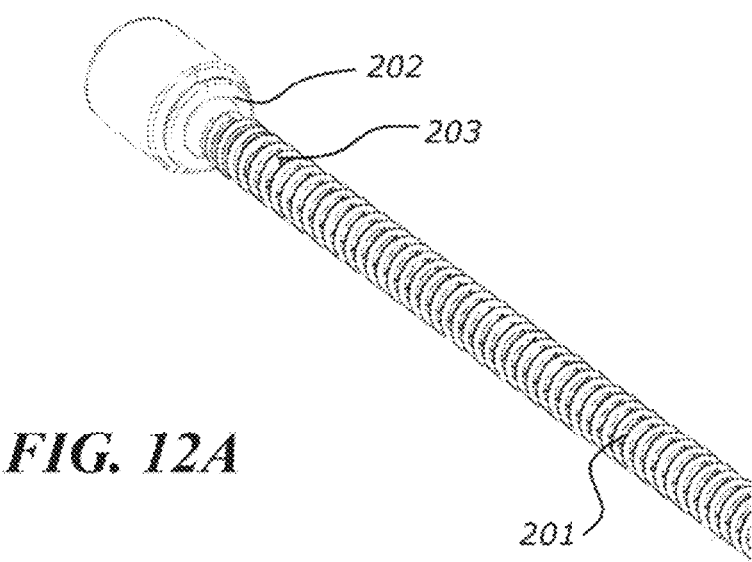
FIG. 12A is a detail view of the connector end of a conduit.
Figure 12B:
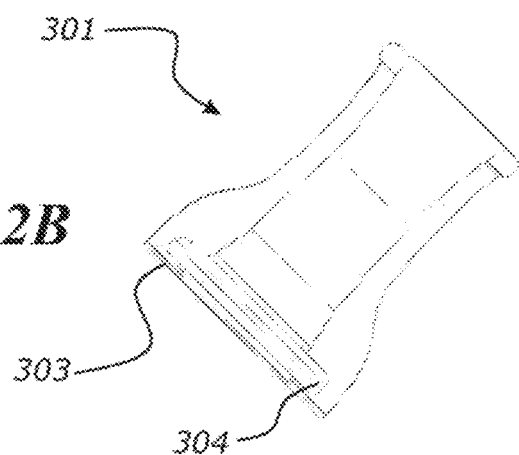
FIG. 12B is a cross-section of the conduit of FIG. 12A together with a sleeve.
Figure 12C:
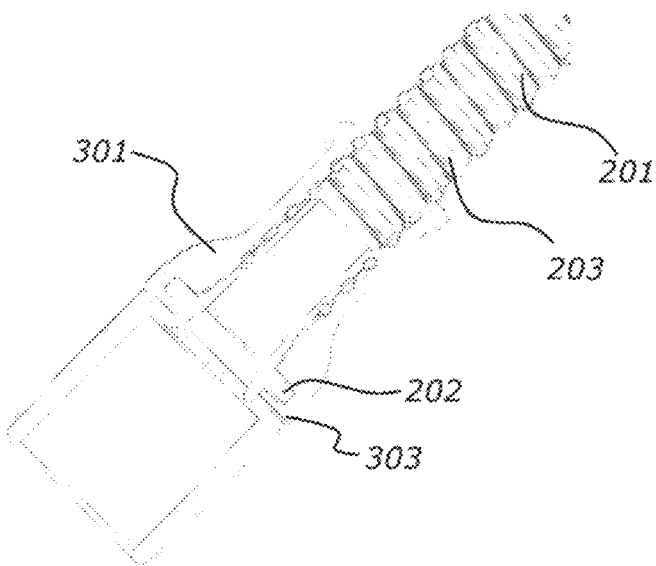
FIG. 12C is a cross-section of the conduit and sleeve of FIG. 12A.

In one embodiment, the patient interface 101 has a body 103 defining a manifold 141, shown in FIG. 11C. The manifold 141 includes a gas inlet for fluid communication with a supply of breathable gas. The manifold includes a gas outlet for fluid communication with expired gas. The patient interface 101 has two nasal prongs 105 extending from the body. Each nasal prong 105 has a gas inlet for fluid communication with the manifold to receive the supply of breathable gas. Each nasal prong 105 also has a gas outlet configured to direct a flow of gas towards a nare of the user's nose. The nasal prongs 105 are in fluid communication with each other via the manifold 141. Each nasal prong 105 further includes an exterior surface. At least a portion of the exterior surface is a sealing surface. The sealing surface is configured to seal the nare of the user's nose.

The patient interface 101 has a first opening 143 and a second opening 145. In a first configuration, the first opening 143 is the gas inlet of the manifold and the second opening 145 is the gas outlet of the manifold.

In a second configuration, the second opening 145 is the gas inlet of the manifold and the first opening 143 is the gas outlet of the manifold 141.

The first opening and the second opening are in fluid communication with each other via the manifold 141.

Except for the first and second openings, and the lumens of the nasal prongs, the manifold is sealed. The manifold 141 does not include a plurality of vent holes for patient exhalation or bias flow exhaust.

Providing fluid communication between an inspiratory side and an expiratory side of the patient interface is useful for effective CPAP delivery, as it allows a bias flow in excess of the patient's inspiratory demand to pass from the supply tube to the expiratory tube, and allows a single supply tube and single expiratory tube to service both prongs. In a further example embodiment, the expiratory tube is connected to an expiratory limb, which is connected to an expiratory pressure device, such as a bubbler (described with reference to FIG. 1). In such an example embodiment, none of the components along the expiratory side of the circuit (prongs, manifold, expiratory tube, (wye piece, if present), expiratory limb, expiratory pressure device) include a plurality of vent holes for patient exhalation or bias flow exhaust.

The middle region of the patient interface 101 may be relatively more rigid compared to the rest of the interface. This region may include the portion of the manifold between and/or proximate the prongs. Greater rigidity may be accomplished by varying at least one of geometry, material selection, and/or wall thicknesses. This provides structural integrity to avoid kinking (occluding or reducing flow) or tearing (leaking of flow) at that location, either of which would detrimentally impact delivery of the desired therapy, and may cause more serious effects such as suffocation or alveoli collapse.

The patient interface 101 further comprises a contoured backing or facial pad 141 configured to rest on a user's face.

The backing or facial pad is pre-formed to be of a contour that is substantially curved to fit a user's face, cheek or upper lip region.

With reference to FIGS. 34 to 43, an alternative embodiment of a patient interface 1101 will now be described. The patient interface 1101 has the same features and functions of the patient interface 101 described above, unless described below. Like numbers are used to indicate like parts, with the addition of 1000.

In this embodiment, the nasal prongs have a sealing region 1109 that is longer compared to the sealing region 109 of the earlier described embodiment. The longer sealing region 1109 causes the overall length of the nasal prong of this embodiment to be longer than the overall prong length of previously described embodiments. This has the additional benefit of the prong being less likely to flick out or otherwise disengage from the patient's nare. With reference to the swept lines that represent the prong trajectory, and the ellipses of FIGS. 45B and 45C, a prong sealing region 1109 is between ellipses 1134a and 1135. The prong sealing region 1109 is, or comprises, a tapered region with the cross-section of the exterior surface of the prong near the gas inlet being larger than the cross-section of the exterior surface of the prong near the gas outlet.

In the embodiment shown, the prong sealing region 1109 tapers from about 5 mm to about 4 mm, for example. The measurements of the prong (5 mm and 4 mm) refer to an equivalent diameter of an oval. The equivalent diameter may be a diameter calculated from the perimeter of the prong (circular and ovular prongs may have the same equivalent diameter) or it may be the largest width dimension of the prong (circular and ovular prongs may have a different equivalent diameter). The tapered sealing region 1109 allows the patient interface 1101 to be used for a patient having a nare size that is anywhere between about 4 mm and about 5 mm. For example, if a patient's nare size is 4.5 mm, the prongs 1105 are inserted in the nares such that the section of the sealing region 1109 having a diameter of 4.5 mm seals with their nares.

The prong sealing region 1109 may have different dimensions, and/or different amounts of taper. The length range for the sealing region may be between about 1 mm to about 10 mm. The length of the sealing region may be about 1 mm, 2 mm, 3 mm, 4 mm, 5 mm, 6 mm, 7 mm, 8 mm, 9 mm, or 10 mm. The diameter of the sealing region may be between about 2 mm and about 10 mm. The diameter of the sealing range may be about 2 mm, 3 mm, 4 mm, 5 mm, 6 mm, 7 mm, 8 mm, 9 mm, or 10 mm.

The ratio of the taper from the wider portion to the narrower portion may be about 1.1:1, 1.2:1, 1.3:1, 1.4:1, 1.5:1, 1.6:1, 1.7:1, 1.8:1, 1.9:1, or 2:1.

For example, the prong sealing region may taper from 10 mm to 9 mm, 9 mm to 8 mm, 8 mm to 7 mm, 7 mm to 6 mm, 6 mm to 5 mm, 5 mm to 4 mm, or 4 mm to 3 mm, 3 mm to 2 mm, for example. The taper may be steeper, for example, the prong sealing region may taper from 10 mm to 8 mm, 9 mm to 7 mm, 8 mm to 6 mm, 7 mm to 5 mm, 6 mm to 4 mm, 5 mm to 3 mm, or 4 mm to 2 mm, for example. The taper may be less steep, for example, the prong sealing region may taper from 10 mm to 9.5 mm, 9.5 mm to 9 mm, 9 mm to 8.5 mm, 8.5 mm to 8 mm, 8 mm to 7.5 mm, 7.5 mm to 7 mm, 7 mm to 6.5 mm, 6.5 mm to 6 mm, 6 mm to 5.5 mm, 5.5 mm to 5 mm, 5 mm to 4.5 mm, 4.5 mm to 4 mm, or 4 mm to 3.5 mm, 3.5 mm to 3 mm, 3 mm to 2.5 mm, or 2.5 mm to 2 mm for example.

Different sizes of the patient interface 101, 1101 may be provided, for which different prong sealing region dimensions may be utilized.

Figure 44:
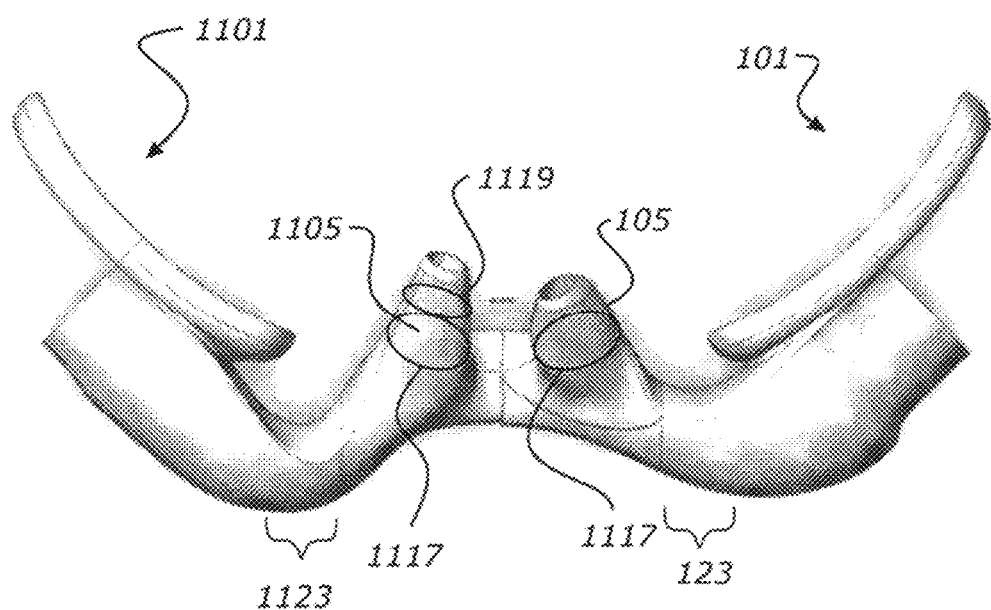
FIGS. 44 and 45A show a comparison between the second embodiment patient interface and prong design (on the left side of the figure) and the first embodiment patient interface (right side).
Figure 45A:
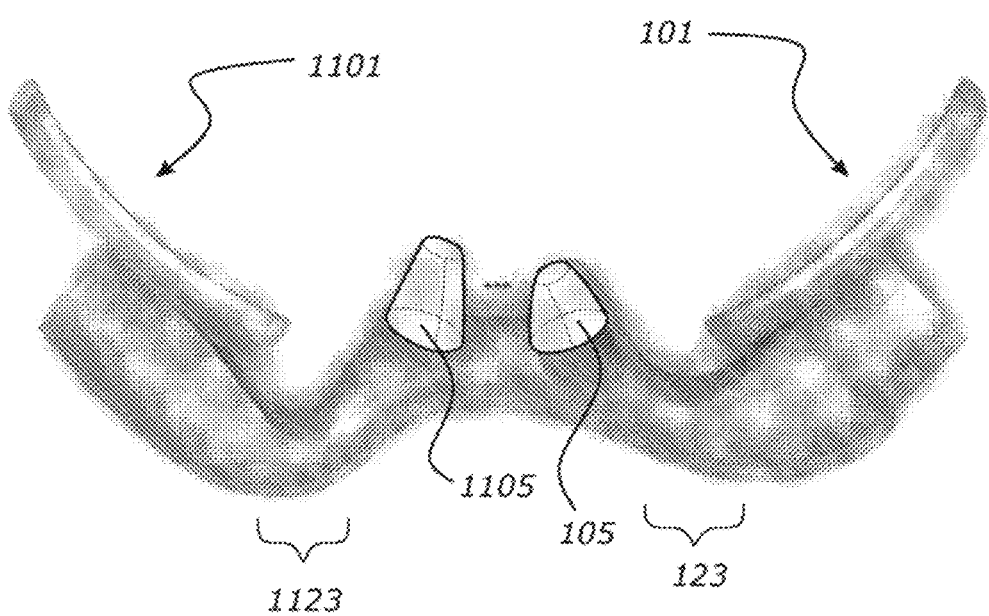
Figure 45B:
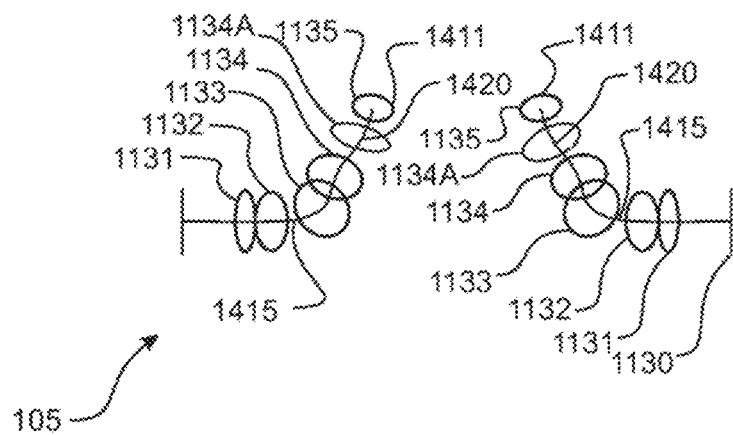
FIGS. 45B and 45C show the geometry of the prongs of the interface of FIG. 3 illustrated with swept lines that represent the prong trajectory.
Figure 45C:
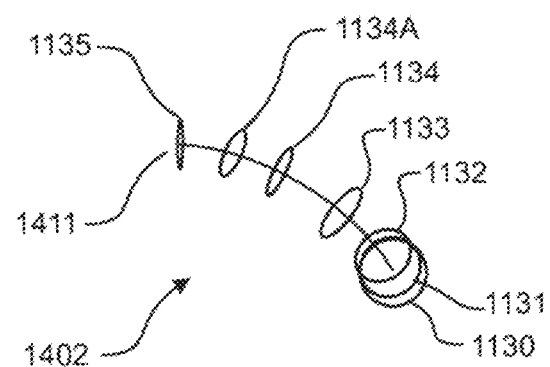

FIGS. 44 and 45A show a comparison between the second embodiment patient interface 1101 and prong design (on the left side of the figure) and the first embodiment patient interface 101 (right side). FIG. 44 shows ovals 1117, 1119 that are highlighted on the prongs. The oval 1117 near the inlet 1105 is larger than the oval 1119 near the outlet 1108. The region between the two ovals 1117, 1119 that are highlighted on the left prong is the additional prong sealing region 1109 that is not present in the first embodiment patient interface 101. FIG. 45A shows the lumen of each prong.

Figure 36:
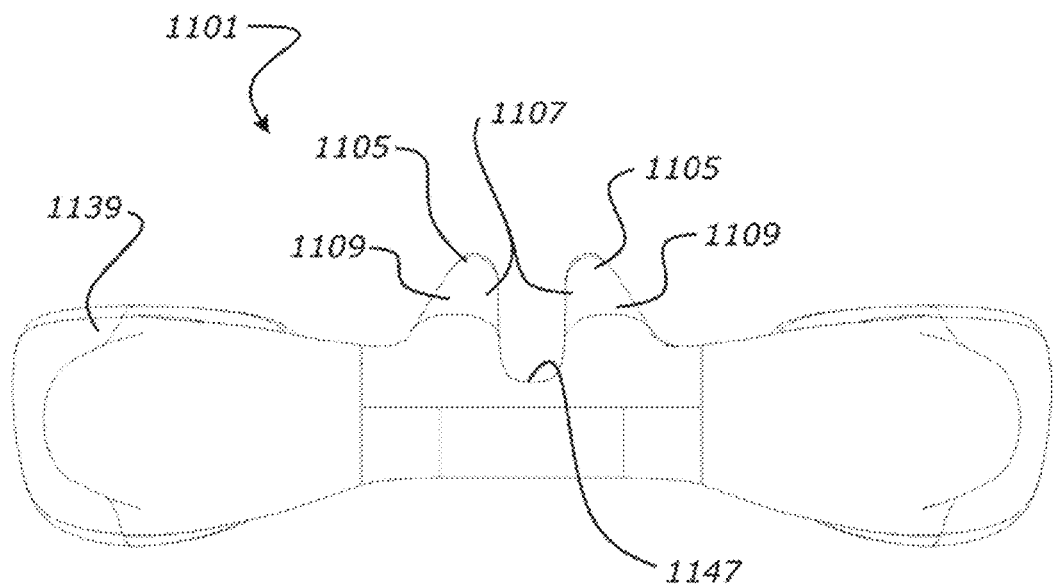
FIG. 36 is a front view of the patient interface of FIG. 34.
Figure 37:
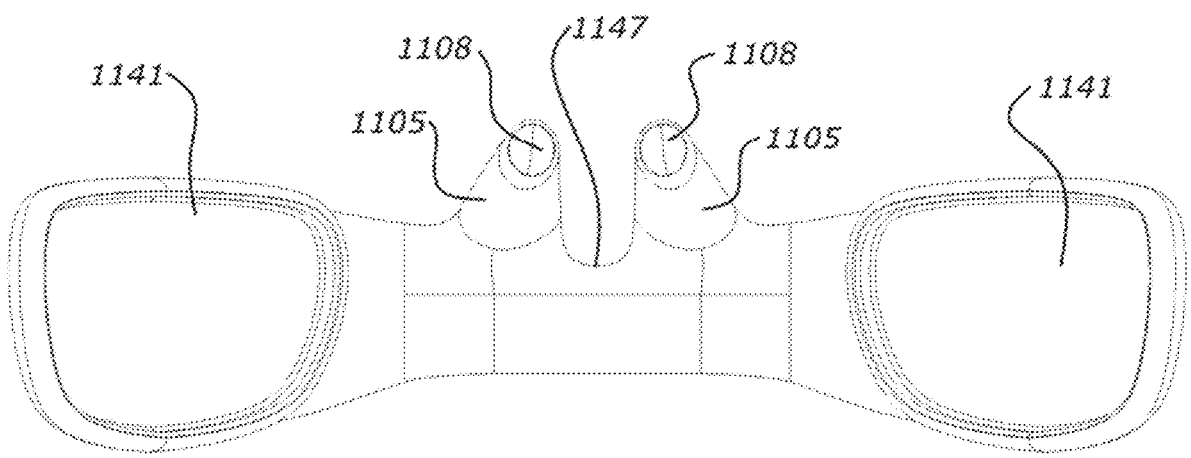
FIG. 37 is a rear view of the patient interface of FIG. 34.
Figure 38:
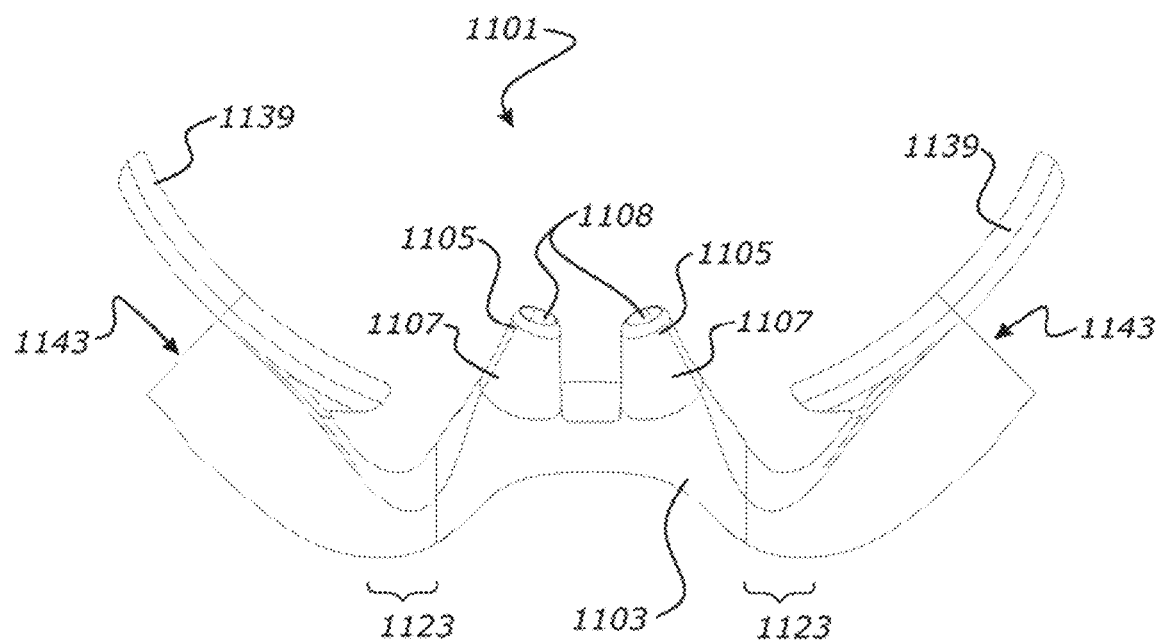
FIG. 38 is a top view of the patient interface of FIG. 34.
Figure 39:
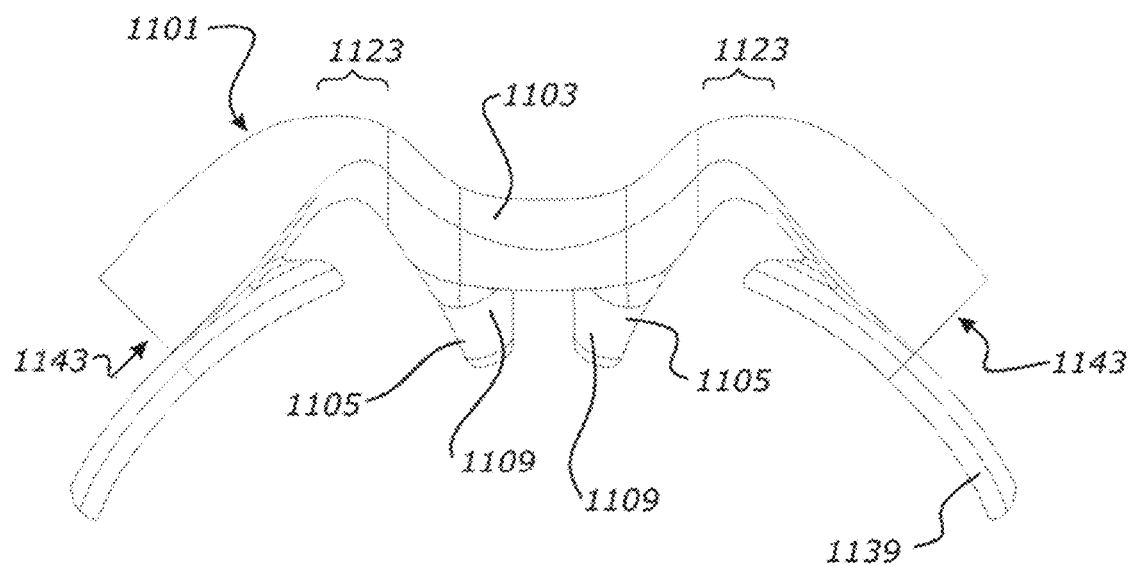
FIG. 39 is an underside view of the patient interface of FIG. 34.
Figure 40:
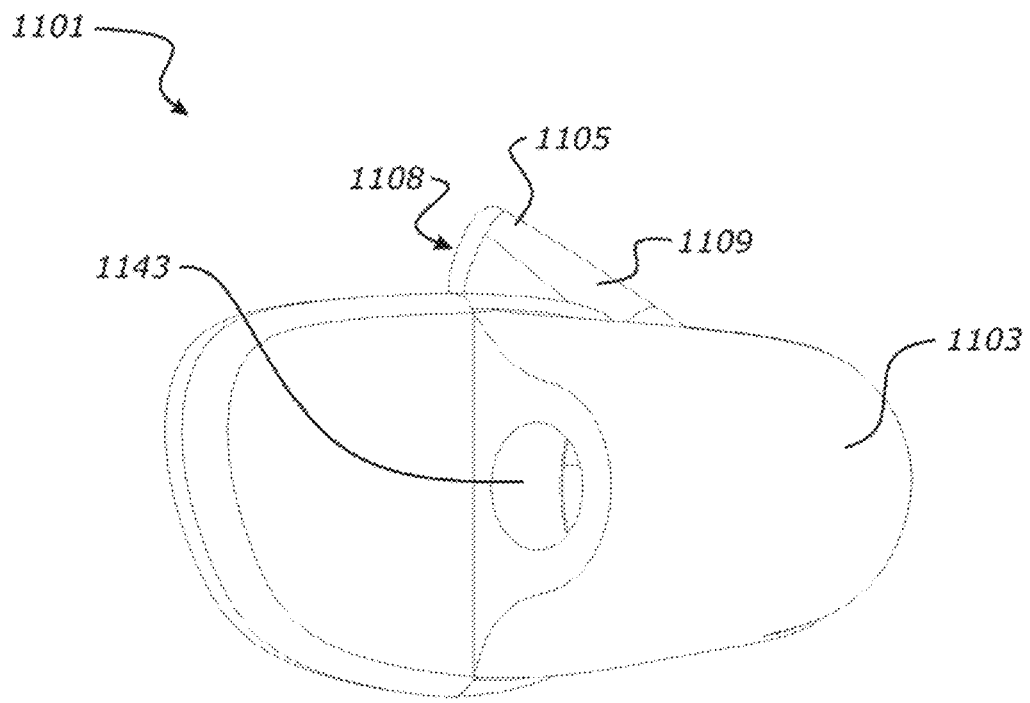
FIG. 40 is a left side view of the patient interface of FIG. 34.
Figure 41:
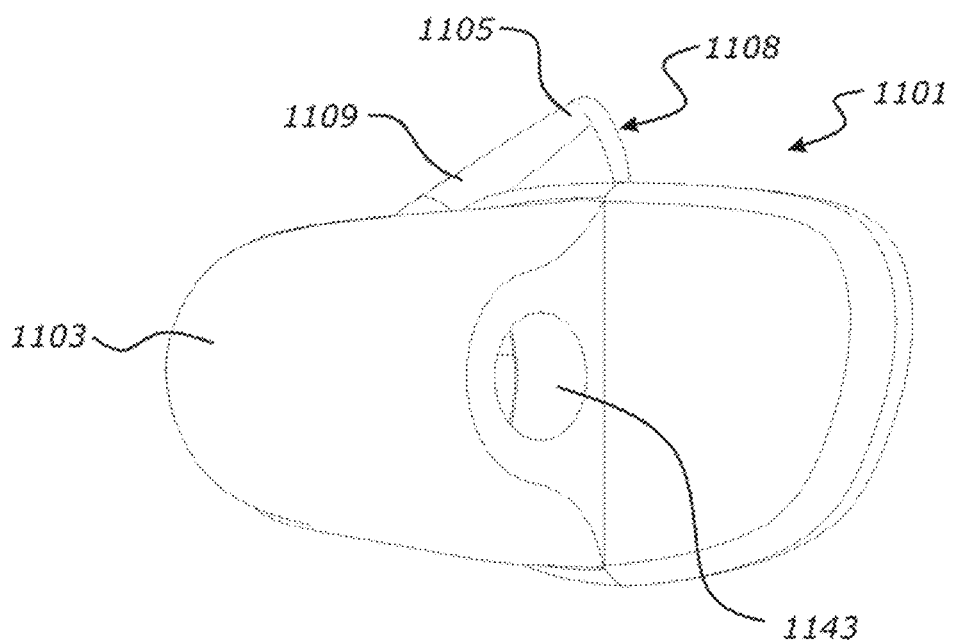
FIG. 41 is a right side view of the patient interface of FIG. 34.
Figure 42:
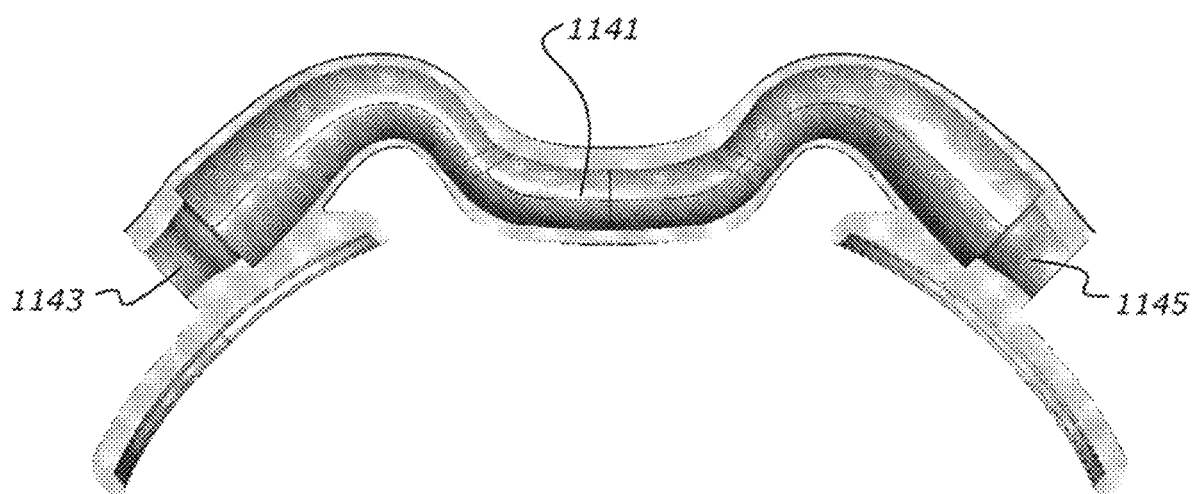
FIG. 42 is a cross-section of the patient interface of FIG. 34.
Figure 43:
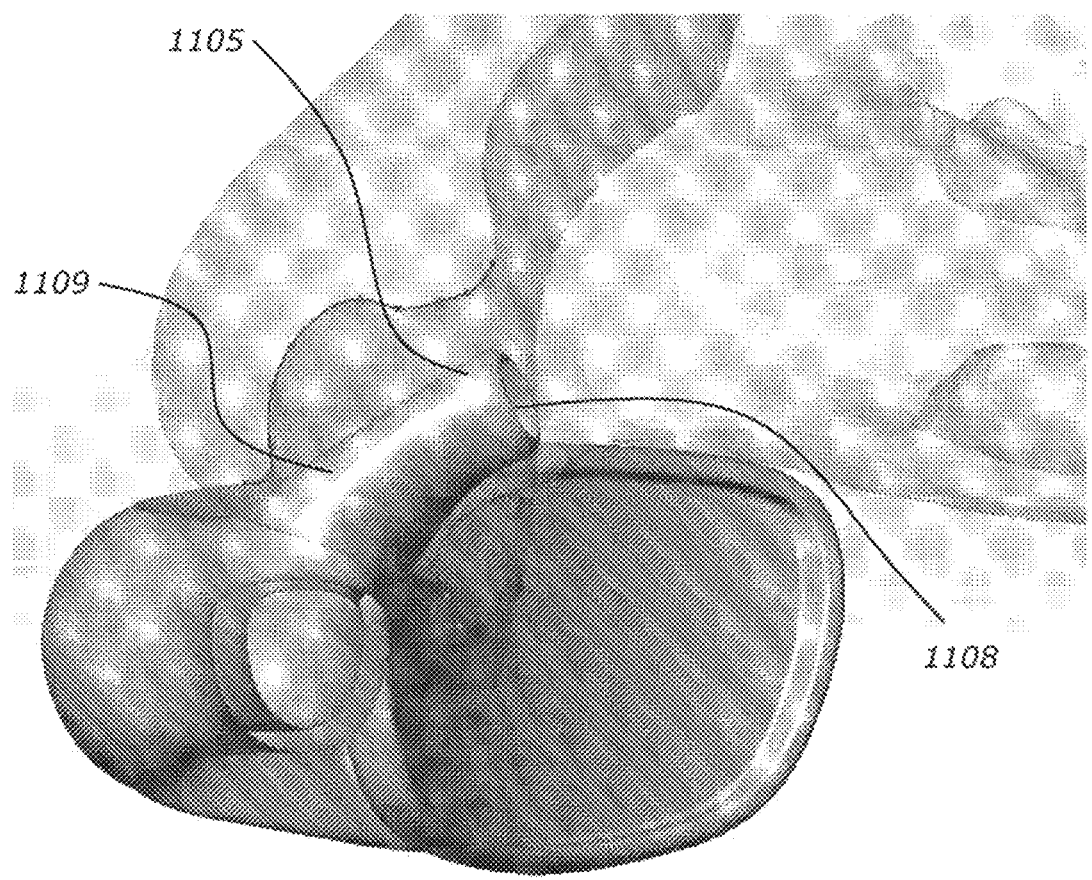
FIG. 43 is a cutaway view of the patient interface of FIG. 34 in a user's nare.

In this embodiment, the nasal prong 1105 is shaped to avoid contact with the septum of a user at the base of a user's nose. With reference to FIGS. 36 and 37, the patient interface 1101 has a recess 1147 between the prongs 1105 to avoid contact with the septum. In this example embodiment, the recess 1147 is shown as a scalloped recess, similar to the previously described patient interface 101. However, the adjacent section of the wall of each nasal prong 1105 is substantially straight. The recess 1147 has a smooth transition between each of the nasal prongs 1105 and the recess 1147.

Similar to the earlier described embodiment, the shape of the recess 1147 can ensure clearance of the cannula from the patient's septum. This spacing allows the patient interface to seal with the patient's nares without the portion between the prongs touching or impinging upon the patient's septum. This reduces contact pressure on the septum and possible septum damage. However, it should be noted that in some situations, the portion of the patient interface between the nasal prongs may contact the septum. In this situation, the recess would conform to the patient's septum and ensure only a small amount of pressure is applied to the septum. The recess conforms by using a thin wall thickness compared to other regions of the base section or prongs of the patient interface, which reduces the pressure the recess applies to the septum. As well as this function, the thinness of this region may also allow the prongs 1105 to have some movement in the inward direction (towards each other) and/or the outward direction (away from each other) which may help fitting the prongs 105 to some patients.

The conduits or tubes 201a, 201b used with the patient interface 101, 1101 attach to either side of the patient interface. There are connectors at either end of the conduits 201a, 201b that respectively connect to the inspiratory and expiratory conduits of a CPAP system. In one embodiment, the connectors are identical. In an alternative embodiment, the connectors may be different. Identical connectors allow either tube 201a, 201b to connect to the inspiratory or expiratory conduits of the system, and to be regularly swapped for patient comfort, to reduce the potential for pressure or therapy-related injury, and/or for more effective therapy. This present technology is versatile in that the tubes 201a, 201b are flexible and can easily connect, in many orientations, to the inspiratory/expiratory conduits of the system. It should be appreciated that rather than connect directly to the inspiratory/expiratory conduits of the system, the inspiratory and expiratory tubes of the interface may instead connect to an intermediate connector, commonly called a wye-piece, which is in turn connected to the system inspiratory/expiratory conduits. It should further be appreciated that in such a system, the wye-piece may have 4 connection points (and thus be "X" or "K" shaped, rather than the more common "Y" shape).

The tubes 201a, 201b are generally expected to extend laterally from the interface 101,1101. If a patient is lying on their side, breastfeeding, or undergoing kangaroo care, because the tubes are flexible, the tube on the bed-facing side or parent-facing side can be moved easily and attached elsewhere to the interface or retention system (via hook/loop or other mechanical or adhesive fastener). As a result, the CPAP therapy will not be disrupted and comfort for the patient and careers can be improved. Furthermore, as described later, the interface tubes 201a, 201b may be attached to a part of a chinstrap headgear via hook and loop fasteners which would take some load off the securement system. Details of a suitable tube are described below.

Although medical tubes exist in the prior art, it is recognised that there are problems with current medical tubes that extend between a respiratory component and a patient interface. Large diameter tubes are often used because decreasing the diameter of a medical tube can result in an increase in resistance to flow. However, some of these larger diameter tubes can also have high resistance to flow. Large medical tubes can also be heavy, bulky, and inflexible in use. They also may not be aesthetically pleasing to a doctor, nurse, or family member (or other carer), which can result in the treatment not being readily accepted by doctor, nurse, or family member (or other carer). Because medical tubes stretch between a respiratory component and a patient interface, they can drag on the patient interface, causing discomfort to the patient and/or disrupting the treatment. Tubes can be noisy when moved or pushed against surfaces, causing the treatment to be obtrusive to the patient and/or a carer.

Some medical tubes may not provide good crush resistance. As a result, resistance to flow can be impaired following a crushing event in which the shape and/or lumen of the tube is disrupted. Similarly, the medical tube may not recover from the event but may continue to provide impaired treatment until intervention from the user or may be rendered useless.

Figure 33:
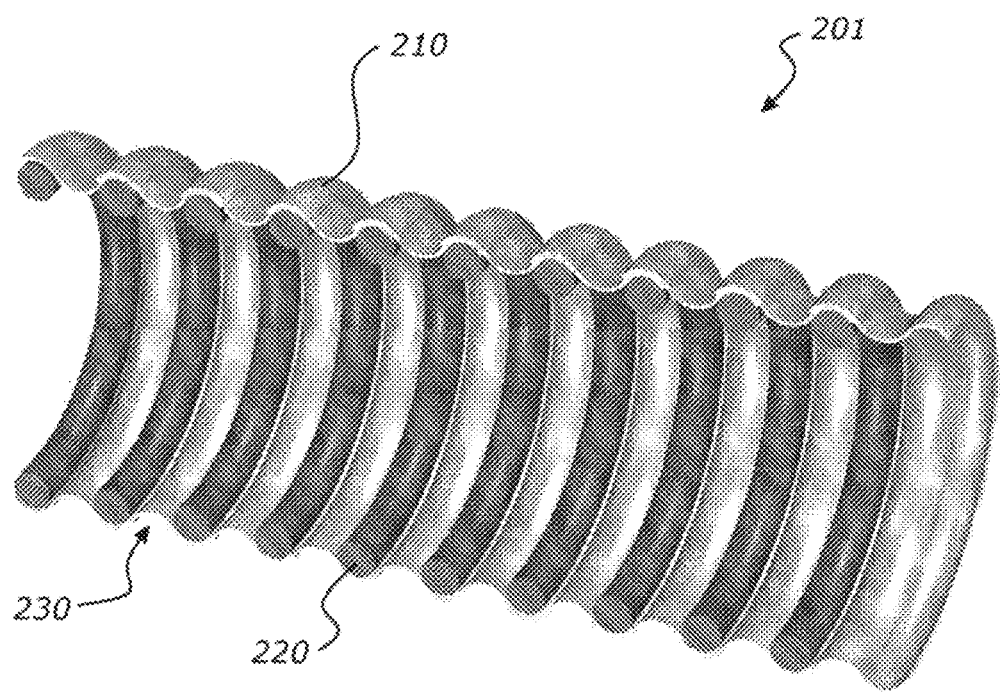
FIG. 33 shows a perspective, cross-sectional view of the conduit.
Figure 34:
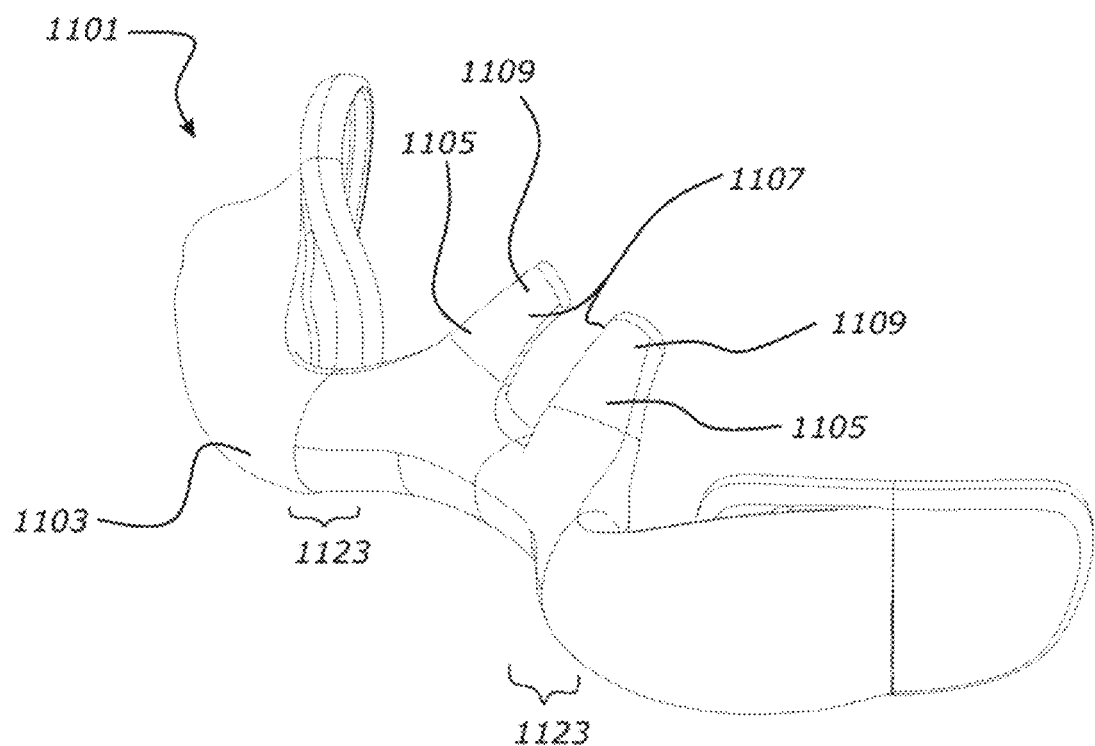
FIG. 34 is a perspective view from the front of another embodiment of a patient interface.
Figure 35:
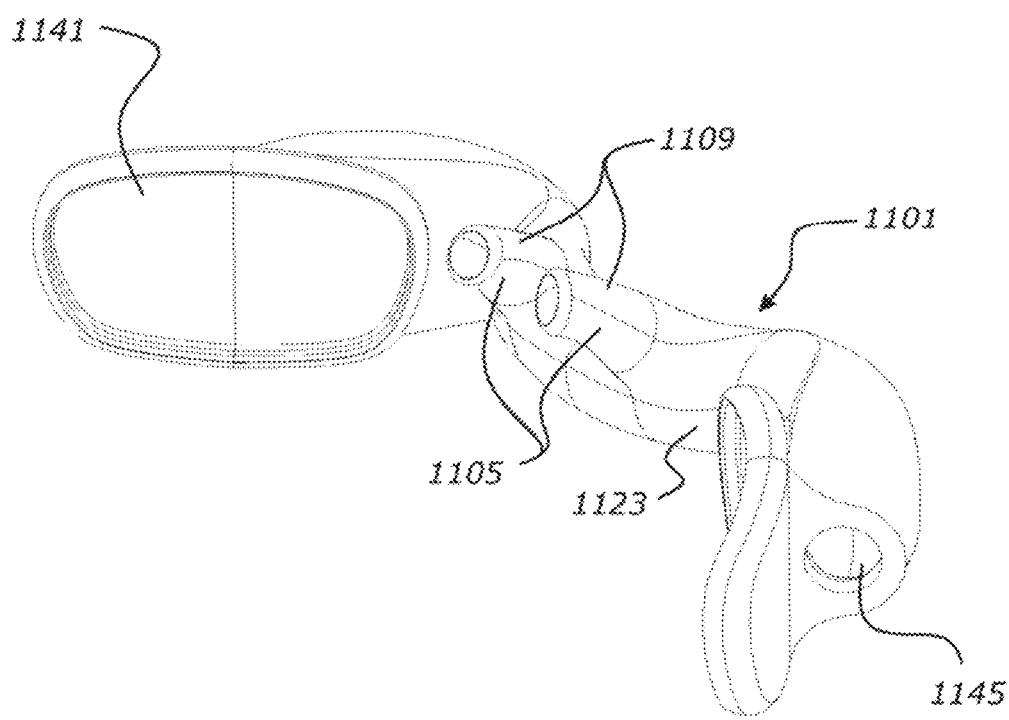
FIG. 35 is a perspective view from the rear of the patient interface of FIG. 3.

FIG. 33 shows an embodiment of the conduit (medical tube) 201 configured to extend between two components of the respiratory system. Where reference numeral 201 is used to refer to the conduit or medical tube in the description, that conduit or tube may be the inspiratory conduit 201a and/or the expiratory conduit 201b. The conduit may be a conduit as described in PCT application PCT/NZ2015/050163, published as WO2016048172, the contents of which are incorporated herein by reference. The medical tube 201 can comprise an elongate film 210 and an elongate reinforcing member 220 that are extruded and spirally wound to form the medical tube 201. In some embodiments, the elongate film 210 can be configured to be breathable. The breathable characteristic of the film 210 refers to a film that is highly permeable to water vapor and substantially impermeable to bulk flow of any liquid water and the bulk flow of gases from inside of the medical tube through to ambient air. The elongate film 210 being breathable allows condensate formed at, for example, the patient interface 101, or the medical tube 201 to be vaporized (e.g., by a heater wire) and transferred through the elongate film 210 to the surrounding atmosphere if the condensate drains back to the medical tube 201.

The elongate reinforcing member 220 can provide rigidity and/or structural support to the elongate film 210. In some embodiments, the elongate reinforcing member 220 can comprise at least one wire, which can provide a heating and/or sensing component to the medical tube 201.

In certain embodiments, a breathable material has a moisture (water) vapor transmission rate greater than or equal to 650 g/m2/day (or thereabout) when measured according to Procedure B of ASTM E96 (using the upright cup method at a temperature of 23° C. and a relative humidity of 50%). The thickness of the breathable film can provide sufficient breathability and flexibility as well as strength and robustness to the medical tube.

In some embodiments, the film can be made from a breathable thermoplastic material, such as a thermoplastic elastomer (or TPE as defined by ISO 18064:2003 (E)), a thermoplastic polyurethane (or TPU as defined by ISO 18064:2003 (E)), a thermoplastic polyester, or other material with elastomeric properties. The elongate reinforcing member can be made from, for example, a TPU. The materials disclosed are not meant to be limiting but rather are examples of possible materials that can be used. The materials can be chosen such that a bond is formed between the elongate film and the elongate reinforcing member. The materials can be chosen such that when the medical tube moves and/or contacts other surfaces, it remains quiet and unobtrusive. Different materials and/or material combinations can fall within the scope of this disclosure.

A profile of the film can be controlled so that when the medical tube is bent, the film does not collapse into the lumen of the tube. The profile can comprise an inwardly biased profile between adjacent windings of the reinforcing member. The term "inwardly biased," as herein described, generally refers to a configuration in which the film extending between adjacent windings of the reinforcing member drapes toward the center of the lumen when the medical tube is not subject to deformational strain (that is, the medical tube is in a neutral position). The dimensions of the profile can allow the film to drape to a maximal level between adjacent windings of the reinforcing member without protruding into the lumen of the medical tube, thus minimising the effect bending the medical tube may have on resistance to flow.

Each tube 201 of the present disclosure has a respiratory component end 203 (expiratory/inspiratory side) that connects to a CPAP therapy delivering device and a patient interface end 205 that, in this present disclosure, connects to one side of the patient interface 101,1101.

The patient interface end 205 may be rigid compared to an adjacent section of the tube 201. Alternatively, the patient interface end 205 may be soft, or less rigid, compared to an adjacent section of the tube 201. For example, the patient interface end 205 may comprise a flexible, supple, or compliant material. The patient interface end 205 of the conduit may be a separate component to the tube 201, or may be an integral part of the tube 201. The patient interface end 205 of the conduit may be an overmoulded component, such as an overmoulded connector. The connector may be or comprise a silicone or elastomer material. An embodiment having a soft patient interface end 205 increases patient comfort, for example, when the patient's face is on the patient interface end, which may occur when the patient is lying on their side or front.

In the embodiment shown, at the respiratory component end there is a short sleeve or boot attachment 301 on the region of the interface tube 201 where the connector and interface tube 201 meet. The sleeve 301 may be held in place in any suitable manner, such as a threaded connection, adhesive and/or glue, overmoulding, friction and/or interference fit, or other mechanical attachment means. In one example embodiment, the sleeve 301 is held in place over a flange 202 on the tube. The sleeve 301 has a corresponding flange 303 that engages with the flange 202 of the tube. The connector flange 202 is received by a recess 304 in the sleeve 301. The sleeves 301 preferably comprise a soft, elastomeric material. In some embodiments, the sleeves 301 may be coloured. This colouring provides the benefits of being aesthetically pleasing. Moreover, coloured sleeves may be used to indicate different sizes of cannula, i.e. colour-coded sizes. These sleeves protect the thread of the tube 201 in the covered regions and also reduce the potential for leaks and contamination. The sleeves also increase the strength of the joint between the connector and the tube 201.

Figure 16:
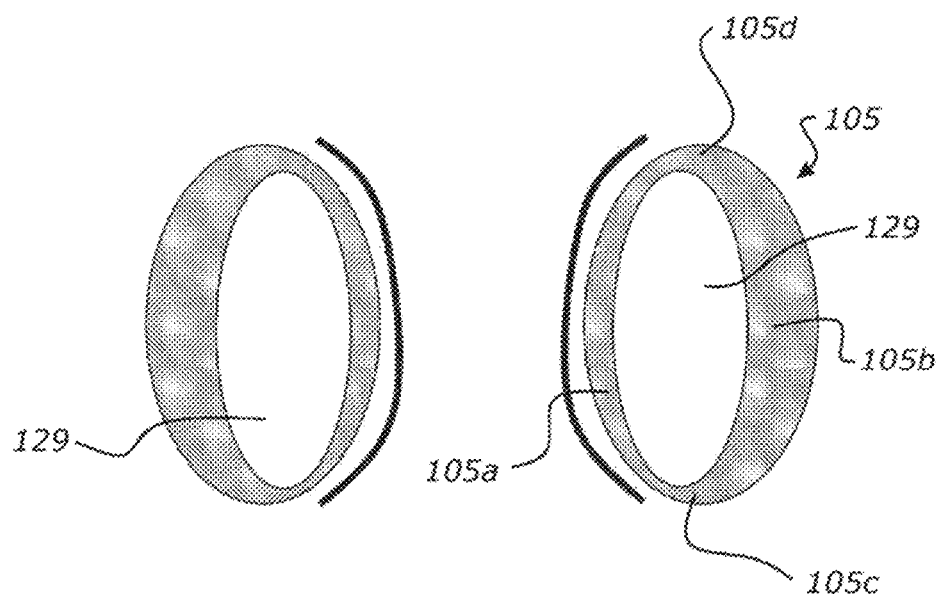
FIG. 16 is a schematic horizontal cross-section depicting the wall thickness of the prong outlet whilst the prongs are sealing in a patient's nose.
Figure 17:
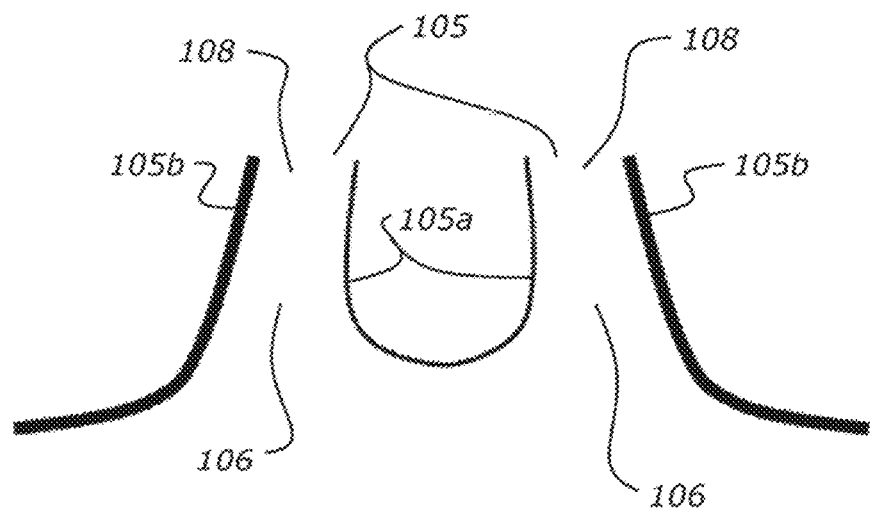
FIG. 17 is a schematic vertical cross-section depicting the wall thickness of the prong outlet whilst the prongs are sealing in a patient's nose.

In one embodiment, the thickness of the wall of the nasal prong 105 may be variable around its circumference or perimeter. As shown in FIGS. 16 and 17, the nasal prong 105 may have an inner wall 105*a* and an outer wall 105*b*. The inner wall 105*a* has a thickness that is thinner than a thickness of the outer wall 105*b*. The inner wall is the region of the nasal prong near to the patient's nasal septum. The outer wall is the opposite wall. The thinner inner wall reduces pressure on the patient's septum. In alternative embodiments, other regions of the outlet wall 105*c*, 105*d*, may vary in thickness and the flow passage may be in another configuration (i.e. may have a different angle or cross-sectional shape).

The nasal prong 105 has a front wall 105*c* extending between the inner wall and the outer wall, the inner wall having a thickness that is thinner than a thickness of the front wall. The nasal prong 105 has a rear wall 105*d* extending between the inner wall and the outer wall, the inner wall having a thickness that is thinner than a thickness of the rear wall.

FIG. 17 shows the wall thickness with regards to the entire prongs 105. The wall thickness is preferably thinner on the regions (inner) of the prong that are in contact with the septum, shown by thinner lines in the figure. The wall is thicker on the outer sides of the prongs 105, shown by thicker lines in the figure. The thicker wall 105*b* here gives the necessary rigidity to the prong to stop undesirable prong kinking. The prongs 105 must be rigid enough to be repeatedly and effectively sealingly inserted into the patient's nare, without causing (or at least minimizing the risk of) any damage or pressure injuries to the patient over the hours to weeks of use.

In one embodiment, the nasal prong 105 is shaped to avoid contact with the septum of a user at the base of a user's nose.

Figure 5:
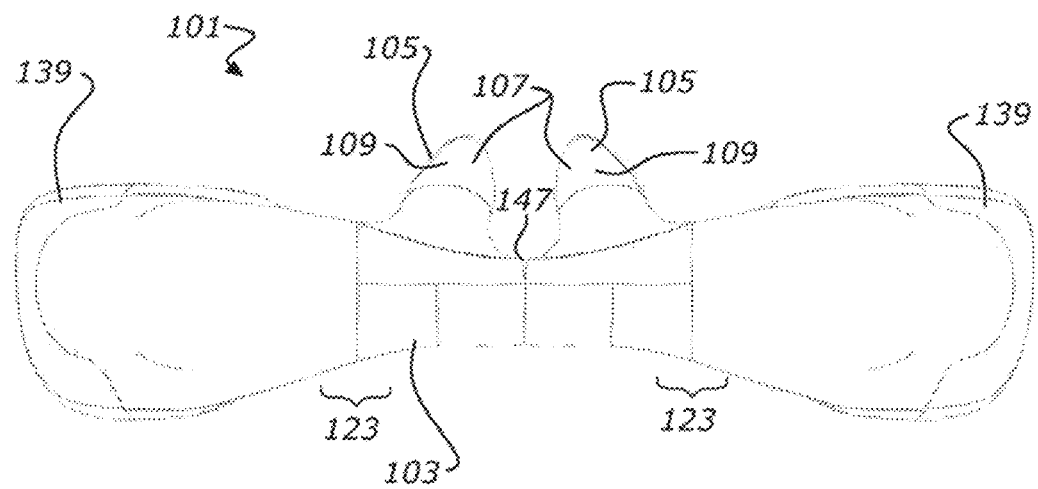
FIG. 5 is a front view of the patient interface of FIG. 3.
Figure 6:
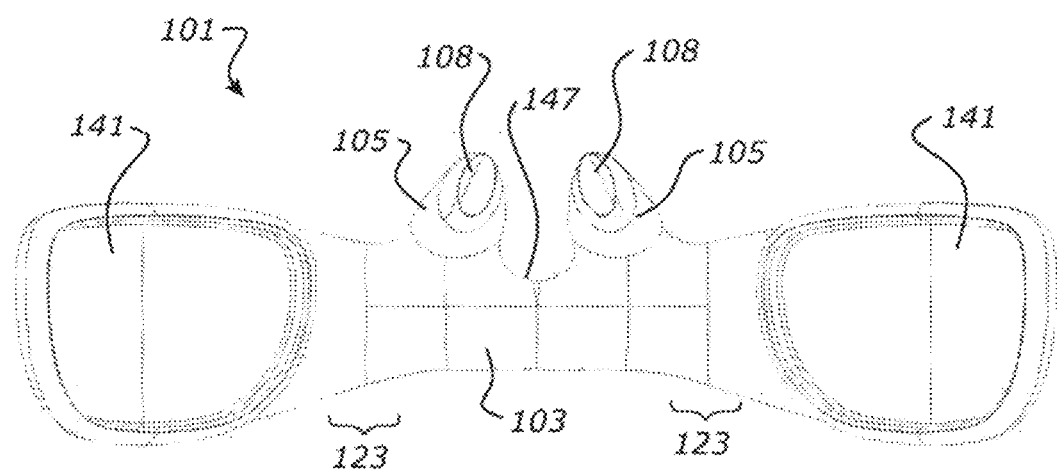
FIG. 6 is a rear view of the patient interface of FIG. 3.
Figure 7:
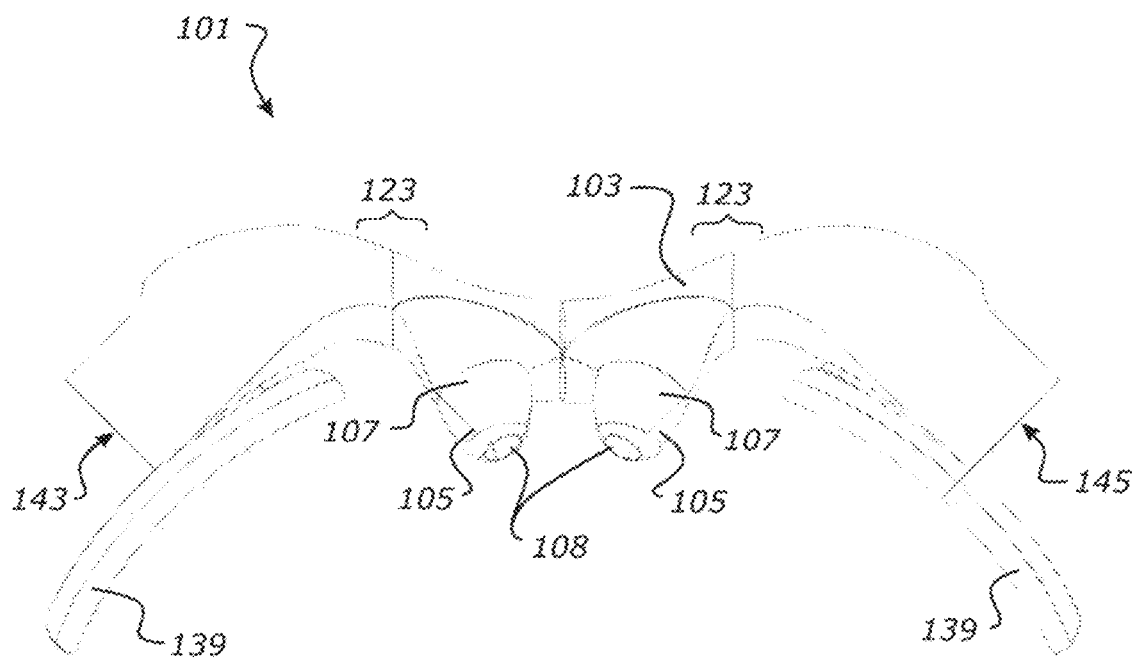
FIG. 7 is a top view of the patient interface of FIG. 3.
Figure 8:
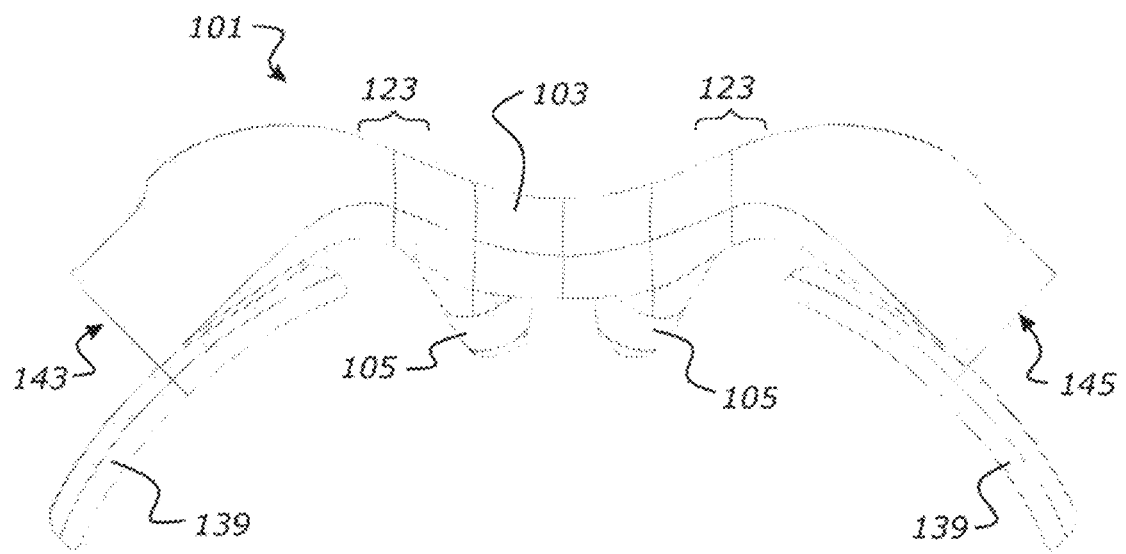
FIG. 8 is an underside view of the patient interface of FIG. 3.
Figure 9:
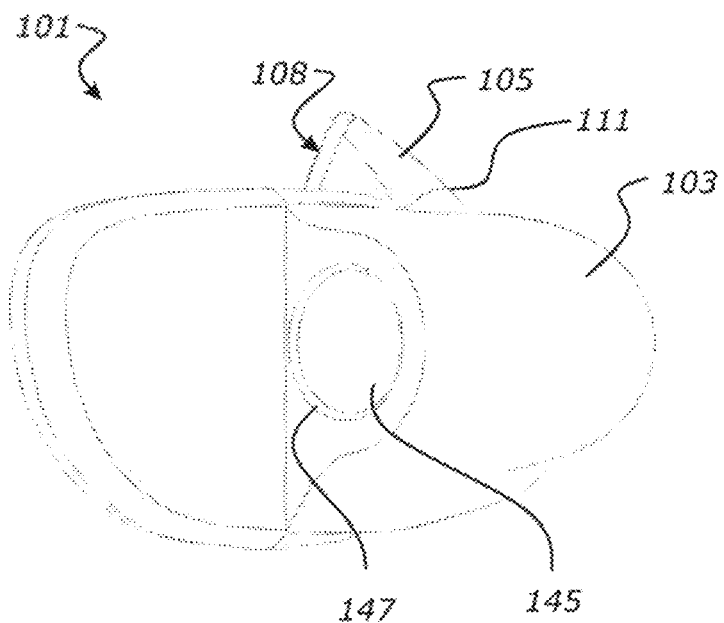
FIG. 9 is a left side view of the patient interface of FIG. 3.
Figure 10:
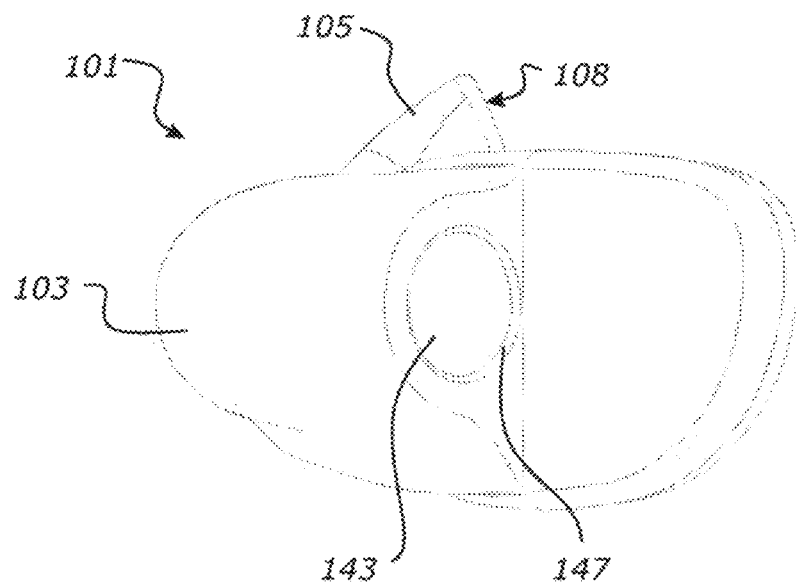
FIG. 10 is a right side view of the patient interface of FIG. 3.

With reference to FIG. 5, the patient interface 101 has two nasal prongs 105, where the two prongs have a recess 147 between the prongs 105 to avoid contact with the septum. In this example embodiment, the recess 147 is shown as a scalloped recess. It should be appreciated by one of skill in the art that any suitable shape of recess may be used so long as it reduces contact between the interface and the patient's septum, or so long as it reduces pressure on the patient's septum as compared to a horizontal or straight body connection between the bases of the prongs. The recess has a smooth transition between each of the nasal prongs 105 and the recess, and is shaped like the bottom of a tear drop. This curvature can ensure septum spacing with the cannula. This spacing allows the patient interface to seal with the patient's nares without the portion between the prongs touching or impinging upon the patient's septum. This reduces contact pressure on the septum and possible septum damage. However, it should be noted that in some situations, the portion of the patient interface between the nasal prongs may contact the septum. In this situation, the recess would conform to the patient's septum and ensure only a small amount of pressure is applied to the septum. The recess conforms by using a thin wall thickness compared to other regions of the base section or prongs of the patient interface, which reduces the pressure the recess applies to the septum. As well as this function, the thinness of this region may also allow the prongs 105 to have some movement in the inward direction (towards each other) and/or the outward direction (away from each other) which may help fitting the prongs 105 to some patients.

Figure 20A:
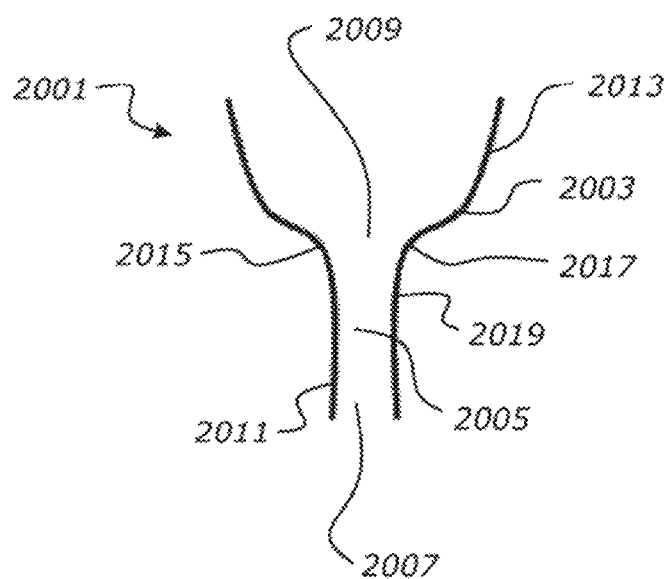
FIG. 20A is a schematic view of one embodiment of a prong moulded in wine glass shape.
Figure 20B:
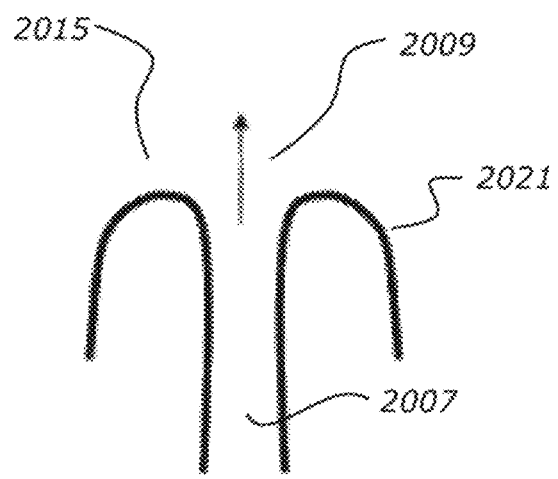
FIG. 20B is a schematic view of the prong of FIG. 20A in a rolled configuration.

With reference to FIGS. 20A and 20B, an alternative embodiment of the nasal prong 2001 is shown. In this embodiment, the nasal prong 2001 comprises a generally annular wall 2003 defining a lumen 2005. When viewed from above, the wall may be generally circular, generally elliptical, generally oval, or any other suitable shape. The lumen 2005 has a gas inlet 2007 for fluid communication with a supply of breathable gas. The lumen 2005 has a gas outlet 2009 configured to direct a flow of gas towards a nare of the user's nose. The wall has an inlet end 2011 and an outlet end 2013. The wall 2003 has a substantially flexible portion 2015. The substantially flexible portion 2015 is configured to roll over itself, or bend over itself, when the outlet end 2013 is moved towards the inlet end 2011.

In some embodiments, a portion of the wall 2003 at or near the inlet end of the wall is stiffer than the substantially flexible portion.

The substantially flexible portion 2015 is configured to roll over the exterior surface of the wall.

The wall includes a rounded ledge 2017 between the flexible portion and the inlet end. A portion 2019 of the wall between the rounded ledge 2017 and the inlet end has a substantially constant diameter along its length. This portion has a relatively small diameter compared to the outlet end diameter.

A portion of the wall between the rounded ledge and the outlet end has a substantially constant diameter along its length.

With reference to FIG. 20B, when the flexible portion is rolled over, the flexible portion provides a sealing surface 2021 configured to seal the nare of the user's nose. With reference to FIG. 20A, when unrolled, prong is wine-glass shaped.

The patient interface may be secured to the patient's face using a securement system.

The securement system comprises a two-part releasable attachment or connection arrangement. The two-part releasable attachment or connection arrangement may be a two-part releasable attachment or connection arrangement as described in PCT application PCT/NZ2011/000218, published as WO2012/053910, the contents of which are incorporated herein by reference. The reference herein to a patient interface, second patch, or patient interface patch, and similar terms, will be understood to be similar to the reference to a user interface or user interface patch in WO2012/053910. The releasable connection arrangement acts between a pair of patches that are affixed to the patient and the patient interface respectively. The first patch is a dermal patch that is adhered or otherwise attached to the patient's skin. The dermal patch has a user side that faces the user's skin and an interface side that faces the patient interface. The user side of the dermal patch may be attached to the skin of a user by a dermatologically sensitive adhesive, such as a hydrocolloid. The patient interface side of the dermal patch is provided with the first part of the two-part releasable attachment or connection system. In an alternative embodiment, the first patch may be attached to, or attachable to, an item being worn by the user. The item may be part of a securement system, such as the securement system described herein. For example, the item may be a bonnet, or a headgear strap (including a strap that extends down the side of the patient's cheek like side burns, or chin strap). The first patch may be attachable using hook and loop fasteners, magnets, or adhesive.

The second patch is a patient interface patch. The second patch also has a patient side and an interface side. The patient side of the second patch is disposed adjacent the dermal patch when the system is engaged. The complimentary second part of the two-part releasable attachment or connection system is affixed to the patient side of the second patch, so that the respective parts of the two-part releasable attachment or connection system are easily engagable when the patches are brought together. The interface side of the second patch is affixed to the patient interface. The second patch may be integrated with, formed integrally with, or suitably adhered to the patient interface.

The two-part releasable attachment or connection arrangement may comprise a hook and loop material (such as Velcro™), a magnet (or ferrous material to attract with a magnet) or an array of magnets disposed on the respective patches with the poles suitably arranged, an adhesive arrangement that is activated when the patches are urged together or another suitable releasable suitable coupling. The interface side of the dermal patch may have one of a hook or a loop material, and the patient side of the second patch may have the other of the hook or loop material, such that the dermal and second patches are releasably attachable or connectable to each other.

Figure 21:
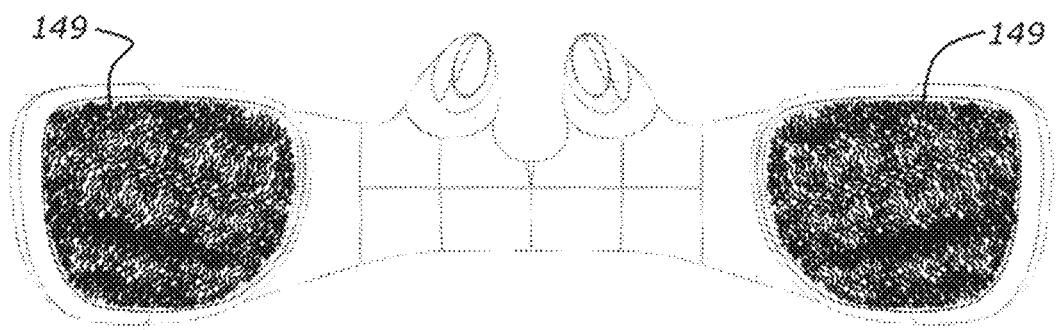
FIG. 21 is a top rear perspective view of a nasal cannula arrangement with a backing component comprising a lip and a second patch on a rear surface of the backing component.
Figure 22:
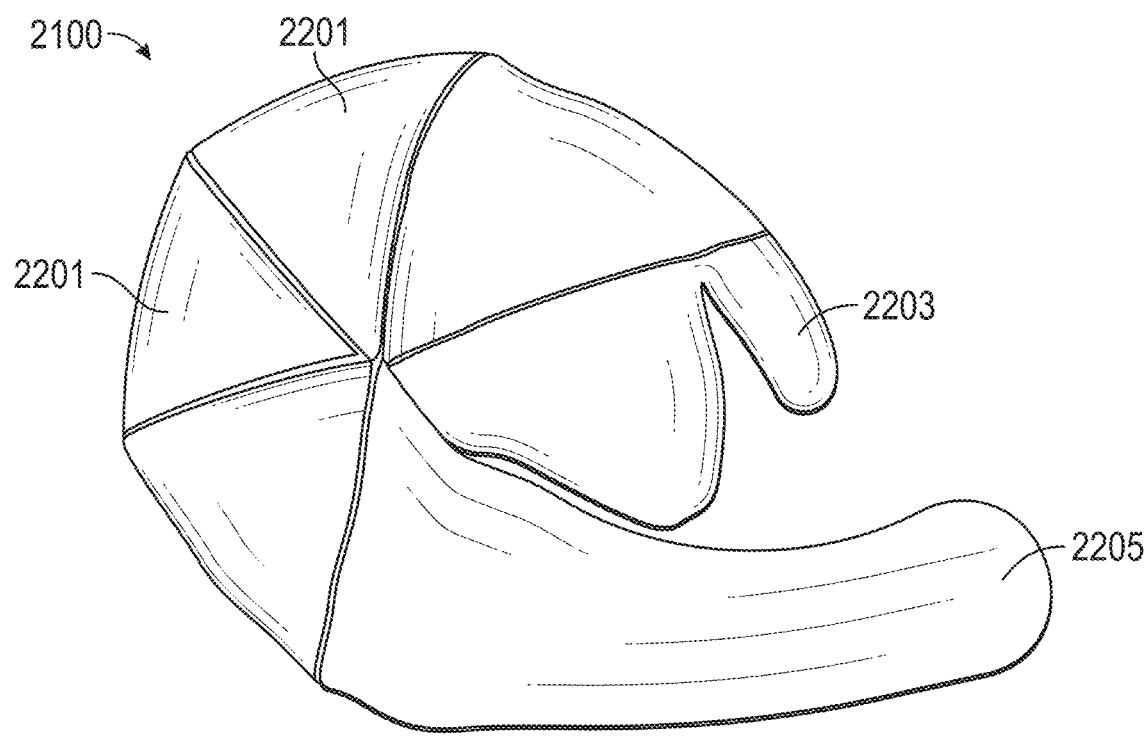
FIG. 22 shows an embodiment of an adjustable bonnet.

With reference to FIG. 21, the rear surface 141 can be initially provided without a second patch, i.e. the surface 141 is configured to receive or retain a second patch 149. Such a second patch 149 may be connected to the rear surface 141 by an adhesive or other suitable connection as is known in the art (such as by adhesive, ultrasonic welding, and/or co-moulding or overmoulding). Once the patch is then in position, it is ready to be connected to or receive a dermal patch.

In some embodiments, the first patch and second patch may take the form of a fixation structure, such as the fixation structure described in PCT application PCT/NZ2016/050050, published as WO2016/159783, the contents of which are incorporated herein by reference. FIGS. 72A-72B illustrate an example configuration for the fixation structure 300 to secure the tube. The illustrated fixation structure 300 includes a body 302. FIG. 72A illustrates a interface-facing region of the body 302, and FIG. 72B illustrates a patient facing region of the body 302. The body 302 is formed from or includes an adhesive material to adhere to the patient's face in use. In the illustrated configuration, the body 302 is formed from or includes a hydrocolloid-based adhesive material. The body 302 includes a first edge 304 that faces towards the nose or mouth of a patient in use and a second edge 306 that faces away from the patient's nose or mouth in use. The opposed third and fourth edges 308A, 308B extend between the first and second edges 304, 306. As illustrated, in some configurations, the third and fourth edges 308A, 308B are curved. In some configurations, the curves are at least partially concave with respect to the third and fourth edges 308A, 308B. The curves can substantially correspond with a contour of an eye or an eyelid. When forces are exerted on the body 302 of the fixation structure 300 that would urge the body 302 towards the eye or eyelid, the curvature increases the tendency of the body 302 to cup or move around the contour of the lower eyelid and decreases the tendency of the body 302 to move into or near the eye or eyelid.

The third and fourth edges 308A, 308B may project farther from a centerline or center portion of the body 302 at parts of the third and fourth edges 308A, 308B that are proximal to the first and second edges 304, 306 than the third and fourth edges 308A, 308B project from the centerline or center portion of the body 302 at parts of the third and fourth edges 308A, 308B that are distal from the first and second edges 304, 306 (for example, central portions of the third and fourth edges 308A, 308B). In some configurations, portions of the third and fourth edges 308A, 308B proximal to the second edge 306 may project farther from the centerline or center portion of the body 302 than do portions of the third and fourth edges 308A, 308B proximal to the first edge 304.

The body 302 includes a pair of separable extensions 332A, 332B. In the illustrated configuration, the separable extensions 332A, 332B are formed from the same material as the body 302. In some configurations, the separable extensions 332A, 332B are formed from a different material than the body 302. The separable extensions 332A, 332B may be substantially wing-shaped. The separable extensions 332A, 332B are at least partially linked to the body 302 at the third and fourth edges 308A, 308B of the body 302 and may project outwardly from the body 302. The separable extensions 332A, 332B are linked to the body 302 by perforated sections 330A, 330B. The perforated sections 330A, 330B can be torn to allow the separable extensions 332A, 332B to be separated from the body 302. In some configurations, one of the perforated sections 330A, 330B can link the body 302 with the separable extensions 332A, 332B. In some configurations, multiple perforated sections 330A, 330B (for example, two, three, or four perforated sections) can link the body 302 with the separable extensions 332A, 332B.

The separable extensions 332A, 332B retain or encapsulate the tube. As shown in FIG. 72A, on the sides of the separable extensions 332A, 332B corresponding to the interface-facing region of the body 302, the separable extensions 332A, 332B include adhesive layers 334A, 334B to retain the tube. The adhesive layers 334A, 334B may be formed from or include adhesives that are appropriate for adhering to plastic feeding tubes, including, but not limited to, hydrocolloid-based adhesives and acrylic-based adhesives. One or more of the adhesive layers 334A, 334B may be covered by backing layers to protect the adhesive nature of the adhesive layers 334A, 334B.

In some embodiments, the fixation structure 300 includes adhesive and non-adhesive portions. For example, the interface-facing region of the body 302 can be non-adhesive and the interface-facing region of the separable extensions 332A, 332B can be adhesive, or vice-versa. This can aid in removing the fixation structure 300 from the tube, such as by tearing the fixation structure 300 along a row of perforations and separating the fixation structure 300 from the tube via the tear. It has been found that, in some implementations, when both the body 302 and the extensions 332A, 332B are adhesive, the fixation structure 300 can become overly fixed to itself. This can inhibit removing the fixation structure 300 from the tube, such as by interfering with the ability to tear along the perforations. However, in some implementations, when only one of the body 302 and the separable extensions 332A, 332B includes an adhesive portion, the adherence of the fixation structure 300 to itself does not overly inhibit removal of the fixation structure 300 from the tube.

As shown in FIG. 72B, on the sides of the separable extensions 332A, 332B corresponding to the patient-facing region of the body 302, the separable extensions 332A, 332B include fixation elements 336A, 336B. The fixation elements 336A, 336B each engage with one of the attachment structures 216A, 216B in the same or a similar way as the fixation elements 310 described elsewhere in this disclosure with reference to FIG. 3. In the illustrated configuration, the fixation elements 336A, 336B include 'hook' pads to couple with the attachment structures 216A, 216B for a 'hook-and-loop' style connection. In some embodiments, the fixation structure 300 can adhere to other surfaces, such as the patient's skin, the tube 400, etc. For example, the fixation structure 300 can include one or more adhesive portions and one or more non-adhesive portions. In certain embodiments, one or both of the separable extensions 332A, 332B include adhesive portions.

In some situations, a chinstrap may be used in conjunction with the two-part releasable attachment or connection arrangement. This chin strap may be a standard or conventional chinstrap that is used to keep the patient's mouth closed during CPAP therapy. The chinstrap helps ensure a sealed system (by helping to hold the patient's mouth closed or substantially closed for eliminated, or at least reduced, mouth leak) and thus more effective treatment.

Additionally, or alternatively, a chin strap may be part of the present invention and may be used without a two-part releasable attachment or connection arrangement to secure the device. In one example embodiment, the chinstrap comprises a material that is soft on the patient's face. Advantageously, the material may also be a stretchable fabric, such as a knit fabric, or a fabric comprising elastic material or elastic fibres. The chin strap may have one or more regions of hook or loop material/fasteners, and/or may be substantially made up of or covered by hook or loop material. In one preferred embodiment, this is loop material, which is soft on the patient's face. In another example preferred embodiment, this is hook material, so that any overlap of the second patch over the footprint of the strap does not cause any damage or scratching of the patient's face due to hooks on the interface patch. In a further preferred embodiment, the strap comprises at least one region of hook material, and at least one region of loop material. The chin strap may connect to a region of hook or loop fasteners on a connecting portion on the patient interface. This securement system secures the patient interface on the patient's face without having to apply any adhesive to the face.

In one example embodiment, the chinstrap is a continuous loop that extends around the back and/or top of the patient's head. In a further example embodiment, the chinstrap comprises a slit or bifurcation to allow it to conform to the patient's curved chin region.

Figure 23:
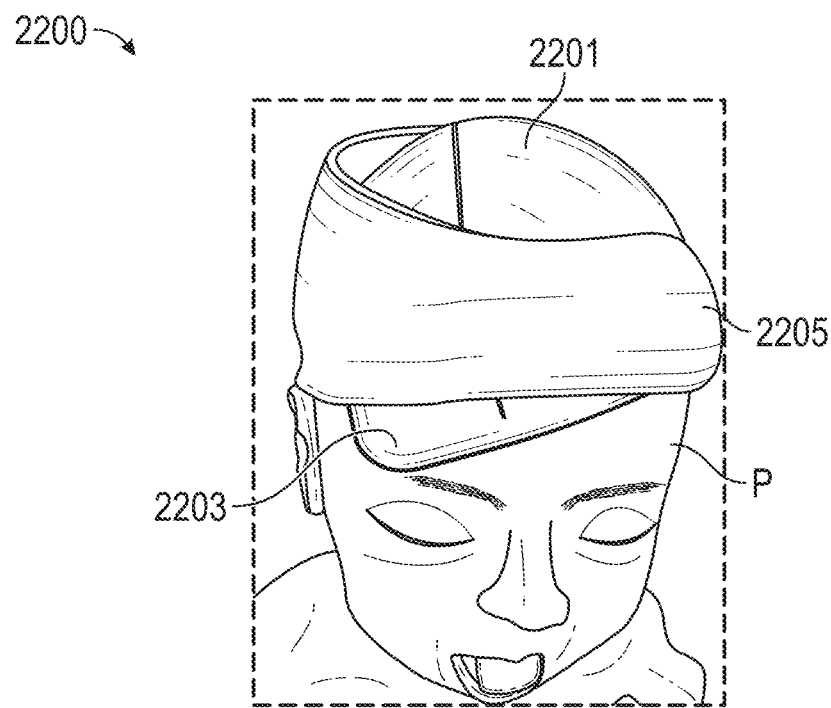
FIG. 23 shows the bonnet in place on a patient showing the adjustability on the front of the head.
Figure 24:
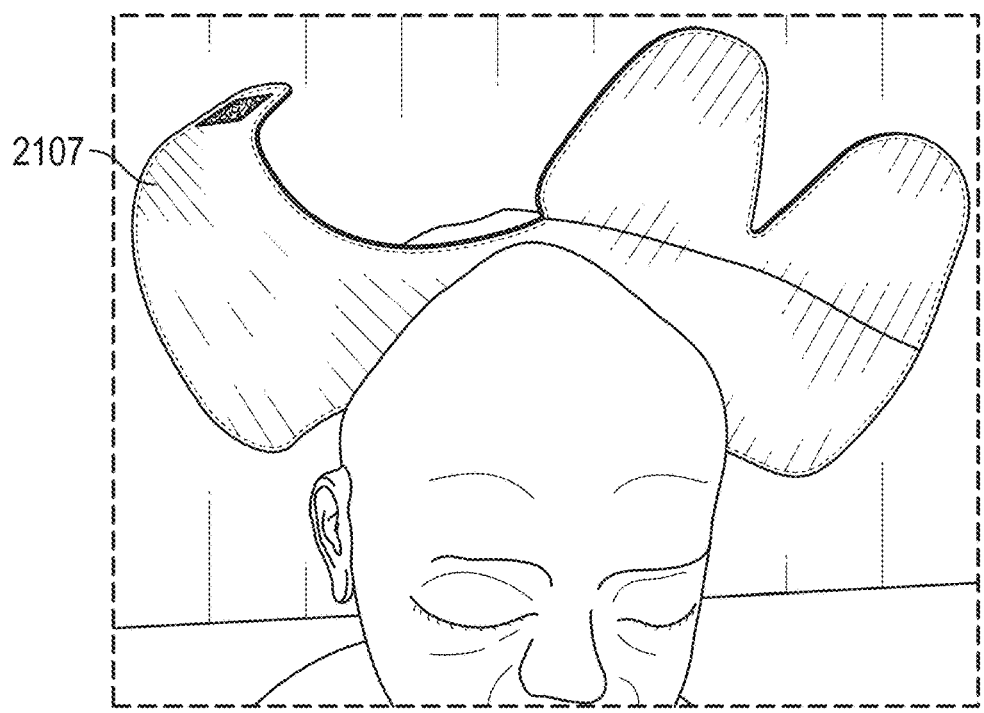
FIG. 24 shows the bonnet showing that it opens up at the front revealing the patient's head if any procedures/scans need to be performed.

The securement system may also include an adjustable bonnet 2201, as shown in FIGS. 22 to 24 and 31. The securement system may also include a pair of flaps 2203, 2205 that can be overlapped to secure the bonnet. The flaps 2203, 2205 provide adjustability of the size of the bonnet. This bonnet 2201 may comprise one or more sections of loop material. In the embodiment shown, the entire bonnet 2201 has a layer of loop material on at least it's outer surface. In another example embodiment, the bonnet includes loop material on both inner and outer sides such that it is reversible. This may help to eliminate error when putting in onto a patient. The bonnet 2201 may have multiple seams and may be adjustable, as shown in FIGS. 22-24, and 31. The bonnet 2201 is preferably adjustable at the front of a patient's head. The adjustability is provided via hook and loop fasteners as shown in FIG. 23, but may also be performed by any suitable structure, such as buttons, snaps, adhesive, magnets, ties, elastic, or other mechanical attachments. As shown at the front of the bonnet 2201 in FIGS. 23, the bonnet 2201 can be opened up, as seen in FIG. 24. This opening allows scans or other medical checks to be performed on the patient (for instance, the bonnet 2201 may allow access to the patient's anterior fontanelle, such as for ultrasounds). The capability to open and allow access to these areas means the bonnet 2201 does not need to be removed to do this scanning, which allows for uninterrupted therapy, decreases discomfort for the patient, and saves carer's time and effort in handling the patient to remove and then replace the bonnet and any associated interface or headgear components. The bonnet 2201 may be integral with the chinstrap. Alternatively, a region of the bonnet 2201 may be covered in a portion of hook or loop fasteners that can connect to a corresponding portion of hook or loop fasteners on a chinstrap or other straps (as in FIG. 22 embodiment).

Figure 25:
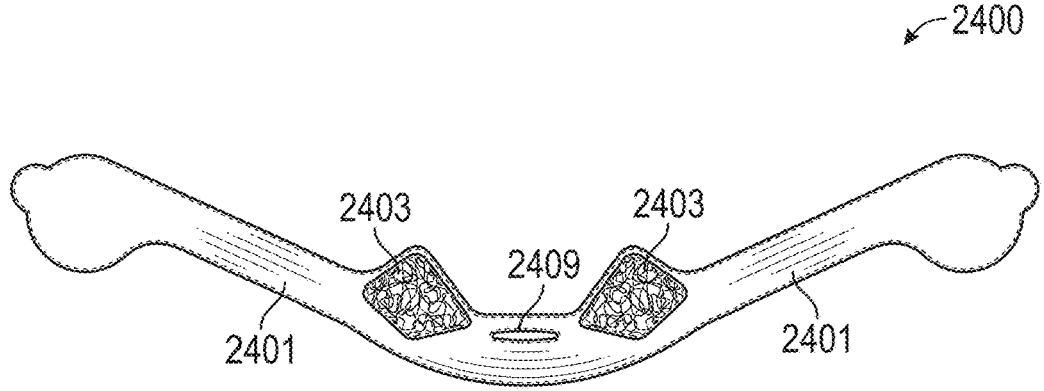
FIG. 25 is a front view of a chin strap.
Figure 26:
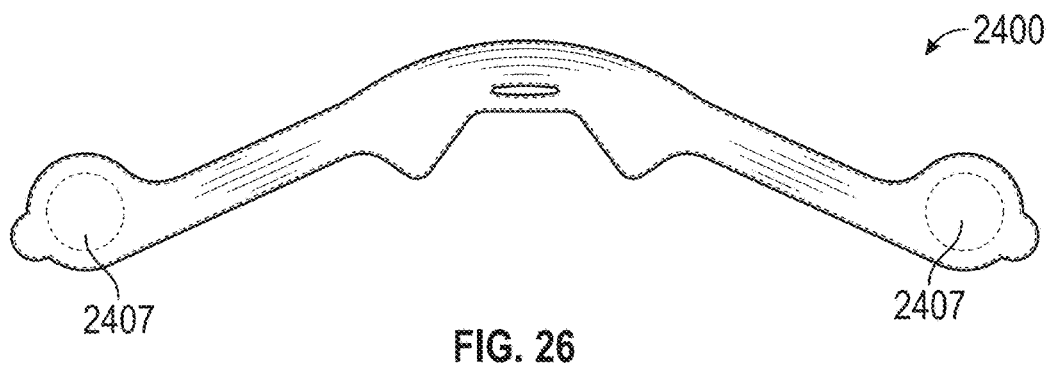
FIG. 26 is a back view of the chin strap.

An embodiment of a chinstrap 2400 that is attached to the bonnet 2201 via hook or loop fasteners is shown in FIGS. 25 and 26. The chinstrap 2400 is a generally V-shaped component, having a circular portion 2407 at each end. FIG. 25 shows two patches 2403 of hook material for attaching to the loop material on the patient interface. It should be appreciated that this may be loop material. Any such hook or loop material may be continuous on the strap, or may be provided in a region or regions as discussed above. FIG. 26 shows two circular regions of hook material 2407 on each circular portion 2407. It should be appreciated that any suitable shape and/or type of connection zone may be employed to mate with the bonnet. For instance, the attachment may be performed via buttons, snaps, hooks, magnets, adhesives, ties, flaps to surround the chin strap elements, or any other suitable mechanical or adhesive attaching mechanism. In the embodiment shown in FIGS. 25 and 26, the hook material 2407 attaches to the loop covered bonnet 2201 seen in FIG. 22. Alternatively, as discussed above, the chin strap may be continuous, and extend around the back and/or top of the patients head either underneath or over the top of the bonnet. In such an embodiment, it should be understood that hook/loop or other attachments to the bonnet may or may not be employed to impart additional stability. FIG. 25 shows the hook material on the front of the chinstrap 2400 on the cheek region near the chin. This attaches to corresponding loop material on the patient interface. This chin strap 2400 has a slit 2409 or bifurcation in the region of the patient's chin.

Figure 27:
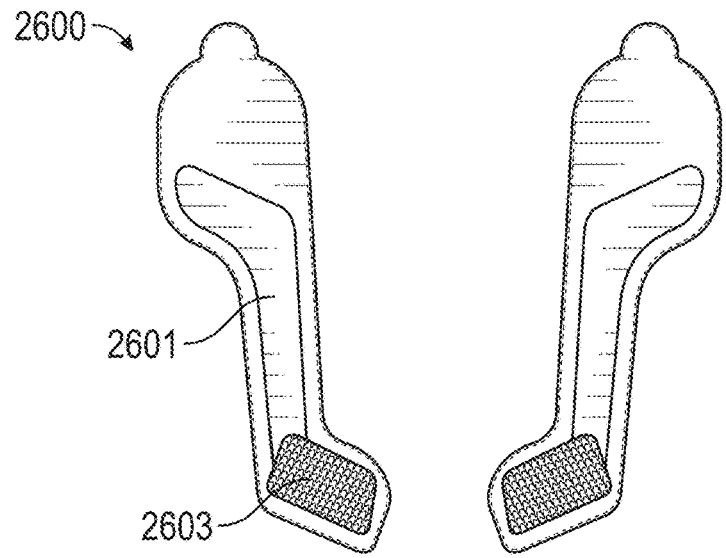
FIG. 27 is a front view of an embodiment of a side.
Figure 28:
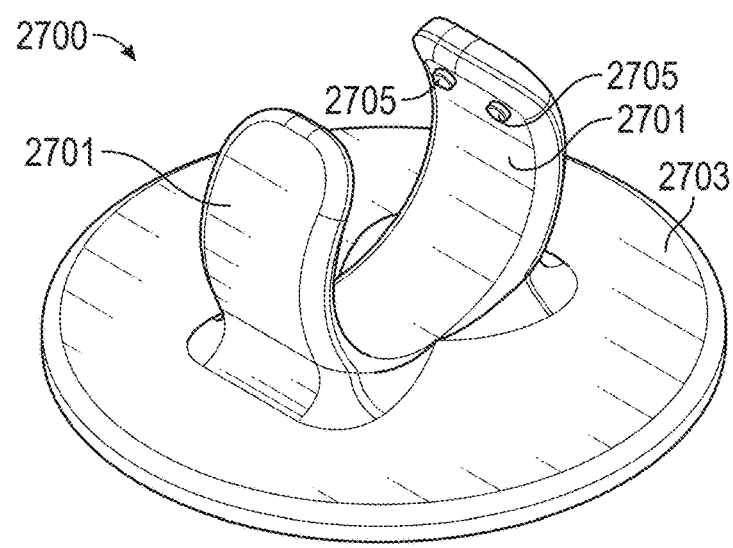
FIG. 28 is a perspective view of an embodiment of a tube clip showing bumps on the inner surface for holding the tube in place.
Figure 29:
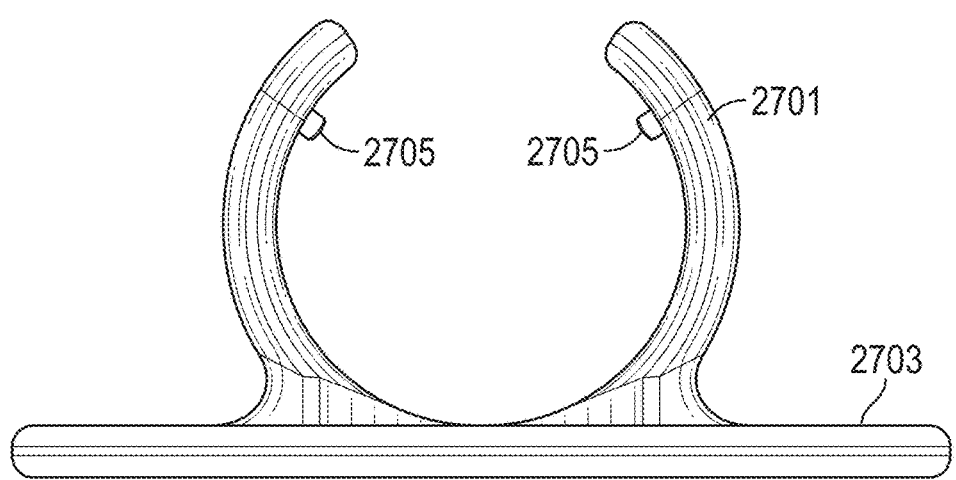
FIG. 29 is a side view of the clip of FIG. 28.

Furthermore, instead of extending over the chin, in one embodiment the at least one headgear strap may just extend down the side of the patient's cheek (like side burns). This 'side burn' strap may again comprise hook or loop material to attach to the patient interface and also to the bonnet 2201 (in an embodiment where the 'side burns' and bonnet 2201 are not integral). In one preferred embodiment, this is loop material to be soft on the patient's face. In another example preferred embodiment, this is hook material, so that any overlap of the second patch over the footprint of the strap does not cause any damage or scratching of the patient's face due to hooks on the interface patch. In a further preferred embodiment, the strap comprises at least one region of hook material, and at least one region of loop material. An embodiment of these 'side burns' 2600 that attach to the bonnet 2201 are shown in FIG. 27. The strap 2601 has a longitudinal body 2601 that extends down the side of the patient's cheek. The hook regions 2603 that are shown are for attachment to a patient interface. Alternatively, the whole side of the strap(s) may be formed of hook, loop, and/or hook and loop material.

The interface tubes that directly connect to the patient interface may have a side with a portion of hook or loop material and this may allow them to be fastened in position somewhere on the region of hook or loop fasteners on the chinstrap 2400, 'side burns' 2600 or bonnet 2201. For instance, the tubes may be provided with a circlet of hook or loop material or other type of mechanical or adhesive fastener (as described above with respect to the bonnet and chin strap embodiments). Additionally or alternatively, a fastener may be provided for one or more of the tubes. An example of a suitable fastener is a clip 2700 shown in FIGS. 28 and 29. It can be seen that these clips have a circular recess that the tube can fit in, surrounded by resilient arms 2701. Protrusions 2705 on the inside surface of the clips assist with securing the tube so it remains in place and does not move relative to the clips. Preferably, these clips hold the tube (by friction and/or interference fit) securely enough to absorb or attenuate forces applied to the distal end of the tube from affecting the interface or imparting a load on the interface, yet loosely enough that the tube may be easily removed from the clip and replaced into the clip in a different orientation (or slid transversely in the clip by use of force greater than common tube weight forces—i.e. an intentional sliding force, rather than an accidental tube movement force).

Figure 30:
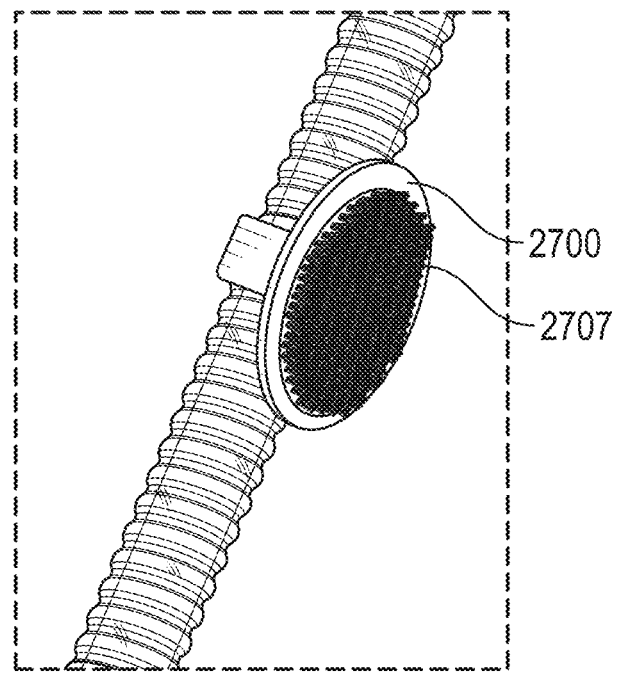
FIG. 30 is a detail view showing a tube clip that has been clipped on to an interface tube showing the region of hook material for selective attachment.

The tube clips may be part of the bonnet 2201 (permanently attached or integrally formed with) or preferably, may be separate from the bonnet 2201. In embodiments in which the clips are separate from the bonnet 2201, the clips may be attached to a portion of hook or loop fasteners 2707, which can attach to the corresponding fasteners on the bonnet 2201, chinstrap 2400 or 'side burns' 2600. An example of one of these clips attached to a tube is shown in FIG. 30.

With reference to FIGS. 46*a* to 71, a variety of different devices and components of tube management and retention systems will now be described. The devices and components described herein may be used individually or together, depending on requirements. The requirements include patient comfort, ease of use for a nurse or other medical professional, decoupling or reducing the load applied to the patient interface by the tube, ease of manufacturing, manufacturing costs, or location of attachment. The location of attachment may include any suitable component nearby to a patient, such as a bonnet, a chinstrap, the patient's skin or clothing, and/or other items such as bed sheet or blanket.

FIGS. 46*a* to 48 show schematics of another example fastener embodiment in the form of a sleeve 4600. The sleeve 4600 may be an alternative to the clip 2700 described above, or may be used together with the clip 2700. When not assembled with a tube 201, the sleeve 4600 is a substantially flat or planar component. Either side of the sleeve 4600 may be configured to attach to a headgear, bed sheet, blanket or other item of clothing and hold the tube in a desired position.

Figure 46A:
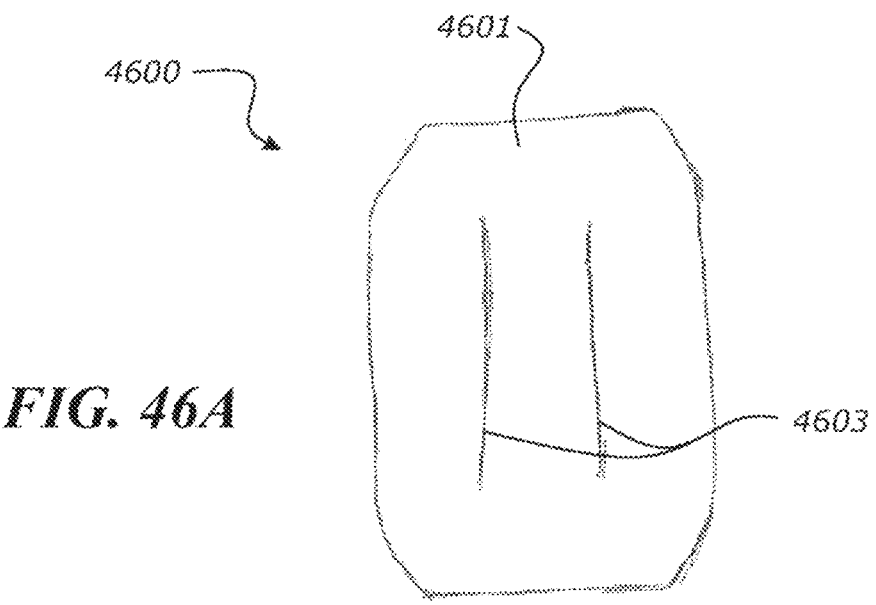
FIGS. 46A and 46B are schematics of a sleeve.

The sleeve 4600 is a short strip of material. FIG. 46*a* shows the sleeve in a 'resting', unused position. The material may include a portion of hook material, or a portion of loop material or portions of both hook material and loop material, and this may allow the sleeve 4600 to be fastened in position somewhere on the region of hook or loop fasteners on the chinstrap 2400, 'side burns' 2600 or bonnet 2201. In some embodiments, the sleeve 4600 comprises hook material on one side and loop material on the other side. This gives the sleeves the flexibility to be able to be attached to either a corresponding hook or loop surface depending on what the patient is wearing. In some embodiments, the sleeve 4600 comprises hook material on both sides. In some embodiments, the sleeve 4600 comprises loop material on both sides. In some embodiments, the sleeve 4600 has a base material upon which the hook and/or loop material is attached. This attachment may be accomplished by, for example, stitching, gluing, welding (ultrasonic or otherwise), and/or any other attaching means as is known in the art.

Figure 46B:
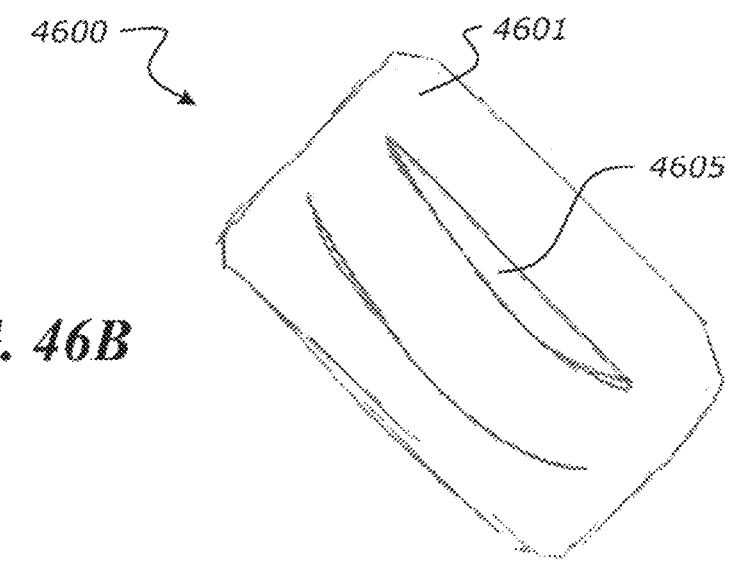
Figure 47:
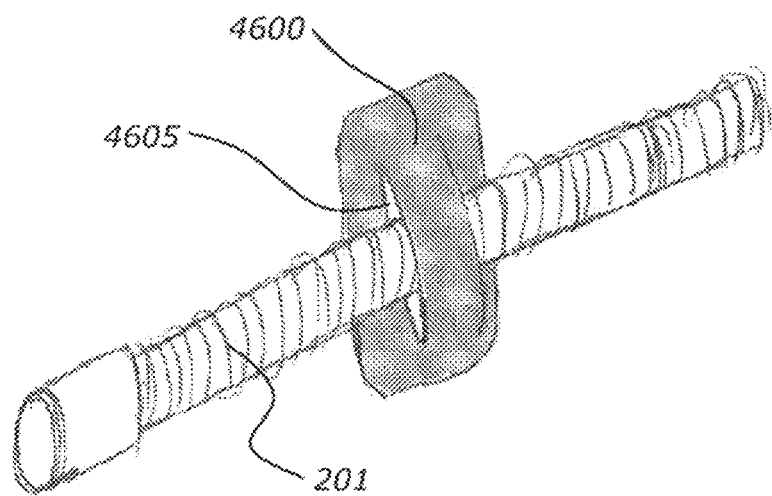
FIG. 47 is a perspective schematic of the sleeve of FIGS. 46A and 46B and a conduit.
Figure 48:
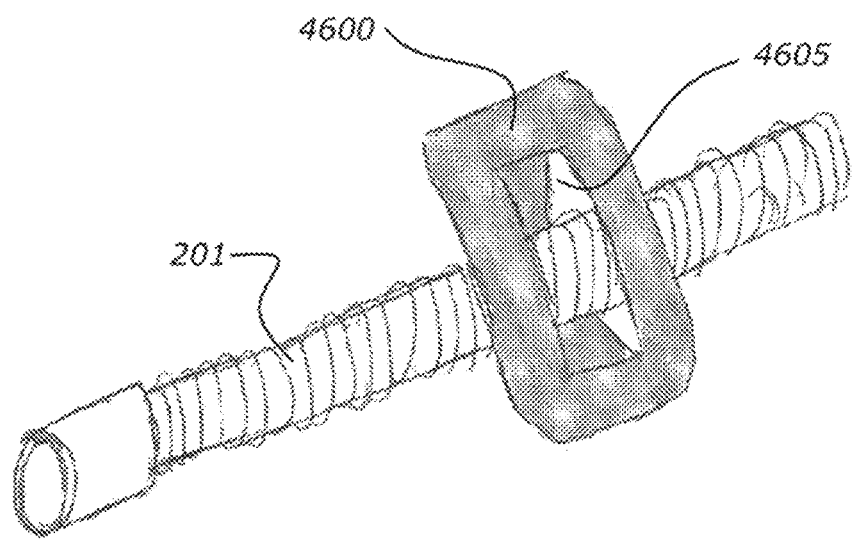
FIG. 48 is a perspective schematic of the sleeve and the conduit of FIG. 47 from the other side.

The sleeve 4600 is formed by at least one slit, slot, or cut 4603 in the material that provide a central portion. When assembled with the tube 201, a central section of the fastener 4605 is spaced away from the adjacent sections. FIG. 46B shows the sleeve 4600 with the centre part pushed out, able to receive a tube. FIGS. 47 and 48 shows two orientations of the sleeve 4600 over a tube 201.

The sleeves 4600 are formed such that they can be readily moved along the tube 201 to the desired location of securement. The sleeve 4600 can be readily moved along the tube 201 to a desired location by sliding relative to the tube 201. Preferably, the sleeve 4600 holds the tube 201 (by friction and/or interference fit) securely enough to absorb or attenuate forces applied to the distal end of the tube from affecting the interface or imparting a load on the interface, yet loosely enough that the tube may be easily slid through the fastener by use of force greater than common tube weight forces—i.e. an intentional sliding force, rather than an accidental tube movement force).

The sleeve 4600 improves patient comfort. The sleeve 4600 allows the tube 201 to be positioned such that when the patient is lying on their side they are not lying on a tube or fastener that may be uncomfortable and/or cause skin damage.

Figure 49A:
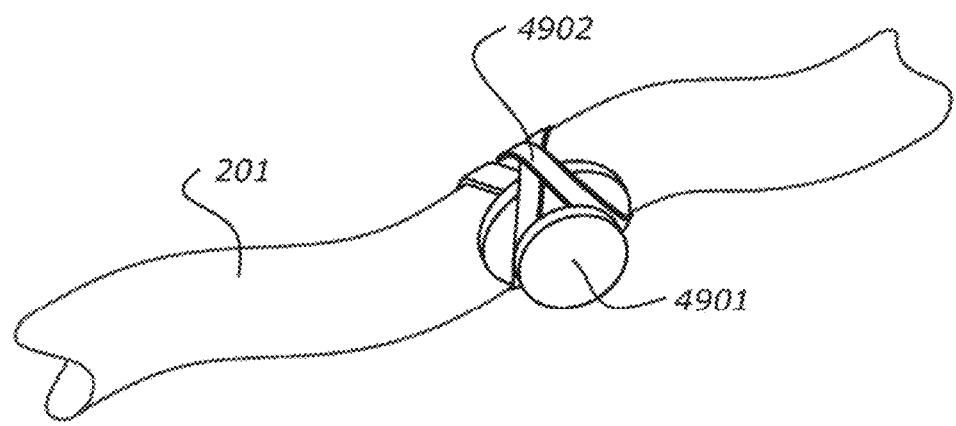
FIGS. 49A to 49C are a schematic of an alternative embodiment fastener.
Figure 49B:
Figure 49C:
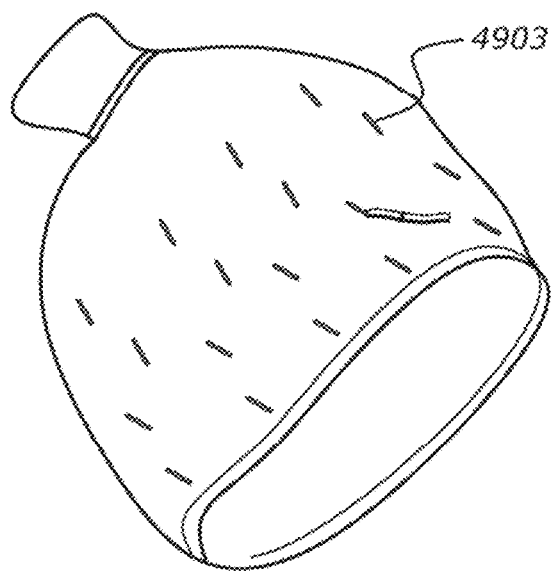

FIGS. 49A to 49C are a schematic of an alternative embodiment fastener.

In this embodiment, the fastener 4900 comprises a button 4901 attached to, or attachable to the tube 201. The button can be used to attach the tube to another item. There may also be a bonnet with a plurality of button holes or flaps 4903 for attaching the button to the bonnet.

FIGS. 50A to 50C are a schematic of an alternative embodiment fastener.

In this embodiment, the fastener 5000 comprises a tube clip 5001, similar to the previously described tube clip 2700. The tube clip 5001 is attached to a bonnet 5003, or other component, by a backing plate 5005 with small clips or other protrusions 5007 that extend through the material of the bonnet 5003 and attach to the body 5009 of the tube clip 5001.

Figure 51A:
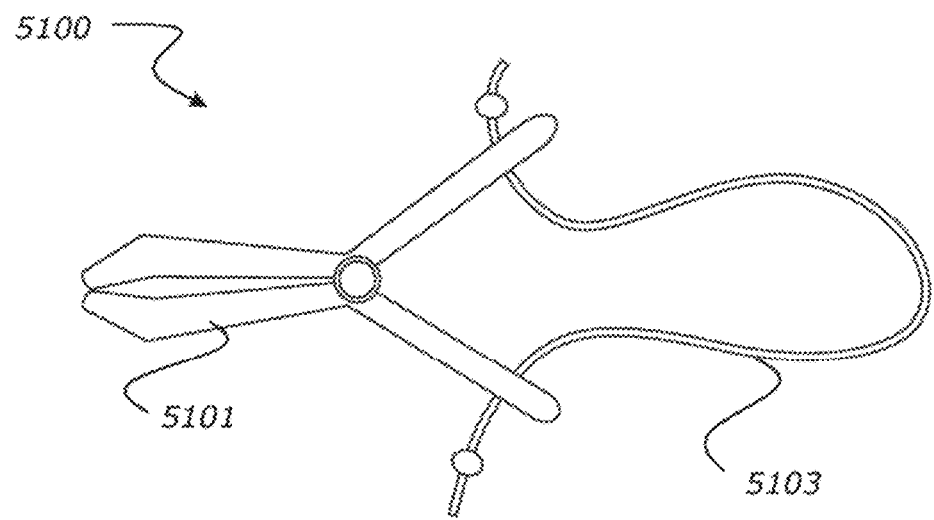
FIGS. 51A and 51B are a schematic of an alternative embodiment fastener.
Figure 51B:
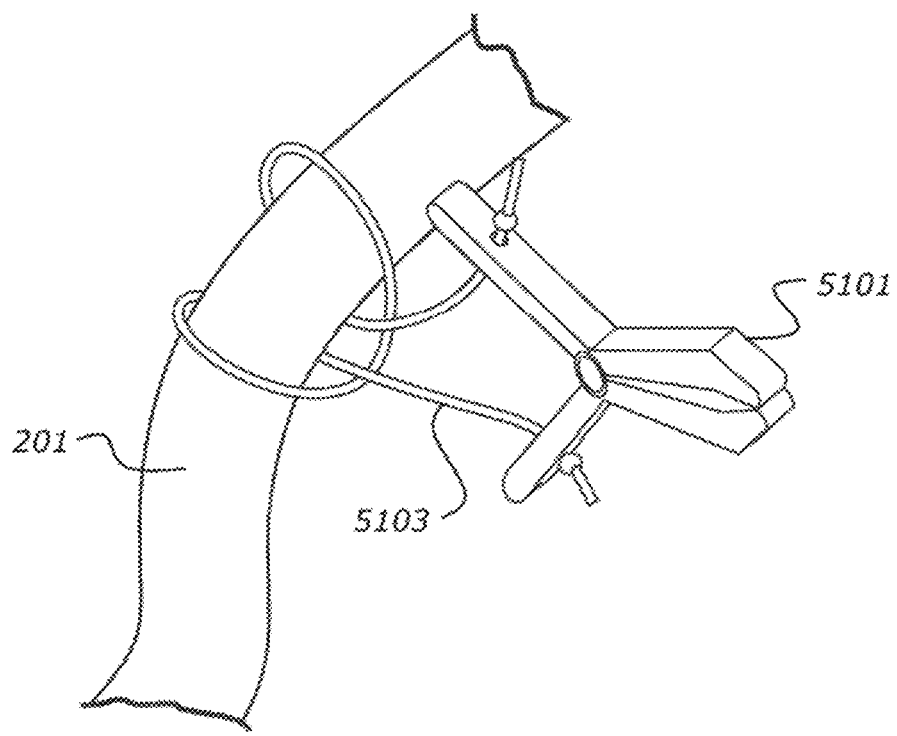
Figure 52A:
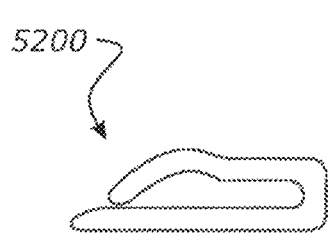
FIGS. 52A to 52D are a schematic of an alternative embodiment fastener.
Figure 52B:
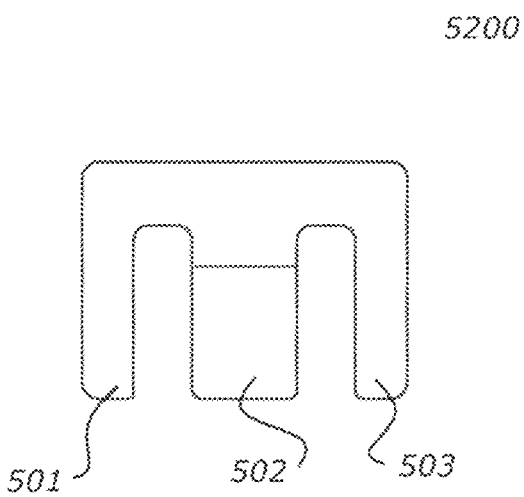
Figure 52C:
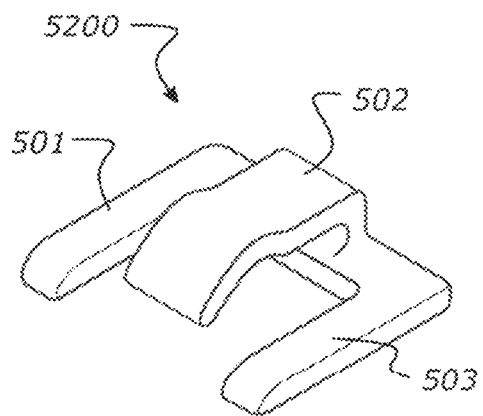
Figure 52D:
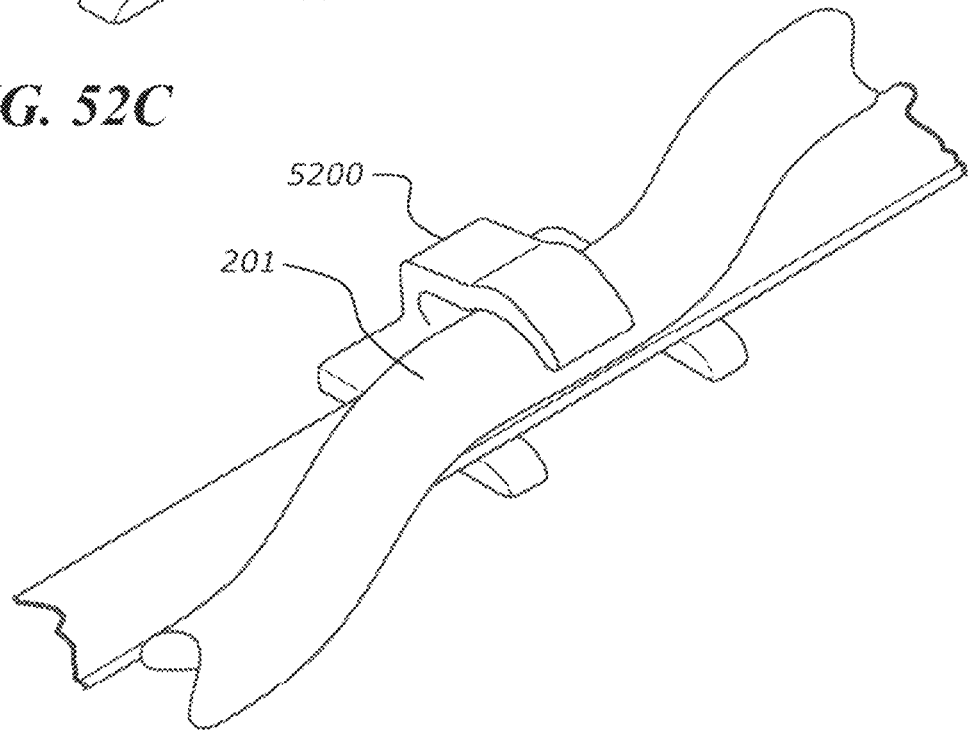

FIGS. 51A and 51B are a schematic of an alternative embodiment fastener. In this embodiment, the fastener 5100 comprises an arrangement of a clip 5101 and a cord 5103. The cord 5103 is configured to wrap around the tube 201. The clip 5101 is configured to engage the cord 5103 and another item, such as a bonnet, or bed sheet.

FIGS. 52A to 52D are a schematic of an alternative embodiment fastener.

In this embodiment, the fastener 5200 is a clip having three fingers 5201, 5202, 5203. In use, the two outer fingers 5201, 5203 extend over one side of the tube 201 and the inner finger 5202 extends over the other side of the tube 201. One, two, or all three fingers can attach to another item, such as a headgear strap, a chin strap, or a bonnet. For example, the inner finger 5202 can pass through the material of another item formed from knitted or woven fibres, such as a bonnet. This fastener 5200 is simple because there are no moving parts or complex materials required. This fastener has a low manufacturing cost. This fastener is versatile because it is easy to use and can be paired with a variety of different head gear.

FIGS. 53A to 53D are a schematic of an alternative embodiment fastener.

In this embodiment, the fastener 5300 comprises a slider—that is, the fastener 5300 can slide relative to the tube. The fastener 5300 has a body 5301 and sides 5303 with cut-outs 5305. The fastener may have one or more inwardly extending protrusions 5307 that engage with outer surface of the tube 201. The fastener has an attachment means 5309, such as adhesive, hook material, loop material, or hook and loop material for attaching to headgear, such as a chin strap.

Figure 54A:
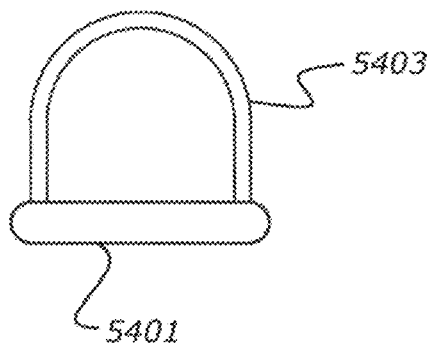
FIGS. 54A to 54C are a schematic of an alternative embodiment fastener.
Figure 54B:
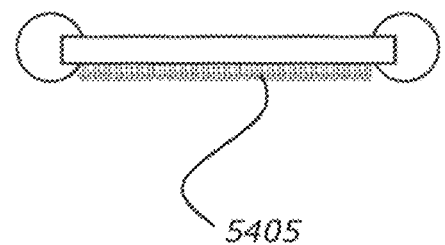
Figure 54C:
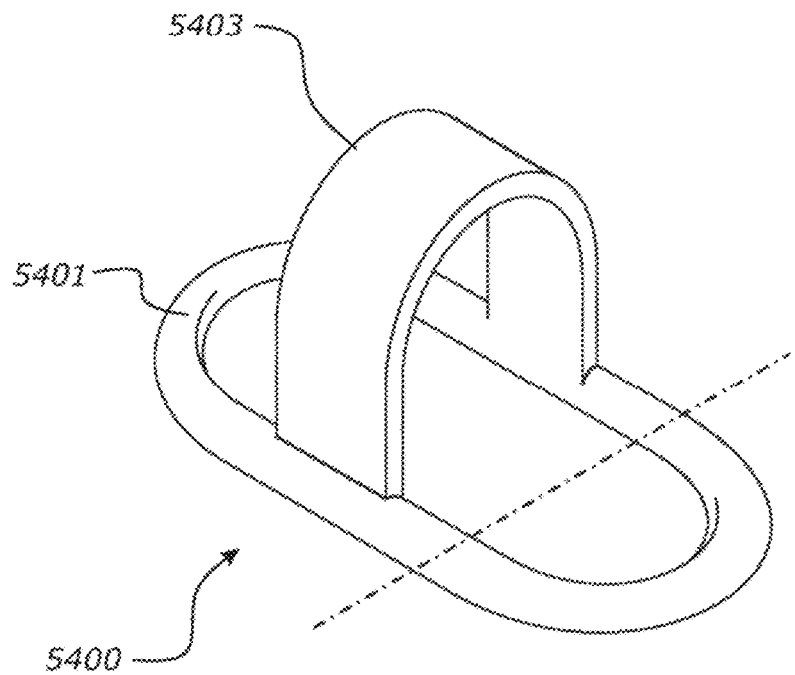

FIGS. 54A to 54C are a schematic of an alternative embodiment fastener. In this embodiment, the fastener 5400 comprises a slider. The fastener 5400 has a body 5401 and a loop 5403. The fastener has an adhesive 5405, such as hook material, loop material, or hook and loop material for attaching to headgear, such as a chin strap.

FIGS. 55A to 55C are a schematic of an alternative embodiment fastener. In this embodiment, the fastener 5500 comprises a slider. The fastener 5500 has opposing top and bottom members 5501 and opposing side members 5503. The opposing top and bottom members 5501 may have one or more sections of adhesive, hook material, loop material, or hook and loop material. The side members 5503 have inwardly extending protrusions 5505 that engage the outer surface of the tube 201. The side members are or comprise a resilient material such that the inwardly extending protrusions 5505 are urged towards the tube 201. A user can disengage the fastener 5500 from the tube 201 by pressing the opposing top and bottom members 5501 towards each other. Once in the desired location, the pressure can be released and the inwardly extending protrusions 5505 allowed to engage the conduit 201. This fastener 5500 has a distinction between a locked configuration in which the protrusions 5505 engage the tube 201 and a sliding configuration in which a nurse can slide the fastener over the tube 201 without catching the tube 201. This fastener 5500 has an intuitive movement for ease of use, and is easy for a nurse to adjust. This fastener 5500 has a low manufacturing cost.

Figure 56A:
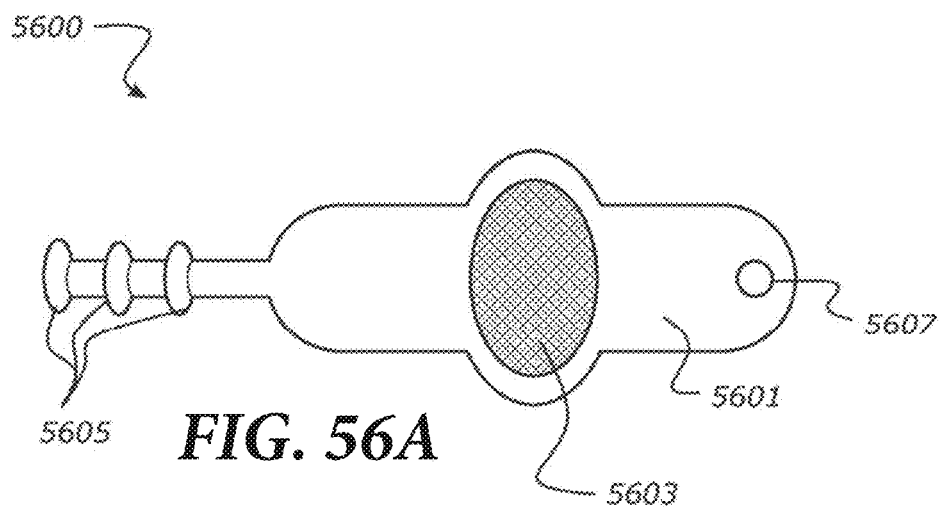
FIGS. 56A to 56C are a schematic of an alternative embodiment fastener.
Figure 56B:
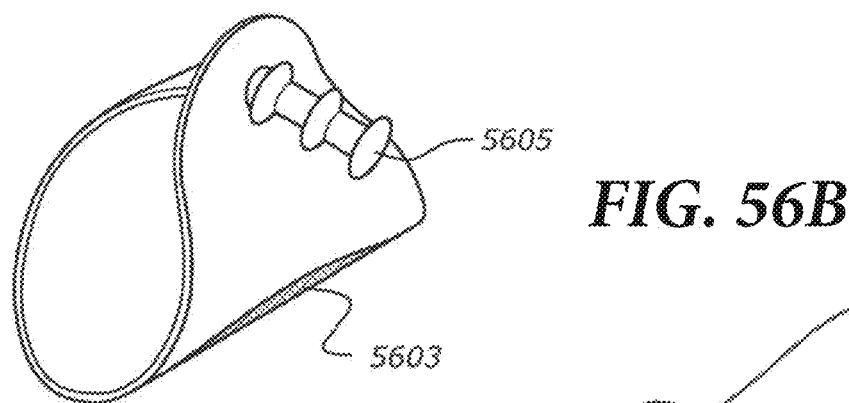
Figure 56C:
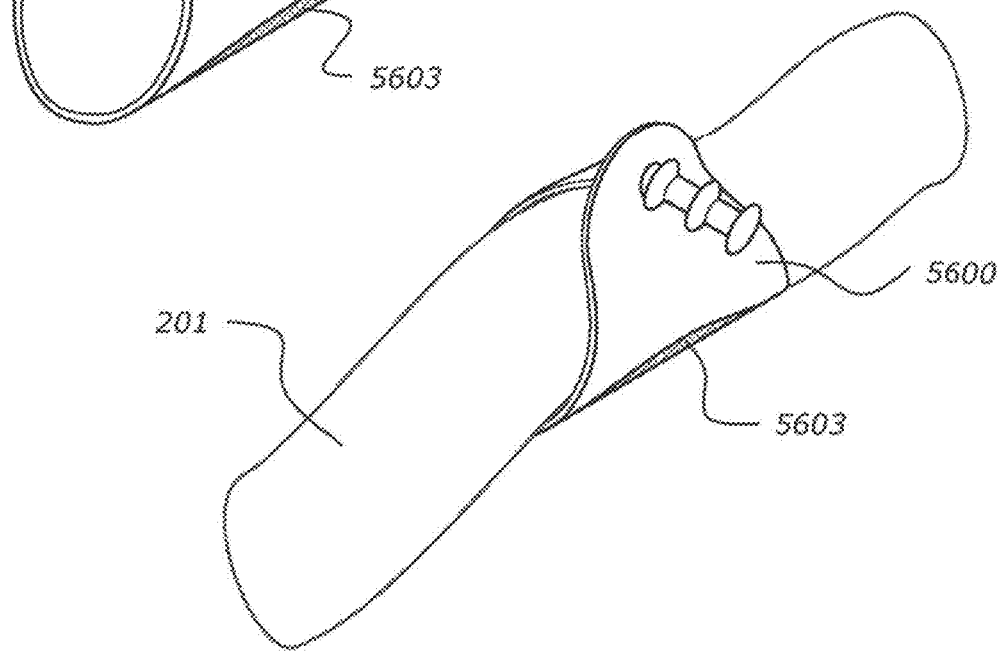

FIGS. 56A to 56C are a schematic of an alternative embodiment fastener. In this embodiment, the fastener 5600 comprises an elastomeric component. The fastener 5600 is, or comprises, an elastomeric material such as a thermoplastic elastomer. The fastener 5600 has a body 5601 with an adhesive patch 5603. The adhesive patch 5603 may be adhesive, hook material, loop material, or hook and loop material. The fastener has a tab with ribs 5605 that is receivable by an aperture 5607.

Figures 57A, 57B:
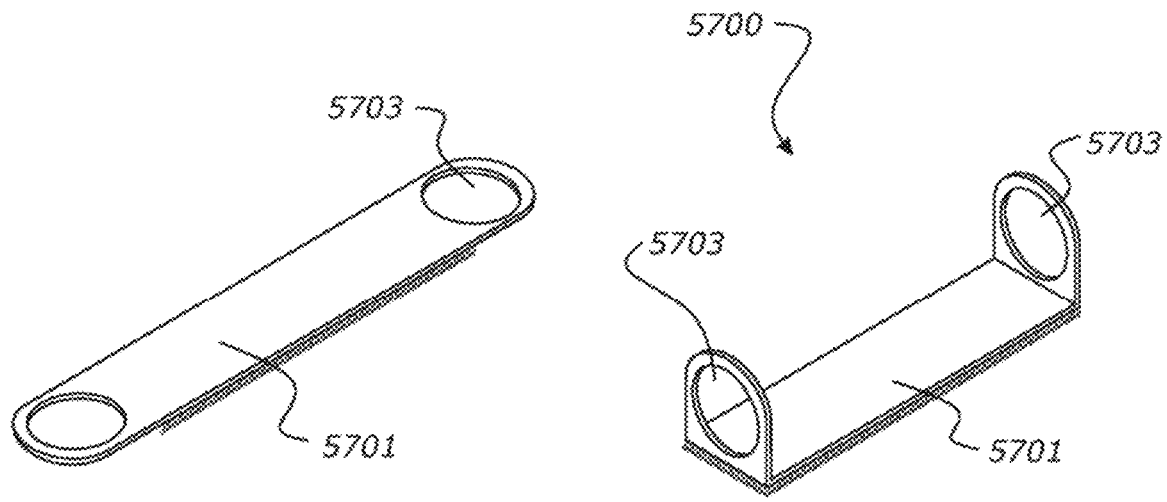
FIGS. 57A to 57C are a schematic of an alternative embodiment fastener.
Figure 57C:
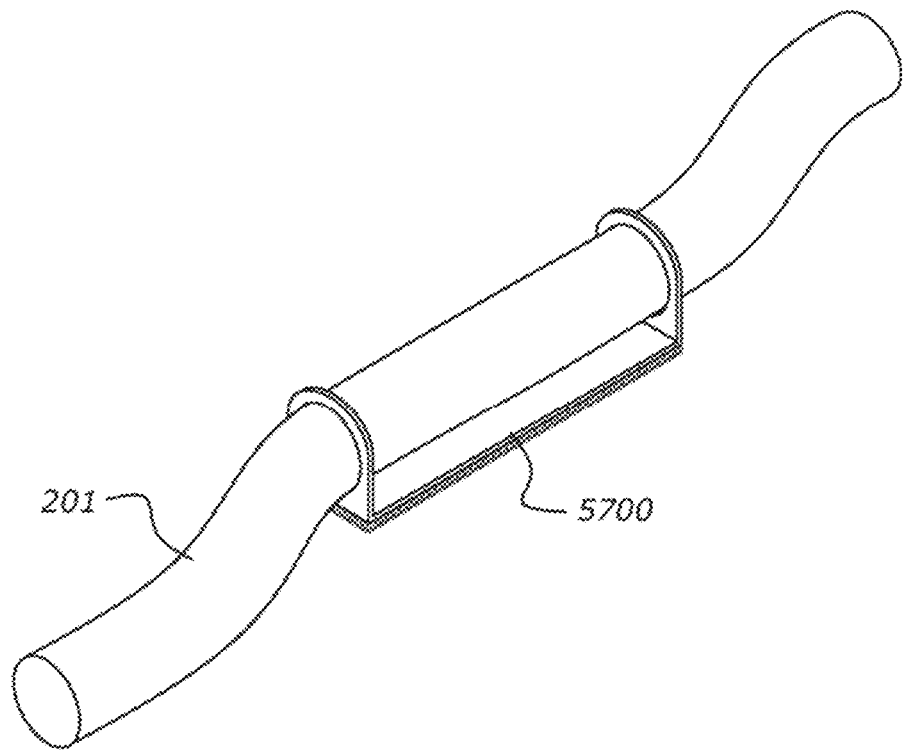

FIGS. 57A to 57C are a schematic of an alternative embodiment fastener. In this embodiment, the fastener 5700 comprises a strip of material formed to have a body 5701 with apertures 5703 configured to receive the tube 201. The fastener 5700 may comprise hook material, loop material, or hook material and loop material.

Figure 58:
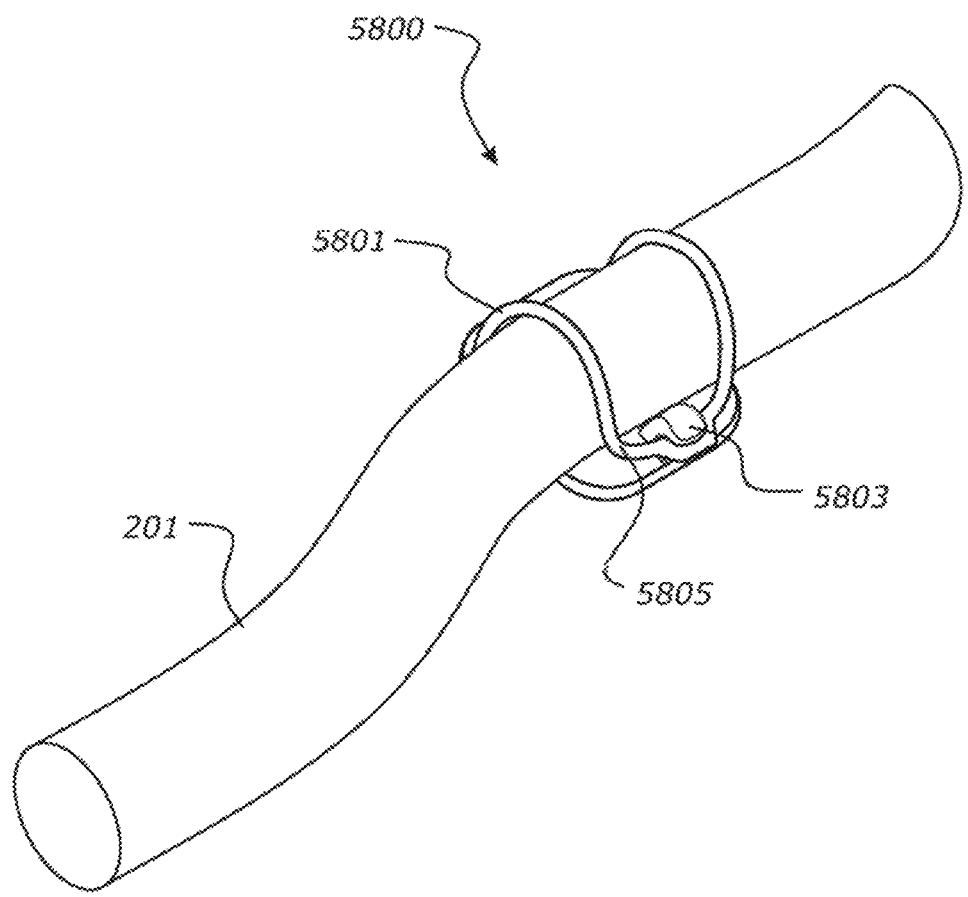
FIG. 58 is a schematic of an alternative embodiment fastener.

FIG. 58 is a schematic of an alternative embodiment fastener. In this embodiment, the fastener 5800 comprises a loop 5801 that is configured to engage a tab or button 5803. The loop is or comprises an elastomeric material such as a thermoplastic elastomer. The fastener 5800 also comprises a pad of hook material, loop material, or hook material and loop material.

The embodiments of FIGS. 49-58 demonstrate a patient interface assembly comprising: a tube management and retention system including a device configured to be removably attached to both the tube and any item in proximity to, or attached to, the patient.

As described above, the item may be headgear, chin strap, bonnet, clothing, or bedsheets. The headgear may comprise at least one headgear strap that extend down the side of the patient's cheek (like side burns). The chin strap may be attachable to a bonnet.

The chin strap may comprise hook and/or loop material. The hook and/or loop material may be in one or more regions. Alternatively, the hook and/or loop material may extend continuously on at least one side of the chin strap. The hook material may be in at least one region, and the loop material may be in at least another region.

The at least one headgear strap that extends down the side of the patient's cheek may be attachable to a bonnet. The at least one headgear strap that extends down the side of the patient's cheek comprises hook and/or loop material. The hook and/or loop material may be in one or more regions. Alternatively, the hook and/or loop material may extend continuously on at least one side of the at least one headgear strap. The hook material may be in at least one region, and the loop material may be in at least another region.

The benefits of such devices are that they are very configurable by the nurse or carer, as they may be attached at many different locations at the tube and at the associated headgear or chin strap or bonnet to clothing/bedsheets in proximity to the patient.

FIG. 59 is a schematic of an alternative embodiment tube management arrangement. In this embodiment, the tube management arrangement 5900 comprises a pillow configured to encircle a patient's face. The tube 201 is attached to, or attachable to the pillow 5900.

FIGS. 60A and 60B are a schematic of an alternative embodiment tube management arrangement. In this embodiment, the tube management arrangement 6000 comprises a foldable pillow configured to fold over a tube 201. This arrangement should be comfortable for a patient. Additionally, the pillow may provide in-tube condensate management.

FIGS. 59-60 demonstrate embodiments using one or more pillows. Such embodiments may be preferred as they are gentle on the patient's body and skin, provide support for the patient's head and/or neck, and can shield the patient from the pressure of laying on any rigid or semi-rigid components.

Figure 61:
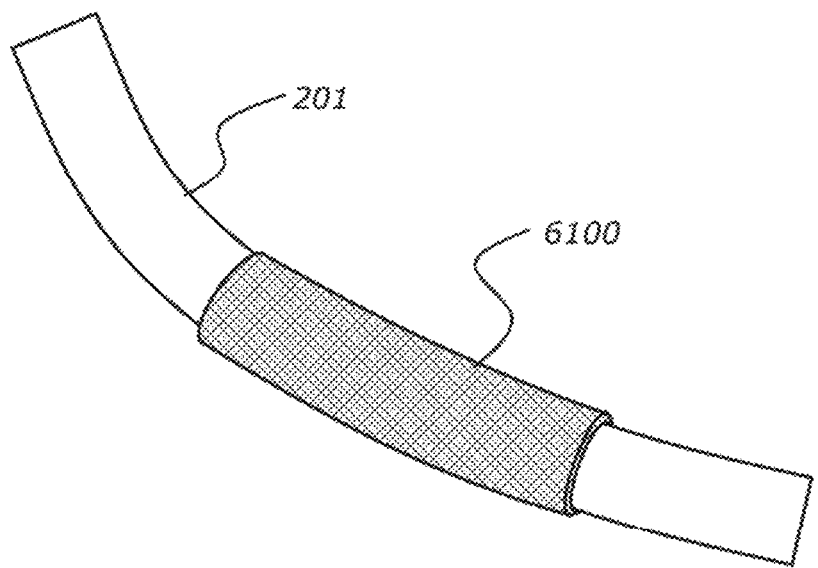
FIG. 61 is a schematic of an alternative embodiment fastener.

FIG. 61 is a schematic of an alternative embodiment fastener. In this embodiment, the fastener 6100 comprises a sleeve or tube of material. The sleeve 6100 may be or comprise hook material, loop material, or hook material and loop material. The sleeve 6100 may extend along the entire length of the tube 201, most of the length of the tube 201, or a small portion of the tube 201.

Figure 62:
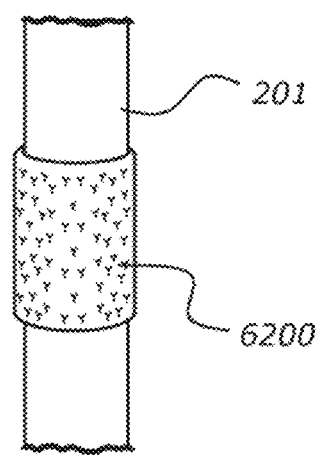
FIG. 62 is a schematic of an alternative embodiment fastener.

FIG. 62 is a schematic of an alternative embodiment fastener. In this embodiment, the fastener 6200 comprises a sleeve or tube of material. The sleeve 6200 may be or comprise a plurality of microscopic structures that form molecular-level bonds with a mating surface, also known as lizard feet or gecko feet material. This material reduces skin damage compared to other adhesive materials with larger structures.

The sleeve 6100 may extend along the entire length of the tube 201, most of the length of the tube 201, or a small portion of the tube 201.

The embodiments of FIGS. 61-62, and 63 demonstrate devices that are attached primarily to the tube itself, such as sleeves. Fasteners in the form of sleeves are versatile and easy to use. The sleeve may also be used to provide in-tube condensate management. When the tube is or comprises an adhesive (such as adhesive, hook, loop, and/or hook and loop) material, it can be adhered to other locations, allowing the tube to be attached to those other locations, for example during kangaroo care. Such devices are beneficial in that they may only require a nurse or carer to use one hand to place or remove them, and, to the extent they can slide along the tube, they allow the nurse or carer flexibility in choosing where to attach them to another component.

Figure 63A:
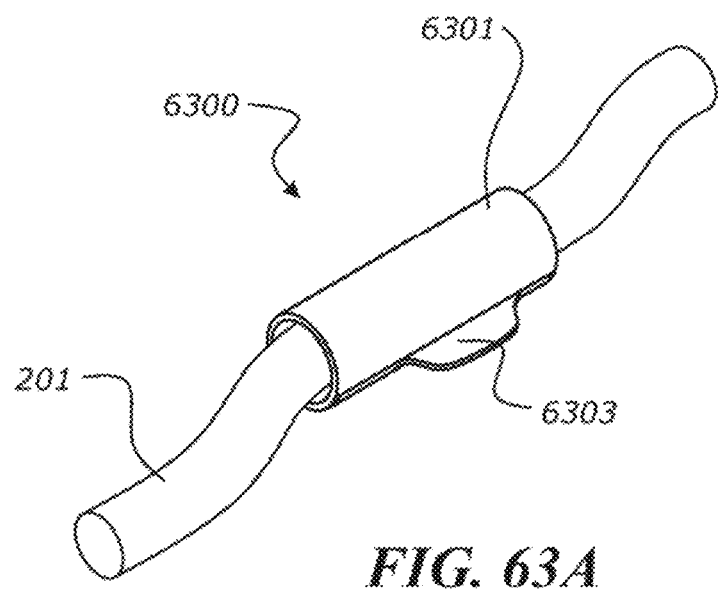
FIGS. 63A and 63B are a schematic of an alternative embodiment fastener.
Figure 63B:
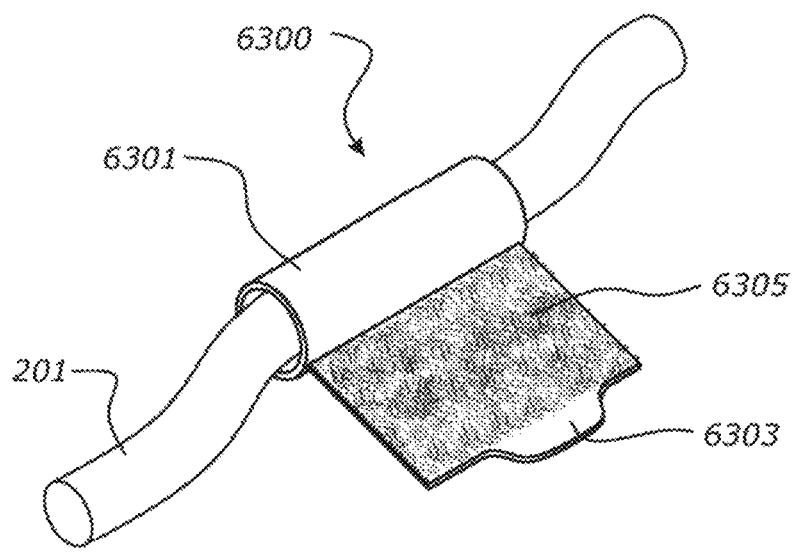

FIGS. 63A and 63B are a schematic of an alternative embodiment fastener. In this embodiment, the fastener 6300 comprises body 6301 housing a spring-loaded tab 6303 that at least partially coils around the tube 201. The tab 6303 comprises adhesive material 6305 such as adhesive, hook material, some loop material, or hook and loop material.

Figure 64A:
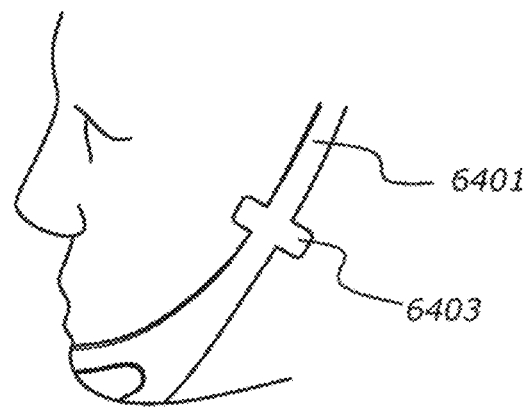
FIGS. 64A and 64B are a schematic of an alternative embodiment fastener.
Figure 64B:
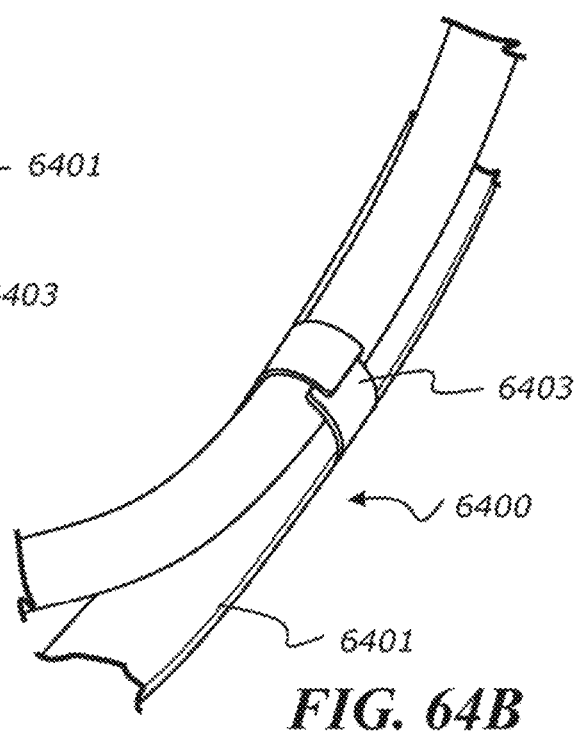

FIGS. 64A and 64B are a schematic of an alternative embodiment fastener. In this embodiment, the fastener 6400 comprises a chin strap 6401 with laterally extending tabs 6403. The tabs may be wrapped around the tube 201 to secure the tube 201.

Figure 65:
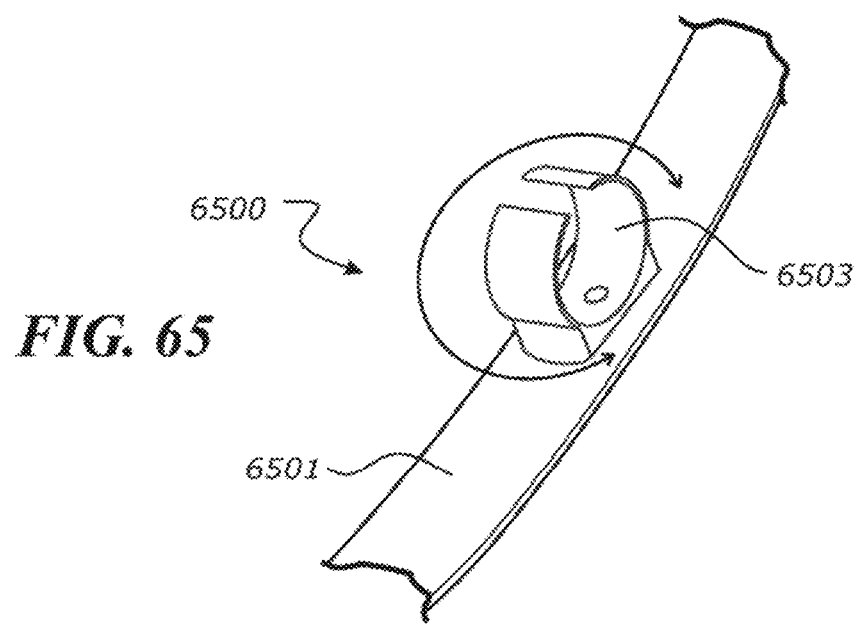
FIG. 65 is a schematic of an alternative embodiment fastener.

FIG. 65 is a schematic of an alternative embodiment fastener. In this embodiment, the fastener 6500 comprises a body 6501 with a rotatable tube clip 6503 that is rotatable relative to the body 6501. The body may be or comprise part of head gear, such as a chin strap.

Figure 66:
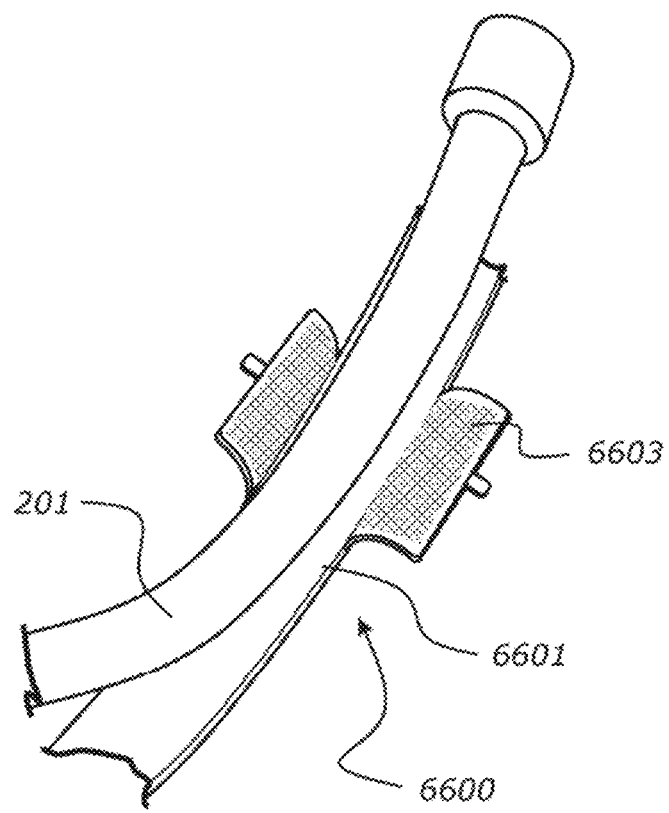
FIG. 66 is a schematic of an alternative embodiment fastener.

FIG. 66 is a schematic of an alternative embodiment fastener. In this embodiment, the fastener 6600 comprises a body 6601 laterally extending tabs 6603. One tab may be or comprise hook material and the other tab may be or comprise loop material. The tabs may be wrapped around the tube 201 to secure the tube 201. The body may be or comprise part of head gear, such as a chin strap.

The embodiments of FIGS. 64, 65, 66, 71 demonstrate examples of a patient interface assembly comprising a tube management system including a device configured to be removably attached to the tube and primarily and/or permanently attached to any item in proximity to, or attached to, the patient. Such devices are beneficial in that they are intuitive to use and may be easy to manufacture.

The item may be headgear, chin strap, bonnet, clothing, or bedsheets. The headgear may comprise at least one headgear strap that extend down the side of the patient's cheek (like side burns). The chin strap may be attachable to a bonnet.

The chin strap may comprise hook and/or loop material. The hook and/or loop material may be in one or more regions. Alternatively, the hook and/or loop material may extend continuously on at least one side of the chin strap. The hook material may be in at least one region, and the loop material may be in at least another region. The at least one headgear strap that extends down the side of the patient's cheek is attachable to a bonnet.

In one embodiment, the at least one headgear strap that extends down the side of the patient's cheek comprises hook and/or loop material. The hook and/or loop material may be in one or more regions. Alternatively, the hook and/or loop material may extend continuously on at least one side of the at least one headgear strap. The hook material may be in at least one region, and the loop material may be in at least another region.

The embodiments of FIGS. 67-70 are similar to those described above with respect to FIGS. 49-58, which demonstrate tube management and retention systems that involve a device configured to attach to (and be removed from) both the tube and any associated headgear or chin strap or bonnet to clothing/bedsheets in proximity to the patient.

Figure 67A:
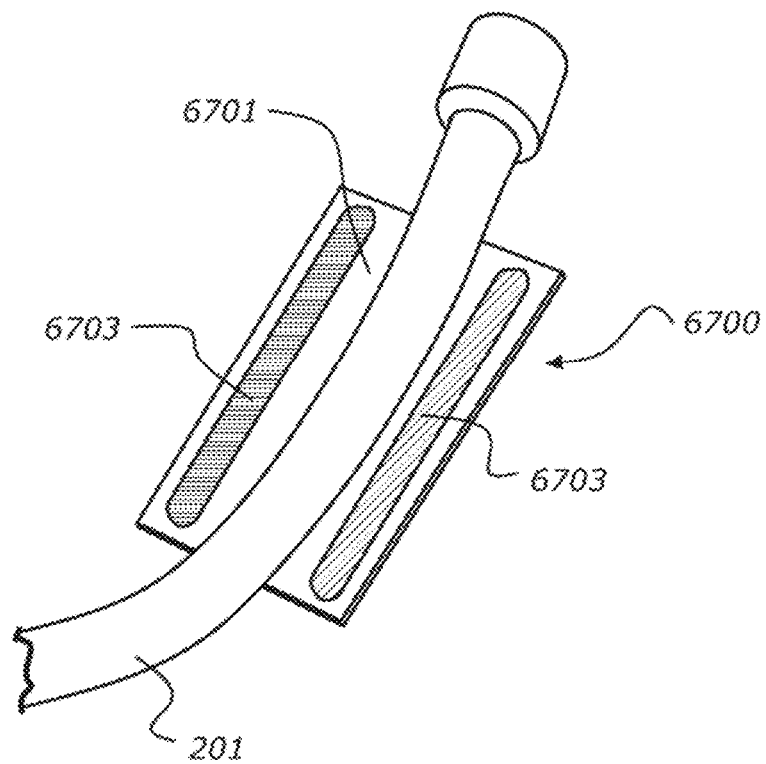
FIGS. 67A and 67B are a schematic of an alternative embodiment fastener.
Figure 67B:
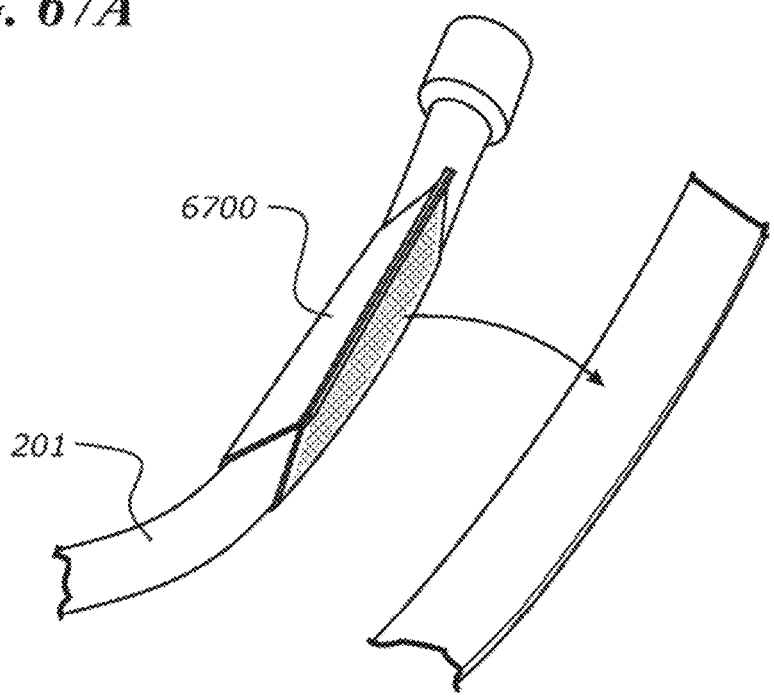

FIGS. 67A and 67B are a schematic of an alternative embodiment fastener. In this embodiment, the fastener 6700 comprises a body 6701 with laterally positioned tabs 6703. One tab may be or comprise hook material and the other tab may be or comprise loop material. The tabs may be brought together around the tube 201 to secure the tube 201. The body may be or comprise part of head gear, such as a chin strap.

Figure 68A:
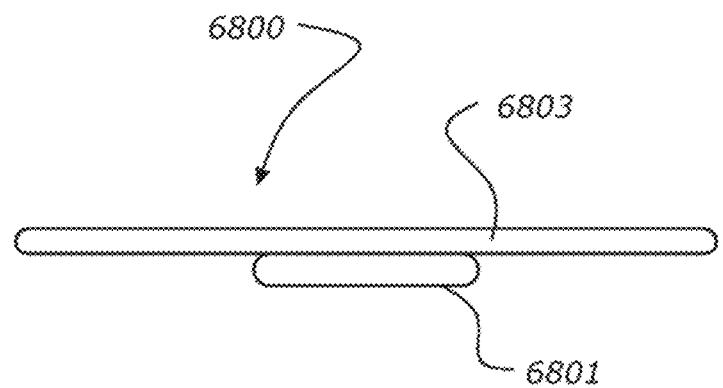
FIGS. 68A and 68B are a schematic of an alternative embodiment fastener.
Figure 68B:
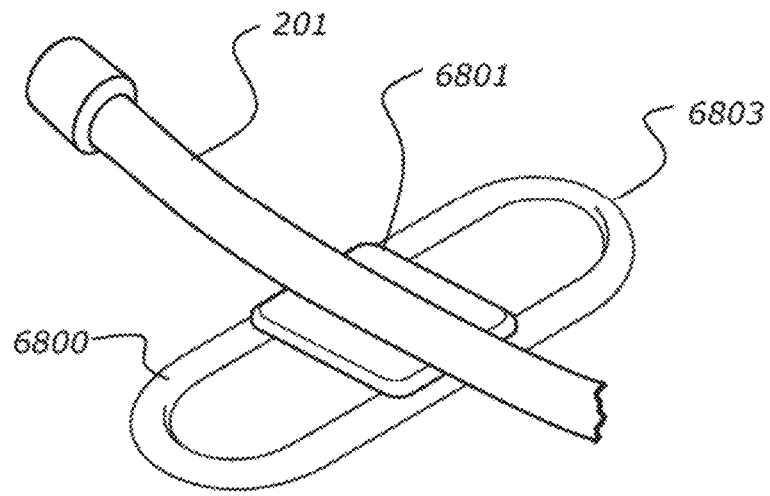

FIGS. 68A and 68B are a schematic of an alternative embodiment fastener. In this embodiment, the fastener 6800 comprises a body 6801. The body is formed from a gel material that can conform to the shape of the tube 201. The fastener may comprise an overmoulded edging 6803 that surrounds some adhesive material such as adhesive, some hook material, some loop material, or hook and loop material.

Figure 69A:
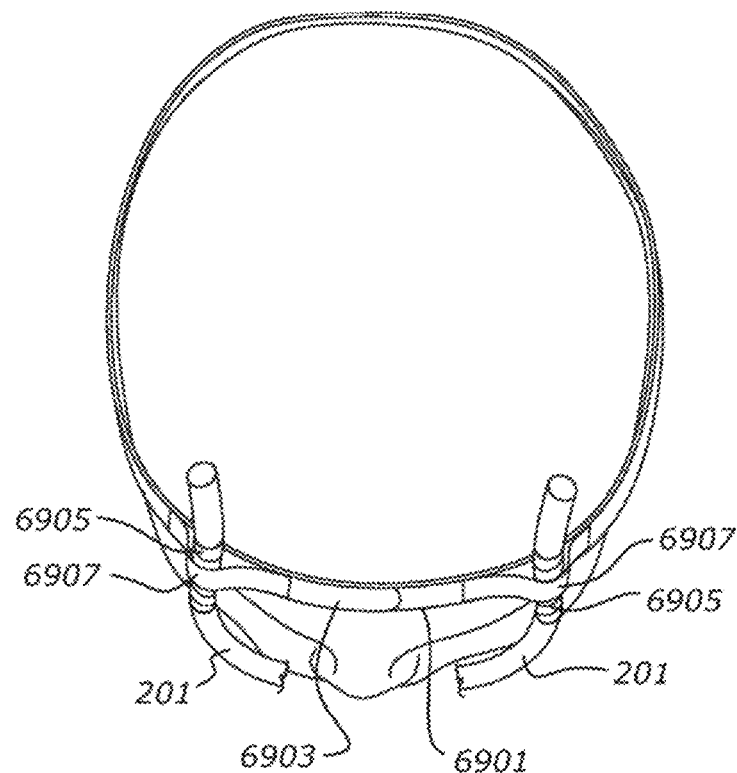
FIGS. 69A and 69B are a schematic of an alternative embodiment fastener.
Figure 69B:
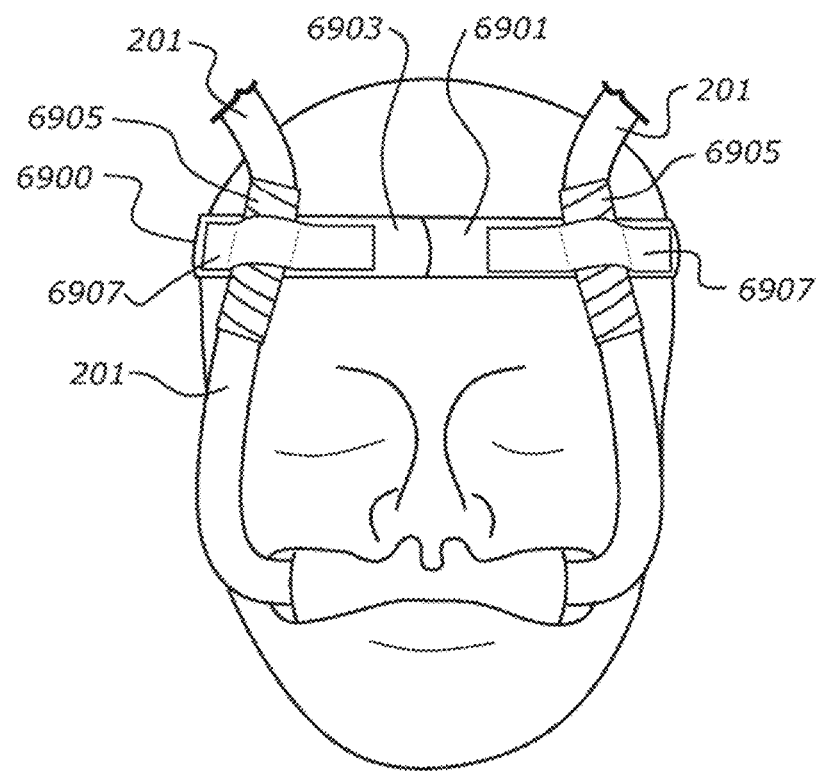

FIGS. 69A and 69B are a schematic of an alternative embodiment fastener. In this embodiment, the fastener 6900 comprises a self-adhering bandage or cohesive bandage. The bandage will adhere to itself, but does not adhere well to other surfaces. This fastener may be used to create a strap around any part of the patient's face. In use, a strap 6901 is wrapped around the patient's head with an overlapping portion 6903 that adheres to an underlying portion. A second strap 6905 is wrapped around at least a portion of the conduit 201. The wrapped portion of the conduit 201 is placed on the strap 6901 wrapped around the patient's head. As both straps comprise the self-adhering bandage or cohesive bandage, the straps will adhere to each other. which will secure the conduit 201 to the patient. A third strap 6907 of self-adhering bandage or cohesive bandage is then placed over the wrapped portion of the conduit 201. In some embodiments, there is no third strap 6907. A nurse can control how tight or loose the band is. This fastener does not need any other head gear, is easy to use, and has a low manufacturing cost, and is gentle on the patient's skin (as it only adheres to itself).

Figure 70:
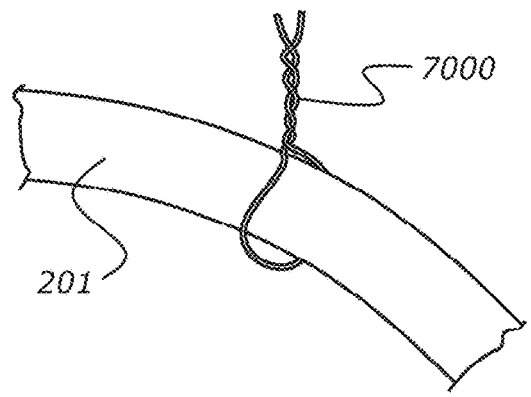
FIG. 70 is a schematic of an alternative embodiment fastener.

FIG. 70 is a schematic of an alternative embodiment fastener. In this embodiment, the fastener 7000 comprises a deformable member, such as a wire or component having an internal wire. The fastener 7000 can be attached to another component, such as headgear, a bonnet, or a bed sheet. In particular, an end of the fastener can pierce through the fibres of woven or knitted fabric, then the fastener tied or wrapped around the tube 201, securing the tube 201 to the fabric. This fastener 7000 can be used with current bonnets or beanies used for patients. This fastener 7000 is very easy to use and reposition. The construction of this fastener 7000 is simple. In use, the fastener 7000 is secure. The fastener 7000 may have a soft body with rigid/sharp ends to pierce through the fibres of woven or knitted fabric.

Figure 71A:
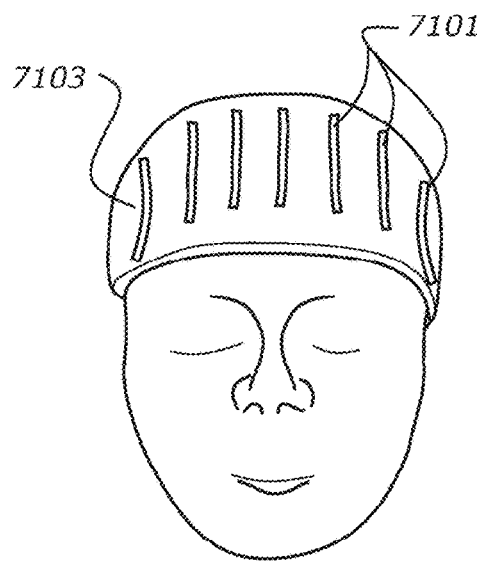
FIGS. 71A and 71B are schematics of an alternative embodiment fastener.
Figure 71B:
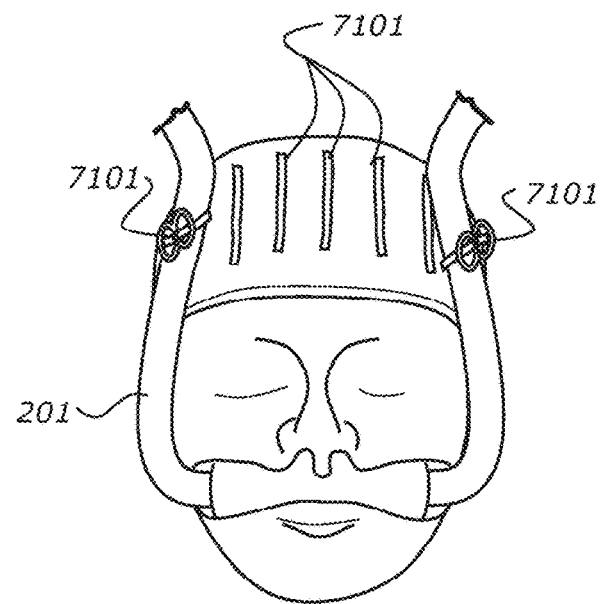

FIGS. 71A and 71B are a schematic of an alternative embodiment fastener. In this embodiment, the fastener 7100 comprises a plurality of elongate flexible components, in the form of ribbons 7101. The ribbons 7101 can be wrapped and secured around the tube 201. The ribbons may be attached to, or attachable to, a hat or bonnet 7103.

Figure 31:
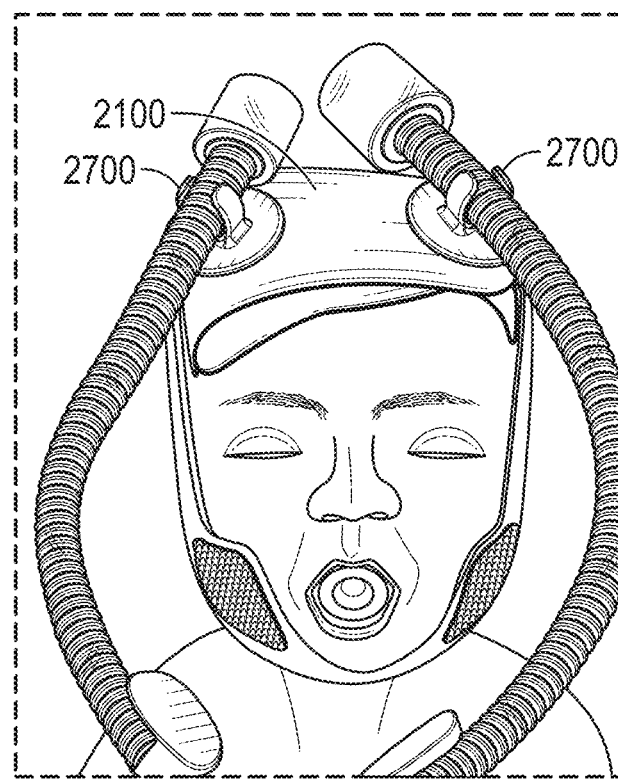
FIG. 31 is a perspective view of an example set up showing the bonnet, chinstrap, tube clips, interface tubes and nasal CPAP cannula, of the present disclosure.

FIG. 31 shows a possible setup without a two-part releasable attachment or connection arrangement. Here, the adjustable bonnet 2201 is used with a chinstrap 2400. The tubes are attached to the loop material of the bonnet 2201 via the tube clips 2700. The CPAP cannula in the bottom of the image is free to be positioned on the hook material on the chin strap.

In another example embodiment, an eye cover may be provided for use with at least one of the chin strap, side burns, and bonnet. This eye cover may be removably or repeatedly attached by the same methods described above with reference to these components, or any other suitable attachment method as known in the art. The eye cover would be useful to shield the eyes and/or eye region of patients undergoing phototherapy or other light-based therapies. It may also be useful to shield the eyes of resting and/or sleeping patients from room and/or equipment lighting in their bed space.

If the patient is not wearing a bonnet, the tube clips may be used by replacing hook material 2702 with an adhesive or with a clip that can clip on to bed sheets. All of this allows the clips to easily be positioned in the desired location. This ability for tubes to be held here or somewhere on the chinstrap 2400, 'side burns' 2600 or bonnet 2201 is advantageous over commonly used cannulas which are rigid with tubes that are difficult to reposition and thus make it difficult to place the patient on their side without disrupting therapy or being uncomfortable for the patient. For instance, the inspiratory and expiratory limbs to which the interface supply and expiratory tubes connect are often heavy and large. These clip or adhesive features assist in dissociating the force load from the existence and/or movement of the inspiratory/expiratory limbs from affecting the interface. This dissociation minimizes the risk of leaks or tissue damage.

Previously, adhesive medical tape has been used to retain the nasal interface in place. However, the fixation of the interface to the patient's face has been found to cause issues with the retention of the prongs 105 in the patient's nares, especially for infants and neonates. When the patient's face is squeezed from lying on the side, current nasal interfaces tend to bend at the bridge of the nasal interface in a direction away from the face. The bending of the interface causes the prongs 105 to displace out of the patient's nares, or become crushed against the sides of the patient's nose so as to cause at least a partial blockage of the gases being delivered to the patient.

Thus, in accordance with at least one of the embodiments disclosed herein, a nasal interface can be used that prevents or substantially reduces the likelihood of prongs displacing out of the patient's nares or irritating the nares as caused by facial movements or external forces.

A nasal interface can be configured to stabilize prongs on a patient's face when forces are exerted on the interface. The nasal interface can include an elongate body having an overall curvature that generally corresponds to a patient's facial profile, the body being configured to be coupled to a gases flow source and having at least one lumen extending at least partially through the body. The nasal interface can have prongs extending from the body and in fluid communication with the at least one lumen. The nasal interface can have one or more hinges.

Figure 32:
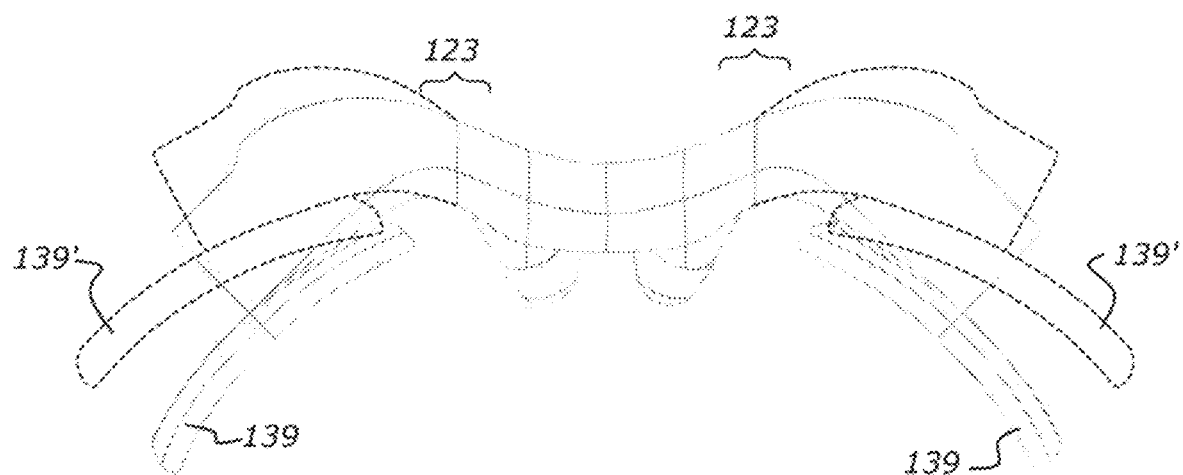
FIG. 32 shows the patient interface of FIG. 3 illustrating the hinging movement.

The nasal interface can have a generally gullwing shape. Except as described herein, the gullwing shape may have similar features and functions as the interface described in PCT application PCT/NZ2014/000217, published as WO2015/057083, the contents of which are incorporated herein by reference. In some embodiments, the nasal interface can have a wavy shape. In some embodiments, the nasal interface can have a curved space frame-like support structure. In the embodiment shown, movement of the wings will hinge about points to the lateral outsides of the prongs 105. FIG. 32 shows the patient interface illustrating the hinging movement. The broken lines illustrate positions in which the wings may hinge to.

A variety of hinge types can be used in the dynamic interfaces. The hinges can bend in a predictable, limited number of directions to define the mechanical behaviour of the dynamic interface. The following paragraphs describe a number of hinge types and how they can be implemented. The described hinges are not an exhaustive list of the hinge types that can be used and the scope of the present invention should not be limited by the particular embodiments described. The hinge types include, but are not limited to: notches, cross-sectional area, variable thickness, composite, elastic hinge, barrel & pin, and ball & socket.

In some configurations, the patient interface comprises one or more hinging regions 123, 1123 forming a bend in the body. Each of the one or more hinging regions 123, 1123 is configured to bend when a force is applied to the nasal interface. Each of the one or more hinging regions 123, 1123 is also configured to stabilize a position of the at least one nasal prong on a portion of the face of the patient in order to reduce the displacement distance of the at least one nasal prong out of a nare of the patient.

In some configurations, the one or more hinging regions 123, 1123 is located adjacent to the one or more prongs at a location that is spaced laterally and outwardly in relation to the one or more prongs.

For example, the one or more hinging regions 123, 1123 may comprise two hinging regions 123, 1123. When the patient interface comprises two prongs, a first hinging region 123, 1123 is located adjacent to a first prong at a location that is spaced laterally and outwardly in relation to a first prong and a second hinging region 123, 1123 is located adjacent to the second prong at a location that is spaced laterally and outwardly in relation to the second prong.

A hinge or hinging region 123, 1123 can be designed into the structure in any suitable manner. For example, a hinging region 123, 1123 may be created, in part, through variations in cross-sectional profile. Under an applied load a structure's cross-sectional area can predispose it to deflect in a certain direction. For example, the structure can be a portion of the body located adjacent or close to the prong the prongs of the nasal interface. The interface may have two or more hinges—that is, a hinge corresponding to each prong. A loading force F is assumed in the transverse direction as in FIG. 76C, simulating the exaggerated facial movements or external forces on the interface. The cross-section may be created by notches, cutouts, variable thickness wall sections (thinned and thick regions), use of materials with different properties, such as a rigid and flexible material overlaid together, or interface body geometry. Each of these designs achieve the desired purpose by bending in a desired direction (i.e. for a thinned wall section, the hinging region 123, 1123 is predisposed to bending in the direction of thinnest material). Alternatively the hinge may be a traditional mechanical hinge, such as using a pin and barrel or the like.

Figure 75A:
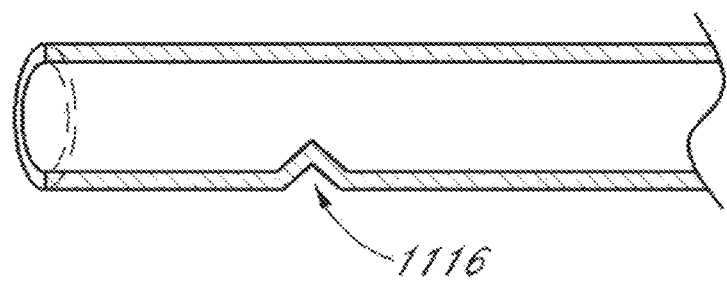
FIG. 75A to 75C illustrate other embodiments of hinging region in the form of a notch.
Figure 75B:
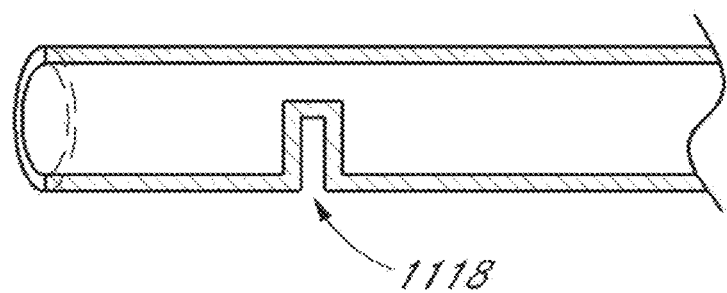
Figure 75C:
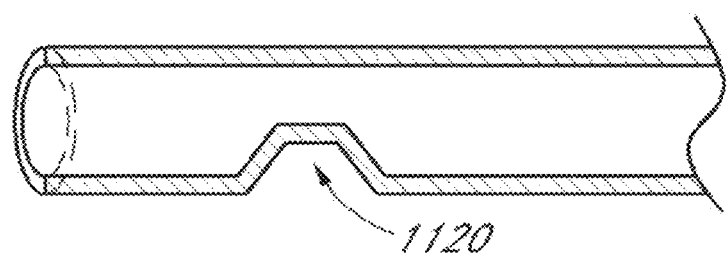

FIGS. 75A to 75C illustrate other embodiments of hinging region in the form of a notch that act as a hinge 1110. A number of non-limiting examples of notches are provided in FIGS. 75A to 75C. FIG. 75A illustrates a triangular notch 1116, FIG. 75B illustrates a channel notch 1118, and FIG. 75C illustrates a trapezoidal shaped notch 1120. The notch designs can be altered to permit different amounts of bending at the hinge and a designer can choose the proper type of notch design to achieve the desired amount of bending.

An elastic hinging region can be utilised to aid securement of an interface onto a patient's face. An elastic hinge can store elastic energy by pre-stressing the nasal interface before application to a patient. Once the nasal interface is on the patient, the stored elastic energy in the elastic hinges acts upon the patient's face to aid securement. An elastic hinge can have a relaxed state where substantially no elastic energy is stored in the hinge, and a pre-stressed state where some external forces have bent the hinge allowing it to store some elastic energy.

Figure 73:
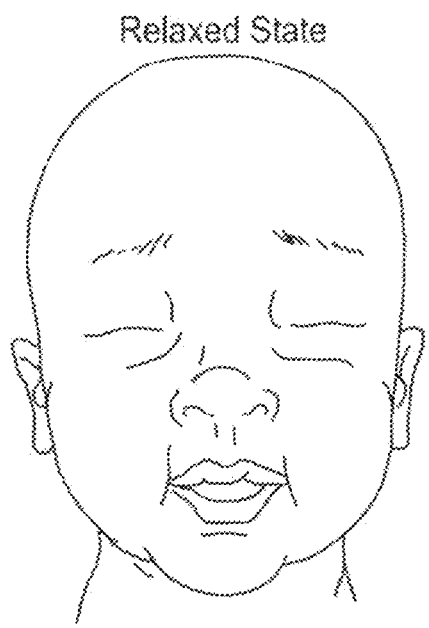
FIG. 73 shows a patient's face in a relaxed state.
Figure 74:
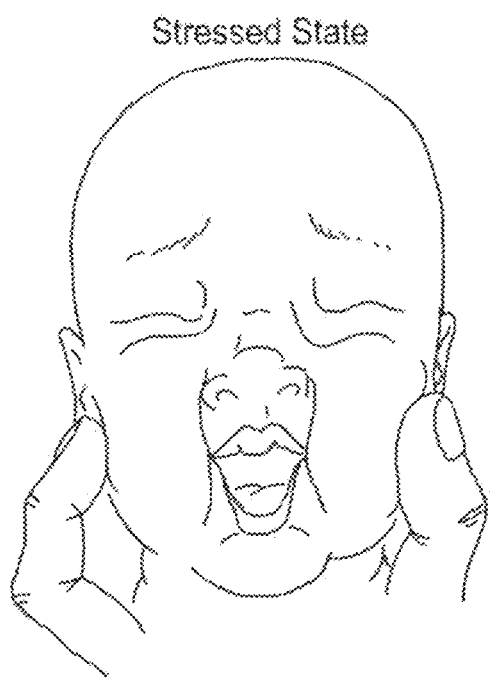
FIG. 74 shows a patient's face in a stressed state.
Figure 76A:
FIG. 76A to 76D are various views of an embodiment of an elastic hinge.
Figure 76B:
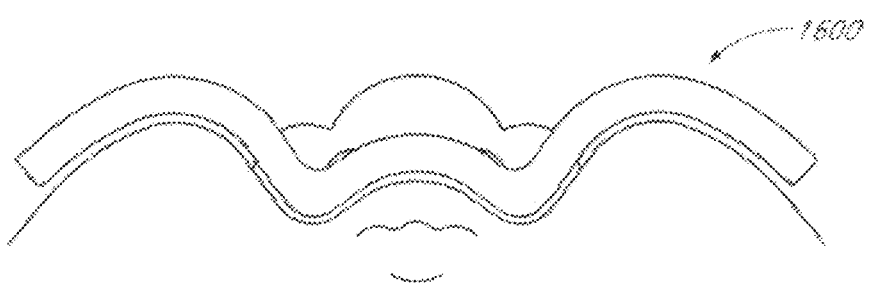

For example, a patient's face can be in a relaxed state, such as shown in FIG. 73, or in a stressed state, such as shown in FIG. 74. The nasal interface can be formed such that the relaxed state of the interface generally corresponds to the stressed profile of the patient's face. FIG. 76A illustrates an example of an elastic hinge nasal interface 1600 in a relaxed state. As illustrated in FIG. 76B, the nasal interface 1600 in a relaxed state can generally correspond to the stressed profile of a patient's face and in this configuration the nasal interface 1600 may exert no forces on the patient's stressed face.

Figure 76C:
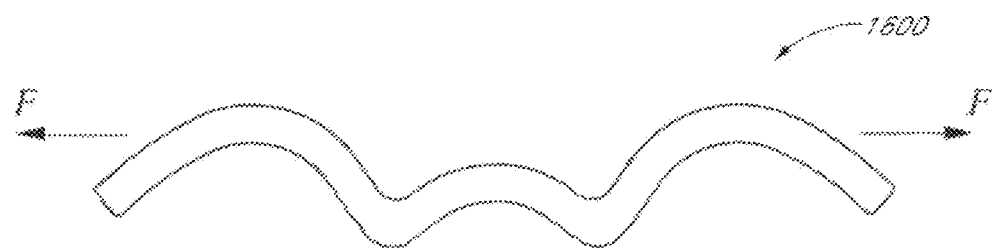
Figure 76D:
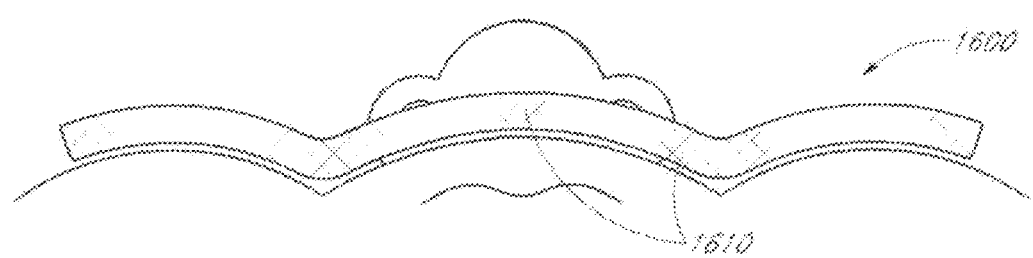

When fitting an elastic hinge nasal interface 1600 on a patient's face, a user can pre-stress the nasal interface by, for example, stretching the nasal interface as illustrated in FIG. 76C. When the pre-stressed nasal interface is placed on a patient's relaxed state face, the curves in the nasal interface serve as elastic hinges 1610, as shown by cross-hatching on FIG. 76D. When the patient's face is stressed, the elastic hinge nasal interface 1600 is predisposed to bend back to its relaxed state shown in FIG. 76B. The elastic hinge nasal interface 1600 can follow the patient's facial profile as the face goes from a relaxed profile to a stressed profile, which can stabilize the nasal prongs and help prevent the prongs from flicking out of the patient's nares or rubbing against the sides of the nares.

The nasal interface can be attached to the patient's face through a plurality of different types of retention methods, such as for example adhesives and straps as otherwise disclosed herein. Preferably, the retention method of the nasal interface on the patient's face has a strength that can at least withstand the pre-stress energy stored in the elastic hinges.

The elastic hinge nasal interface can be made of a resilient material that can store energy when stretched from its relaxed state. Some non-limiting examples of materials include rubber, plastics, composites and steel.

Preferred embodiments of the invention have been described by way of example only and modifications may be made thereto without departing from the scope of the invention.

The invention claimed is:

1. A patient interface assembly comprising:
    a patient interface comprising: a body and two nasal prongs extending from the body, each of the nasal prongs having a gas inlet for fluid communication with a supply of breathable gas, and a gas outlet configured to direct a flow of gas towards a nare of a user's nose, wherein each of the nasal prongs is in fluid communication with the other of the nasal prongs via a manifold, the manifold comprising an elongate body defining an interior space, wherein a wall of the elongate body defining the interior space is solid except for a first opening, a second opening and the gas inlet of each of the nasal prongs, wherein in a first configuration, the first opening is a gas inlet of the manifold and the second opening is a gas outlet of the manifold, and in a second configuration, the second opening is the gas inlet of the manifold, and the first opening is the gas outlet of the manifold;
    each of the nasal prongs further including an exterior surface, at least a portion of the exterior surface being a sealing surface configured to seal the nare of the user's nose; and
    a securement system for the patient interface, the securement system comprising a bonnet, and a two-part releasable attachment arrangement, the two-part releasable attachment arrangement comprising a first patch and a second patch,
    the first patch having a patient side and an interface side, the patient side of the first patch being attachable to the bonnet, the interface side of the first patch being provided with a first part of the two-part releasable attachment arrangement,
    the second patch having an interface side and a patient side, the patient side of the second patch being provided with a complimentary second part of the two-part releasable attachment arrangement, and
    the interface side of the second patch being attachable to or formed as part of the patient interface.

2. The patient interface assembly of claim 1, wherein each of the nasal prongs is an inspiratory and an expiratory prong.

3. The patient interface assembly of claim 1, wherein the manifold is fully and always open between the nasal prongs.

4. The patient interface assembly of claim 1, wherein the interface side of the first patch has one of a hook or a loop, and the second part of the second patch has the other of the hook or the loop, such that the first patch and the second patch are releasably attachable or connectable to each other.

5. The patient interface assembly of claim 1, wherein the first patch is locatable and/or attachable to skin on the user's face.

6. The patient interface assembly of claim 1, wherein the second patch is locatable, attached or attachable, or is connected to, or with, the patient interface.

7. The patient interface assembly of claim 1, wherein the first part of the two-part releasable attachment arrangement on the first patch occupies less than about 90%, or about 85%, or about 75%, or about 60%, or about 50%, or about 40%, or about 30%, or about 20%, or about 10% of the interface side of the first patch.

8. The patient interface assembly of claim 1, wherein the patient side of the first patch has a dermatologically sensitive adhesive configured to attach or adhere the first patch to skin of the user.

9. The patient interface assembly of claim 1, wherein the first patch has a surface of sufficient area such that, the surface is configured to distribute pressure or adhering forces across skin on the user's face.

10. The patient interface assembly of claim 1, wherein the first patch is configured to attach or adhere to the user's face adjacent the user's upper lip and/or cheek.

11. The patient interface assembly of claim 1, wherein the securement system is configured to receive and/or secure the patient interface and patient interface tubing, the patient interface tubing extending from one or both sides of the user's face.

12. The patient interface assembly of claim 1, wherein the patient interface comprises one or more hinges that are predisposed to bend in predefined directions, wherein the one or more hinges are configured to stabilize a position of each of the nasal prongs on the user's face when forces are exerted on the patient interface.

13. The patient interface assembly of claim 1, wherein the patient interface comprises one or more hinges located adjacent to each of the nasal prongs at a location that is spaced laterally and outwardly in relation to each of the nasal prongs, wherein the one or more hinges are predisposed to bend in a pre-defined direction.

14. The patient interface assembly of claim 12, wherein at least one of the one or more hinges is configured to bend inward towards the user's face and/or downwards from the user's nose.

15. The patient interface assembly of claim 12, wherein the one or more hinges comprise a variable cross-sectional area or a variable thickness.

16. The patient interface assembly of claim 12, wherein the one or more hinges comprise an elastic hinge that is configured to be pre-stressed before application to the user.

17. The patient interface assembly of claim 1, further comprising one or more hinging regions forming a bend in the body, wherein each of the one or more hinging regions is configured to bend when a force is applied to the patient interface and to stabilize a position of each of the nasal prongs on a portion of the user's face in order to reduce a displacement distance of each of the nasal prongs out of the nares of the user's nose.

18. The patient interface assembly of claim 17, wherein the one or more hinging regions is located adjacent to each of the nasal prongs at a location that is spaced laterally and outwardly in relation to each of the nasal prongs.

19. The patient interface assembly of claim 1, wherein the bonnet comprises a pair of flaps, wherein each flap of the pair of flaps is configured to overlap with the other flap of the pair of flaps at a front portion of the user's head to secure the bonnet to the user's head.

20. The patient interface assembly of claim 19, wherein a degree of overlap of the pair of flaps can be varied to adjust a size of the bonnet.

21. The patient interface assembly of claim 19, wherein an outward-facing surface of the bonnet comprises one or more sections of hook or loop material, and wherein a patient-facing surface of at least one flap of the pair of flaps comprises a complementary section of hook or loop material.

22. A patient interface assembly comprising:
a patient interface comprising: a body and two nasal prongs, each of the nasal prongs extending from the body, each of the nasal prongs having a first end in fluid communication with a supply of breathable gas, and a second end configured to be positioned in a nare of a user's nose, wherein each of the nasal prongs is in fluid communication with the other of the nasal prongs via a manifold comprising a first opening and a second opening, wherein in a first configuration, the first opening is a gas inlet of the manifold and the second opening is a gas outlet of the manifold, and in a second configuration, the second opening is the gas inlet of the manifold, and the first opening is the gas outlet of the manifold;
each of the nasal prongs further including an exterior surface, at least a portion of the exterior surface being a sealing surface configured to seal the nare of the user's nose;
wherein the patient interface is configured so that inspiratory flow and expiratory flow are delivered to and from the user via the two nasal prongs; and
a securement system for the patient interface, the securement system comprising a bonnet, and a two-part releasable attachment arrangement, the two-part releasable attachment arrangement comprising a first patch and a second patch,
the first patch having a patient side and an interface side, the patient side of the first patch being attachable to the bonnet, the interface side of the first patch being provided with a first part of the two-part releasable attachment arrangement,
the second patch having an interface side and a patient side, the patient side of the second patch being provided with a complimentary second part of the two-part releasable attachment arrangement, and
the interface side of the second patch being attachable to or formed as part of the patient interface.

* * * * *

UNITED STATES PATENT AND TRADEMARK OFFICE
CERTIFICATE OF CORRECTION

PATENT NO. : 12,226,579 B2
APPLICATION NO. : 17/253052
DATED : February 18, 2025
INVENTOR(S) : Michael Paul Ronayne Page 1 of 1

It is certified that error appears in the above-identified patent and that said Letters Patent is hereby corrected as shown below:

In the Claims

Column 62, Line 24, Claim 1, delete "second opening and" and insert -- second opening, and --.

Column 63, Line 3, Claim 7, delete "about 30% ,or about" and insert -- about 30%, or about --.

Signed and Sealed this
Twenty-ninth Day of July, 2025

Coke Morgan Stewart
*Acting Director of the United States Patent and Trademark Office*